US009359650B2

(12) United States Patent
Dumesic et al.

(10) Patent No.: US 9,359,650 B2
(45) Date of Patent: Jun. 7, 2016

(54) BIOMASS PRE-TREATMENT FOR CO-PRODUCTION OF HIGH-CONCENTRATION C5- AND C6-CARBOHYDRATES AND THEIR DERIVATIVES

(71) Applicant: Wisconsin Alumni Research Foundation, Madison, WI (US)

(72) Inventors: James A. Dumesic, Verona, WI (US); David Martin Alonso, Madison, WI (US); Jeremy Scott Luterbacher, Madison, WI (US)

(73) Assignees: Wisconsin Alumni Research Foundation, Madison, WI (US); Glucan Biorenewables LLC, St. Louis, MO (US)

( * ) Notice: Subject to any disclaimer, the term of this patent is extended or adjusted under 35 U.S.C. 154(b) by 158 days.

(21) Appl. No.: 14/136,564

(22) Filed: Dec. 20, 2013

(65) Prior Publication Data

US 2015/0176090 A1 Jun. 25, 2015

(51) Int. Cl.
*C13K 1/02* (2006.01)
*C13K 13/00* (2006.01)
*C12P 7/06* (2006.01)

(52) U.S. Cl.
CPC ... *C13K 1/02* (2013.01); *C12P 7/06* (2013.01); *C13K 13/00* (2013.01); *C13K 13/002* (2013.01)

(58) Field of Classification Search
None
See application file for complete search history.

(56) References Cited

U.S. PATENT DOCUMENTS

| | | | | |
|---|---|---|---|---|
| 4,427,453 A | * | 1/1984 | Reitter | C13K 1/02 127/1 |
| 2011/0071306 A1 | | 3/2011 | Robinson | |
| 2012/0302767 A1 | * | 11/2012 | Dumesic et al. | 549/326 |
| 2013/0168227 A1 | | 7/2013 | Fagan et al. | |

FOREIGN PATENT DOCUMENTS

| EP | 2489780 | * | 8/2012 |
|---|---|---|---|
| WO | WO 2005/058856 | * | 6/2005 |

OTHER PUBLICATIONS

Alonso, D.M., Wettstein, S. G., Mellmer, M. A., Gürbüz, E. I., Dumesic, J. A., Integrated conversion of hemicellulose and cellulose from lignocellulosic biomass, *Energy Environ. Sci.* 6, 76-80 (2012).
(Continued)

*Primary Examiner* — Melvin C Mayes
*Assistant Examiner* — Douglas Call
(74) *Attorney, Agent, or Firm* — Joseph T. Leone, Esq.; DeWitt Ross & Stevens S.C.

(57) ABSTRACT

Described is a method of processing biomass to separate it into a liquid fraction enriched in solubilized C5-sugar-containing oligomers and C-5 sugar monomers and a solid fraction enriched in substantially insoluble cellulose and C6-sugar-containing oligomers. The method includes the steps of reacting biomass with a solvent system comprising water, at least one lactone, or at least one furan, or at least one cyclic ether, and at least one acid, for a time and at a temperature to yield the liquid and solid fractions. The liquid and solid fractions may then be separated. Gamma-valeroloactone is a preferred lactone for use in the solvent system. Tetrahydrofuran is a preferred furan species for use in the solvent system.

20 Claims, 31 Drawing Sheets

(56) References Cited

OTHER PUBLICATIONS

Anbarasan, P. et al., Integration of chemical catalysis with extractive fermentation to produce fuels, *Nature* 491, 235-239 (2012).
Binder, J. B., Raines, R. T., Fermentable sugars by chemical hydrolysis of biomass, *Proc. Natl. Acad. Sci.* 107, 4516-4521 (2010).
Dodds, D. R., Gross, R. A., Chemistry: Chemicals from Biomass, *Science* 318, 1250-1251 (2007).
Gürbüz, E. I. et al., Conversion of Hemicellulose into Furfural Using Solid Acid Catalysts in γ-Valerolactone, *Angew. Chem. Int. Ed.* 125, 1308-1312 (2013).
Hodge, D. B., Karim, M. N., Schell, D. J., McMillan, J. D., Soluble and insoluble solids contributions to high-solids enzymatic hydrolysis of lignocellulose, *Bioresour. Technol.* 99, 8940-8948 (2008).
Humbird, D., Aden, A., *Biochemical production of ethanol from corn stover: 2008 state of technology model* (National Renewable Energy Laboratory, 2009).
Kazi, F. K. et al., Techno-economic comparison of process technologies for biochemical ethanol production from corn stover, *Fuel* 89, S20-S28 (2010).
Klein-Marcuschamer, D., Oleskowicz-Popiel, P., Simmons, B. A., Blanch, H. W., The challenge of enzyme cost in the production of lignocellulosic biofuels, *Biotechnol. Bioeng.* 109, 1083-1087 (2012).
Klemes, J., Bulatov, I., Cockerill, T., Techno-economic modelling and cost functions of $CO_2$ capture processes, *Comput. Chem. Eng.* 31, 445-455 (2007).
Kunkes, E. L. et al., Catalytic conversion of biomass to monofunctional hydrocarbons and targeted liquid-fuel classes, *Science* 322, 417 (2008).
Lau, M. W., Dale, B. E., Cellulosic ethanol production from AFEX-treated corn stover using *Saccharomyces cerevisiae* 424A(LNH-ST), *Proc. Natl. Acad. Sci.* 106, 1368-1373 (2009).
Lee, Y. Y., Iyer, P., Torget, R. W., in *Recent Progress in Bioconversion of Lignocellulosics*, Advances in Biochemical Engineering/Biotechnology. P. D. G. T. Tsao et al., Eds. (Springer Berlin Heidelberg, 1999), pp. 93-115.
Luterbacher, J. S., Chew, Q., Li, Y., Tester, J. W., Walker, L. P., Producing concentrated solutions of monosaccharides using biphasic $CO_2$—$H_2O$ mixtures, *Energy Environ. Sci.* 5, 6990-7000 (2012).
Mosier, N. et al., Features of promising technologies for pretreatment of lignocellulosic biomass, *Bioresour. Technol.* 96, 673-686 (2005).
Pagán-Torres, Y. J., Wang, T., Gallo, J. M. R., Shanks, B. H., Dumesic, J. A., Production of 5-Hydroxymethylfurfural from Glucose Using a Combination of Lewis and Brønsted Acid Catalysts in Water in a Biphasic Reactor with an Alkylphenol Solvent, *ACS Catal.* 2, 930-934 (2012).
Park, S., Baker, J. O., Himmel, M. E., Parilla, P. A., Johnson, D. K., Cellulose crystallinity index: measurement techniques and their impact on interpreting cellulase performance, *Biotechnol. Biofuels* 3, 10 (2010).
Peterson, A. A. et al., Thermochemical biofuel production in hydrothermal media: A review of sub- and supercritical water technologies, *Energy Environ. Sci.* 1, 32-65 (2008).
Roman-Leshkov, Y., Chheda, J. N., Dumesic, J. A., Phase modifiers promote efficient production of hydroxymethylfurfural from fructose, *Science* 312, 1933 (2006).
Segal, L., Creely, J. J., Martin, A. E., Conrad, C. M., An Empirical Method for Estimating the Degree of Crystallinity of Native Cellulose Using the X-Ray Diffractometer, *Text. Res. J.* 29, 786-794 (1959).
Selig, M. J. et al., Deposition of Lignin Droplets Produced During Dilute Acid Pretreatment of Maize Stems Retards Enzymatic Hydrolysis of Cellulose, *Biotechnol. Prog.* 23, 1333-1339 (2007).
Sen, S. M. et al., A sulfuric acid management strategy for the production of liquid hydrocarbon fuels via catalytic conversion of biomass-derived levulinic acid, *Energy Environ. Sci.* 5, 9690-9697 (2012).
Shill, K. et al., Ionic liquid pretreatment of cellulosic biomass: Enzymatic hydrolysis and ionic liquid recycle, *Biotechnol. Bioeng.* 108, 511-520 (2011).
Turton, R., Bailie, R. C., Whiting, W. B.,. Shaeiwitz, J. A, *Analysis, synthesis and design of chemical processes* (Pearson Education, 2008).
Von Sivers, M., Zacchi, G., A techno-economical comparison of three processes for the production of ethanol from pine, *Bioresour. Technol.* 51, 43-52 (1995).
Sluiter, A. et al., *Determination of sugars, byproducts, and degradation products in liquid fraction process samples* (National Renewable Energy Laboratory, Golden, CO, 2004).
Wettstein, S. G., Alonso, D. M., Chong, Y., Dumesic, J. A., Production of levulinic acid and gamma-valerolactone (GVL) from cellulose using GVL as a solvent in biphasic systems, *Energy Environ. Sci.* 5, 8199-8203 (2012).
Youngquist, J. T., Rose, J. P., Pfleger, B. F., Free fatty acid production in *Escherichia coli* under phosphate-limited conditions, *Appl. Microbiol. Biotechnol.* 97, 5149-5159 (2013).

\* cited by examiner

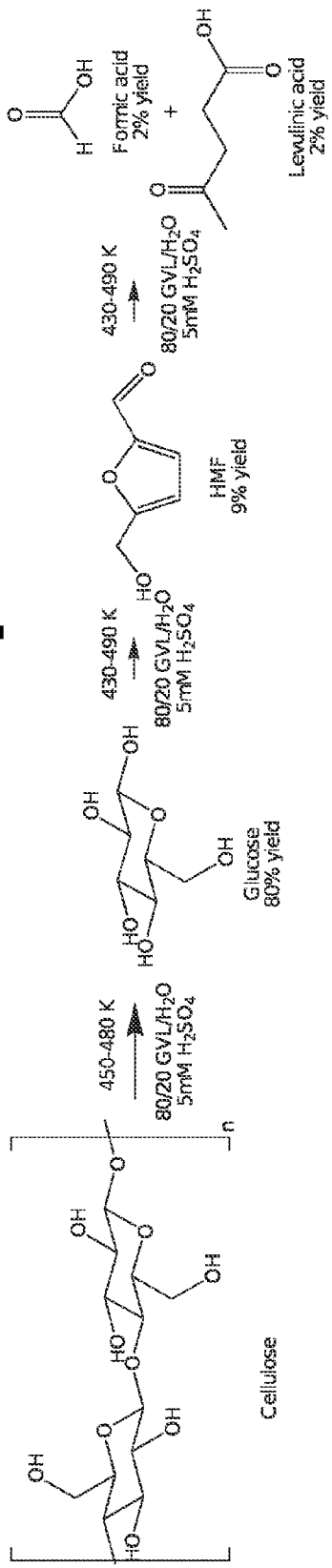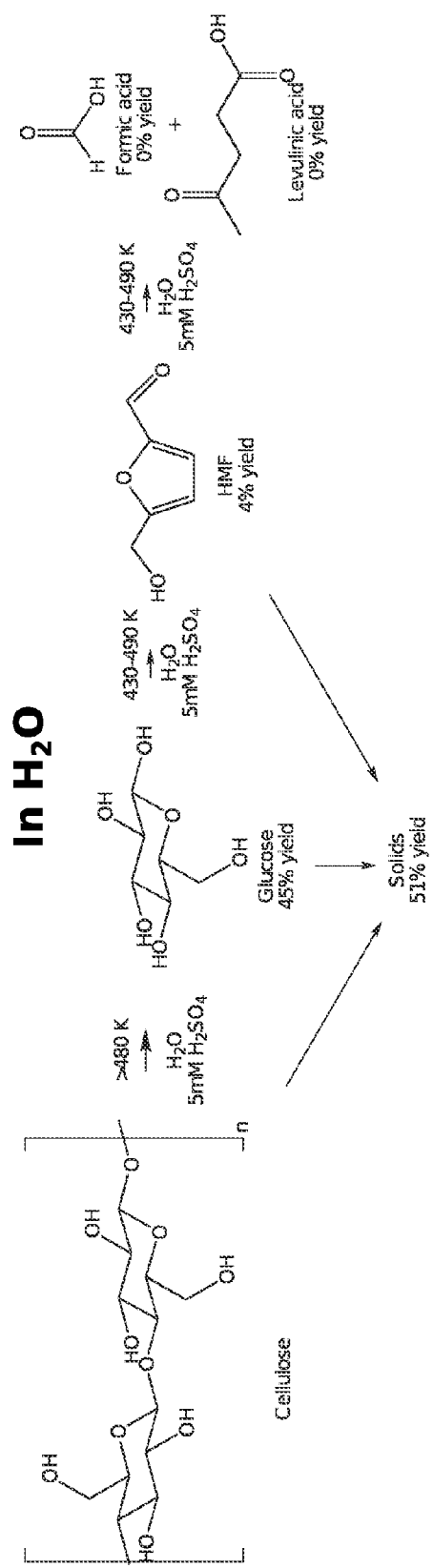
FIG. 1A

FIG. 2A
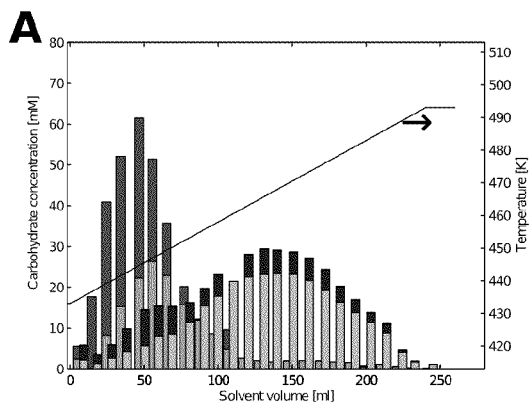
FIG. 2B
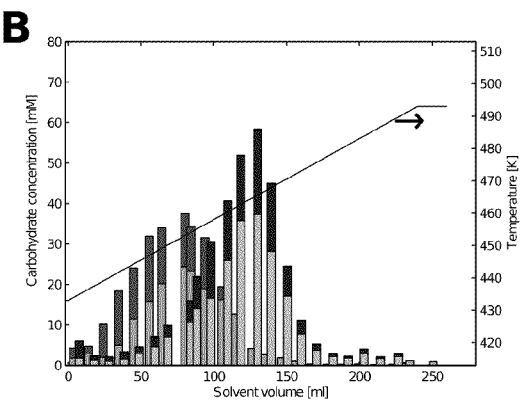
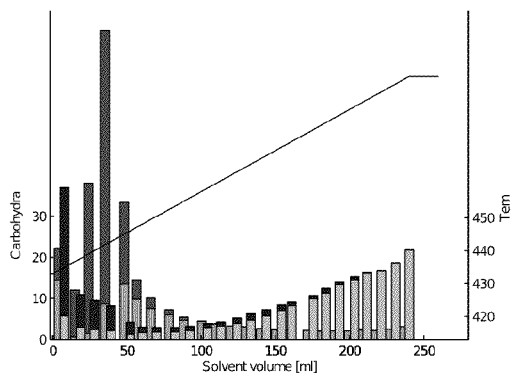
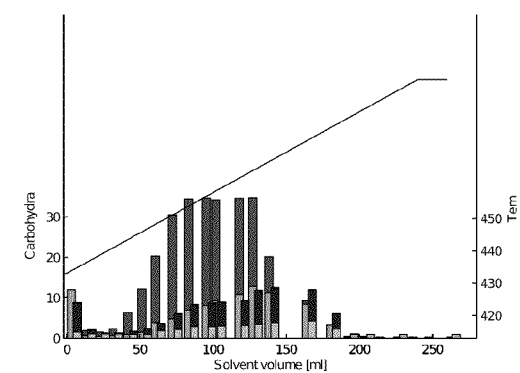
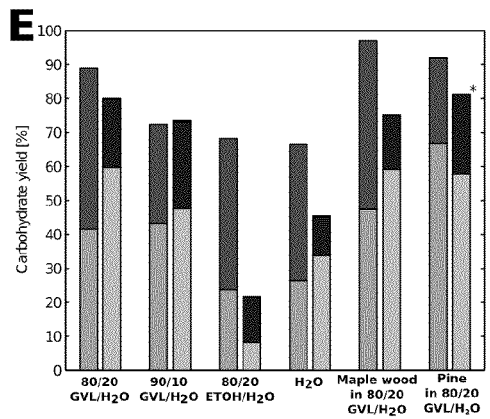
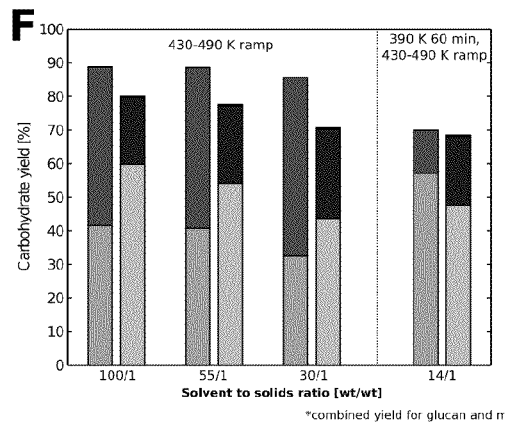
FIG. 2C (middle)
FIG. 2E (bottom)
FIG. 2D (middle)
FIG. 2F (bottom)

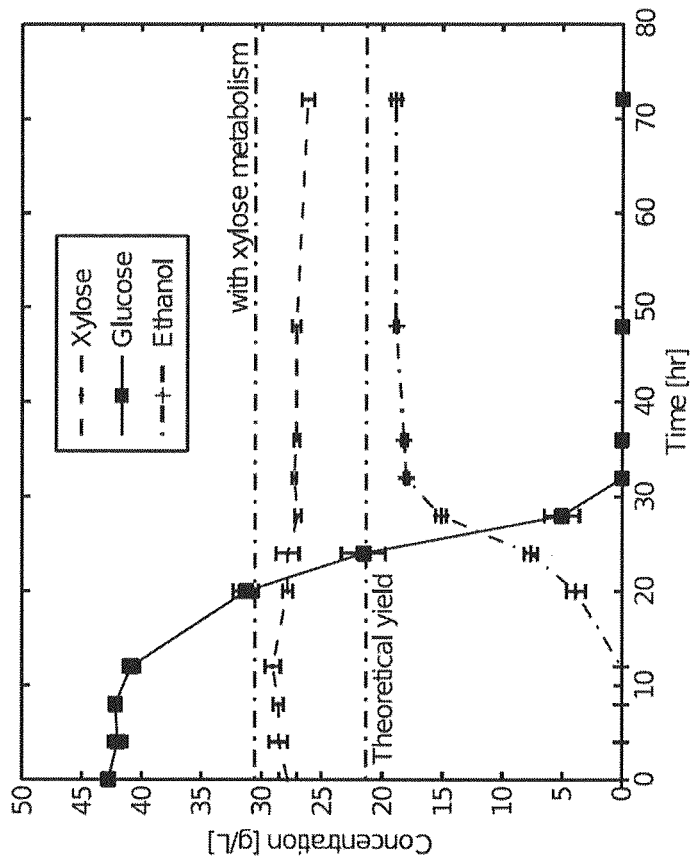
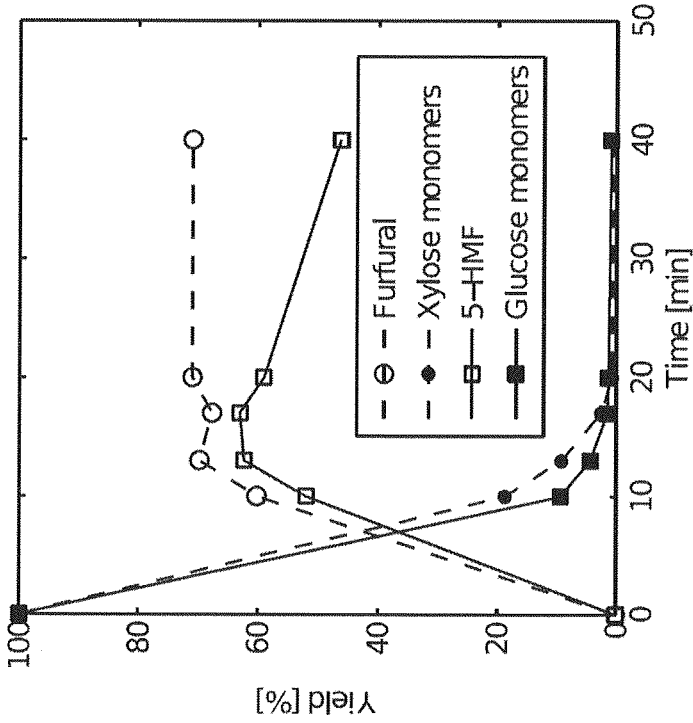
FIG. 4A
FIG. 4B

BIOMASS PRE-TREATMENT FOR CO-PRODUCTION OF HIGH-CONCENTRATION C5- AND C6-CARBOHYDRATES AND THEIR DERIVATIVES

FEDERAL FUNDING STATEMENT

This invention was made with government support under DE-FC02-07ER64494 awarded by the US Department of Energy. The government has certain rights in the invention.

BACKGROUND

Biomass is emerging as a possible renewable alternative to petroleum-based resources in light of increasing environmental, economic and political difficulties associated with fossil fuel extraction and use. Accordingly, biomass-derived sugars have been presented as intermediates for the production of renewable fuels (1-3) and chemicals (4-6). However, producing water-soluble carbohydrates from lignocellulosic biomass requires cleaving ether bonds in xylan and glucan chains, while minimizing further degradation of the resulting $C_5$ and $C_6$ sugars (xylose and glucose) to insoluble degradation products. (See, for example, FIG. 1A). Unfortunately, in aqueous solutions containing low acid concentrations (<10 wt %), the high rate of sugar degradation reactions compared to polysaccharide depolymerization necessitates impractical reaction protocols for converting solid biomass, such as short residence times (10 ms to 1 min) at high temperatures (520-670 K) to obtain high yields of glucose (7). Due to the recalcitrance of crystalline cellulose to deconstruction, high yields at lower reaction temperatures can only be obtained using concentrated mineral acid and/or ionic liquids (8, 9). However, recovery of the mineral acid is critical to the economics of the process, and the cost of ionic liquids can be prohibitive (8-10). Similarly, cellulase enzymes operating at temperatures of 320 K can achieve high glucose yields when converting cellulose rendered accessible by thermochemical pre-treatment. However, the costs associated with producing these enzymes can be substantial compared to the value of the final product (with estimates of $0.35 to 1.47 per gallon of lignocellulose-derived ethanol (11, 12)).

Decoupling the residence times of the solid carbohydrate polymer from its soluble counterpart by flowing a solvent through a heated packed bed of biomass can minimize sugar degradation when using low acid concentrations (13). These systems are limited by their inability to produce concentrated soluble carbohydrate solutions (e.g., 45 to 55% glucose yields when producing a 2 to 4 wt % sugar solution using 1 wt % $H_2SO_4$ in water (13)). In recent work, it has been shown that liquid solutions of gamma-valerolactone (GVL) and water containing dilute concentrations of mineral acids (<0.1 M $H_2SO_4$) can dissolve lignocellulosic biomass and be used to produce levulinic acid and furfural (6, 14).

SUMMARY OF THE INVENTION

Widespread production of chemicals and fuels will require cost-effective methods for breaking down lignocellulosic into its constituent sugars. Disclosed herein is a method for producing soluble carbohydrates from biomass (e.g., corn stover, hardwood, and softwood) at high yields (70 to 90%) in a solvent mixture of biomass-derived γ-valerolactone (GVL), water, and dilute acid (0.05 wt % $H_2SO_4$). GVL promotes thermal saccharification by complete solubilization of the biomass including the lignin fraction. The carbohydrates can be processed within the GVL or they can be recovered and concentrated by extraction from GVL into an aqueous phase by addition of NaCl or liquid $CO_2$. This strategy is well suited for catalytic upgrading to furans or fermentative upgrading to ethanol at high titers and near-theoretical yield. Preliminary techno-economic modeling indicates that the overall process is cost competitive for ethanol production with biomass pre-treatment followed by enzymatic hydrolysis. Of particular note, both technologically and economically, is that the biomass pre-treatment described herein yields a liquid phase containing the lion's share (in some instances >95%) of the C5 sugars present in the raw biomass at concentrations that can be >5 wt %. The pretreatment also yields a solid phase that typically contains >50% of the solid cellulose from the raw biomass.

Residence time of the solvent in the reactor may vary at the choice of the user, and be adjusted empirically based on the selection of the biomass or biomass-derived reactant. Generally, though, it is preferred that the solvent have a residence time in the reactor of from 1 min to 24 hours. Residence times above and below these extremes are within the scope of the process. Thus, the process explicitly covers residence times selected from the group consisting of 1 min to 24 hours, 1 min to 20 hours, 1 min to 12 hours, 1 min to 6 hours, 1 min to 3 hours, 1 min to 2 hours, 1 min to 1 hour, and 1 min to 30 min.

The reaction solvent comprises an organic compound selected from the group consisting of lactones, furans, and cyclic ethers (e.g., tetrahydrofuran, tetrahydropyran, dioxane, etc.) and combinations thereof, mixed with water, and an acid. The acid may be a homogeneous acid, a heterogeneous acid, a Brønsted-Lowry acid, a Lewis Acid, a solid acid, a mineral acid, an organic acid, or any combination of these. (Note that any given acid might be described by more than one of the foregoing identifiers.) If homogeneous, the acid is present in dilute concentration, preferably no greater than about 1000 mM. Thus, acid concentrations between about 0.1 mM and about 500 mM are preferred, more preferably between about 50 mM and about 500 mM, and more preferably still between about 50 mM and about 250 mM. On a weight percentage basis, based on the weight of the lactone/water solvent, the acid is preferably present in an amount of about 0.001 wt % to about 5.0 wt %, more preferably from about 0.01 wt % to about 0.1 wt %.

Thus, disclosed herein is a method of processing biomass. The method comprises reacting biomass with a solvent system comprising water, at least one lactone, furan, or cyclic ether, and at least one acid, for a time and at a temperature to yield a liquid fraction enriched in solubilized C5-sugar-containing oligomers and C-5 sugar monomers and a solid fraction enriched in substantially insoluble cellulose and C6-sugar-containing oligomers. The liquid and solid fractions can then be easily separated for post-treatment upgrading. The lactone is preferably selected from the group consisting of beta-, gamma-, and delta-lactones, and combinations thereof, and (ii) at least about 5 wt % water. Gamma-valerolactone (GVL) is most preferred because it can itself be made from biomass. If a furan is used, it is preferably furan itself or dimethylfuran (DMF). The preferred cyclic ethers are selected from a group consisting of tetrahydrofuran (THF), tetrahydropyran, and dioxane. Tetrahydrofuran, methyltetrahydrofuran, dimethyltetrahydrofuran, furan, methylfuran, dimethylfuran, and combinations thereof, may also be used in the solvent system. The lactones, furans species, or cyclic ethers are generally present in a mass ratio with water, (lactone/furan/ether-to-water, selected from the group consisting of about 70:30, about 75:25, about 80:20, about 85:15, about 90:10, and about 95:5.

The at least one acid may be homogeneous or heterogeneous. The acid may also be a mineral acid, an organic acid, etc. The acid is typically present in the above-noted concentrations. Alternatively, the acid may be present in the solvent system in a concentration sufficient to yield a $[H^+]$ concentration selected from the group consisting of about 0.05M to about 0.5M, about 0.05M to about 0.3M, about 0.05 to about 0.2M, and about 0.05 to about 0.1M. Concentrations above and below these ranges are, however, within the scope of the method.

The biomass may be present in a concentration range selected from the group consisting of from about 5 wt % to about 70 wt %, from about 5 wt % to about 50 wt %, from about 10 wt % to about 50 wt %, from about 10 wt % to about 30 wt %, from about 15 wt % to about 35 wt %, from about 20 wt % to about 30 wt %, from about 10 wt % to about 20 wt %, from about 10 wt % to about 15 wt %, based on the total weight of the biomass and solvent system. The biomass and the solvent system may reacted at a temperature of from about 50° C. to about 250° C. and for a time of from about 1 minute to about 24 hours. The temperature may be held constant or the biomass and the solvent system may be reacted at a dynamic temperature range. For example, the dynamic temperature range may optionally ramp from a first temperature to a second temperature that is higher than the first temperature. The temperature ramp may be linear, non-linear, discontinuous, or any combination thereof.

Another version of the method includes reacting biomass with a solvent system comprising water, gamma-valerolactone (GVL) or tetrahydrofuran (THF), and a mineral acid, for a time of from about 1 min to about 12 hrs, and at a temperature of from about 100° C. to about 200° C., wherein the reaction yields a liquid fraction enriched in solubilized C5-sugar-containing oligomers and C-5 sugar monomers and a solid fraction enriched in substantially insoluble cellulose and C6-sugar-containing oligomers. Again, the liquid fraction may optionally be separated from the solid fraction. The GVL or THF may be present in a mass ratio with water, GVL:water or respectively THF:water, selected from the group consisting of about 70:30, about 75:25, about 80:20, about 85:15, about 90:10, and about 95:5. It is preferred, although not required, that the acid is present in the solvent system in concentration sufficient to yield a $[H^+]$ concentration selected from the group consisting of about 0.05M to about 0.5M, about 0.05M to about 0.5M, about 0.05 to about 0.2M, and about 0.05 to about 0.15M.

The biomass generally is present in a concentration ranging from about 5 wt % to about 70 wt %, preferably from about 5 wt % to about 50 wt %, based on the total weight of the biomass and solvent system. The biomass may be reacted with the solvent system for about 1 min to about 1 hr, and at a temperature of from about 100° C. to about 140° C. The biomass is generally present in a concentration range selected from the group consisting of from about 5 wt % to about 50 wt %, from about 10 wt % to about 30 wt %, from about 10 wt % to about 20 wt %, from about 10 wt % to about 15 wt %, based on the total weight of the biomass and solvent system.

The concentration of the products can be increased by successive additions of biomass during the process. Thus, the biomass may be reacted in a single batch or in multiple additions or continuously. The lactone helps to solubilize the biomass improving the contact between the liquid and the solid biomass. An appropriate mixing of the liquid with the biomass (using conventional agitation equipment) is much preferred to improve yields.

BRIEF DESCRIPTION OF THE DRAWINGS

FIG. 1A is a chemistry overview of the method described herein. The yields depicted in FIG. 1A were obtained using the 2 h temperature ramp. (See the Examples for complete experimental details.)

FIGS. 2A, 2B, 2C, 2D, 2E, and 2F are histograms depicting soluble carbohydrates produced by progressive heating of corn stover in the packed-bed, flow-through reactor shown in FIG. 1B. Carbohydrate concentrations were measured in sequential volume fractions for solvent consisting of 5 mM $H_2SO_4$ in various solvent systems. FIG. 2A: 5 mM $H_2SO_4$ in 80 wt % GVL, 20 wt % water. FIG. 2B: 5 mM $H_2SO_4$ in 90 wt % GVL, 10 wt % water. FIG. 2C: 5 mM $H_2SO_4$ in water. FIG. 2D: 5 mM $H_2SO_4$ in 80 wt % ethanol, 20 wt % water. FIG. 2E is a histogram depicting total yields of soluble carbohydrates in different solvents from corn stover, maple wood and loblolly pine. FIG. 2F is a histogram depicting total yields of soluble carbohydrate from corn stover using 80 wt % GVL and 20 wt % water as a function of solvent-to-solids ratio. The solid line in FIGS. 2A, 2B, 2C, and 2D represents the increasing temperature within the reactor.

FIG. 3A: Separation using 12 wt $\%_{aq}$ NaCl (salt content is given as mass fraction of the salt and water mixture). Separated solutions were all derived from corn stover using a 0.5 to 2 h temperature ramp. Total yields differ slightly from 100% due to experimental error. FIG. 3B: Separation using 1 to 3 subsequent $CO_2$ extractions. The separated solution was derived from corn stover either by a 0.5 h temperature ramp or by initial treatment at 390 K for 1 h followed by the 0.5 h ramp. The aqueous phase was reacted to produce monomers after the first extraction. See FIG. 4A.

FIGS. 4A and 4B are graphs depicting product yields for carbohydrate upgrading. FIG. 4A: Production of furans as a function of time at 443 K. Yields include products analyzed in both phases. FIG. 4B: Fermentation of $CO_2$-extracted feed. Theoretical ethanol yield is represented for glucose and a potential ethanol yield is represented assuming that xylose is metabolized and converted similarly to glucose. Error bars represent the standard deviation of triplicate runs.

FIG. 11A: 12.5 wt % corn stover was reacted with 0.075 M sulfuric acid in 80/20 GVL/water. FIG. 11B: 12.5 wt % corn stover was reacted with 0.15 M sulfuric acid in 80/20 GVL/water.

FIG. 18A: 80 wt % GVL and 20 wt % water mixture. FIG. 18B: 90 wt % GVL and 10 wt % water mixture. All solutions contain 5 mM $H_2SO_4$.

FIG. 19A: water. FIG. 19B: 80 wt % GVL and 20 wt % water. FIG. 19C is a depiction of the peak intensity measurement. FIG. 19D is a graph depicting crystallinity index (CrI) as a function of reaction time at 448 K.

FIG. 20A: 80 wt % GVL and 20 wt % water. FIG. 20B: 90 wt % GVL and 10 wt % water. FIG. 20C: water. FIG. 20D: 80 wt % ethanol and 20 wt % water. All solvent contains 5 mM $H_2SO_4$. The cumulative xylose yield is calculated from the initial volume to the final volume (0 to 260 ml). The cumulative glucose yield is calculated from the final volume to the initial volume (260 to 0 ml). The intersection between the glucose and xylose cumulative yield curve represents the fractionation volume at which equal portions of the total recoverable sugars can be recovered in separate solvent fractions.

FIG. 22A depicts the Effect of NaCl concentration. FIG. 22B depicts the effect of GVL concentration. See Examples for complete experimental details.

FIG. 2A: 5 mM $H_2SO_4$ in 80 wt % GVL, 20 wt % water.

DETAILED DESCRIPTION

Abbreviations and Definitions

Figure 1B:
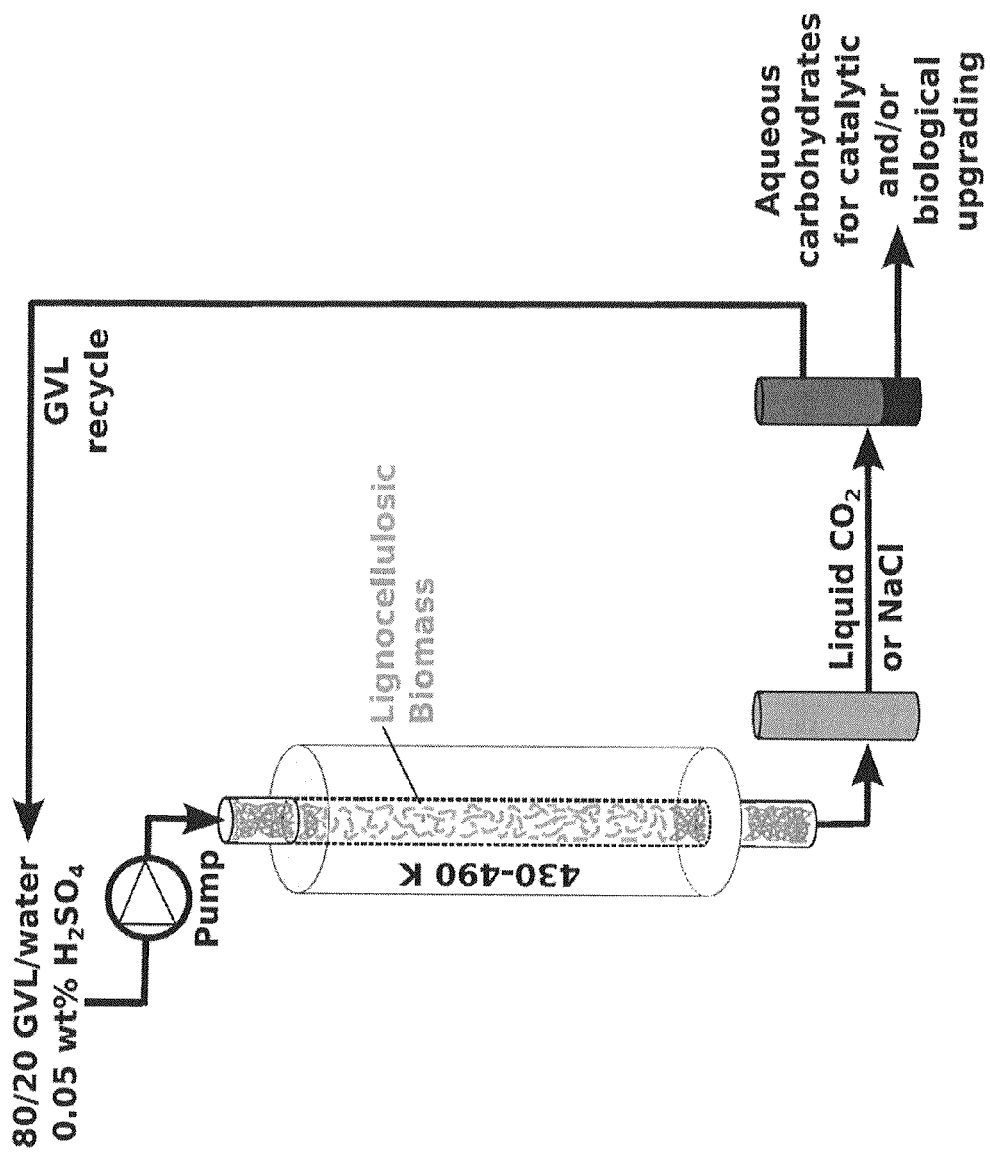
FIG. 1B is a schematic diagram of the reactor apparatus used in the Examples section.

"Biomass" as used herein includes materials containing cellulose, hemicellulose, lignin, protein and carbohydrates such as starch and sugar. Common forms of biomass include trees, shrubs and grasses, corn and corn husks as well as municipal solid waste, waste paper and yard waste. Biomass high in starch, sugar or protein such as corn, grains, fruits and vegetables, is usually consumed as food. Conversely, biomass high in cellulose, hemicellulose and lignin is not readily digestible by humans and is primarily utilized for wood and paper products, fuel, or is discarded as waste. "Biomass" as used herein explicitly includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, vines, hard and soft woods. In addition, biomass includes organic waste materials generated from agricultural processes including farming and forestry activities, specifically including forestry wood waste. "Biomass" includes virgin biomass and/or non-virgin biomass such as agricultural biomass, commercial organics, construction and demolition debris, municipal solid waste, waste paper, and yard waste. Municipal solid waste generally includes garbage, trash, rubbish, refuse and offal that is normally disposed of by the occupants of residential dwelling units and by business, industrial and commercial establishments, including but not limited to: paper and cardboard, plastics, food scraps, scrap wood, saw dust, and the like.

"Biomass-derived"=Compounds or compositions fabricated or purified from biomass.

Brønsted-Lowry Acid/Base=A Brønsted-Lowry acid is defined herein as any chemical species (atom, ion, molecule, compound, complex, etc.), without limitation, that can donate or transfer one or more protons to another chemical species. Mono-protic, diprotic, and triprotic acids are explicitly included within the definition. A Brønsted-Lowry base is defined herein as any chemical species that can accept a proton from another chemical species. Included among Brønsted-Lowry acids are mineral acids, organic acids, heteropolyacids, solid acid catalysts, zeolites, etc. as defined herein. Note that this list is exemplary, not exclusive. The shortened term "Brønsted" is also used synonymously with "Brønsted-Lowry."

"Carbohydrate" is defined herein as a compound that consists only of carbon, hydrogen, and oxygen atoms, in any ratio.

"$C_5$ carbohydrate" refers to any carbohydrate, without limitation, that has five (5) carbon atoms. The definition includes pentose sugars of any description and stereoisomerism (e.g., D/L aldopentoses and D/L ketopentoses). $C_5$ carbohydrates include (by way of example and not limitation) arabinose, lyxose, ribose, ribulose, xylose, and xylulose.

"$C_6$ carbohydrate" refers to any carbohydrate, without limitation, that has six (6) carbon atoms. The definition includes hexose sugars of any description and stereoisomerism (e.g., D/L aldohexoses and D/L ketohexoses). $C_6$ carbohydrates include (by way of example and not limitation) allose, altrose, fructose, galactose, glucose, gulose, idose, mannose, psicose, sorbose, tagatose, and talose.

"Cellulose" refers to a polysaccharide of glucose monomers (($C_6H_{10}O_5)_n$); "cellulosic biomass" refers to biomass as described earlier that comprises cellulose, and/or consists essentially of cellulose, and/or consists entirely of cellulose. Lignocellulosic biomass refers to biomass comprising cellulose, hemicellulose, and lignin. Lignocellulosic biomass comprises xylose, as does hemicellulose. For the experiments described below, dried corn stover was obtained through the Great Lakes Bioenergy Research Center, Madison, Wis., USA. Dried maple wood was obtained from Mascoma corporation, Hanover, N.H.

"Furans" refers to compounds comprising a five-membered aromatic ring with four carbon atoms and one oxygen; that is, any species containing a furan ring, including furan itself, dimethyl furan, etc. Those furans that can dissolve at least about 1 wt % water, and more preferably at least about 5 wt % (or more) of water (up to miscible) are preferred for use in the process described herein.

"Cyclic ether" refers to any compound containing a C—O—C moiety in a ring, excluding the furans defined in the immediately preceding paragraph. Examples include tetrahydrofuran, methyltetrahydrofuran, tetrahydropyran, methyltetrahydropyran, 1,4-dioxane, and the like.

"Glucose-containing oligomers, glucose-containing polymers, Glucose-containing reactant, C6-containing reactant"=Any chemical species, having any type of intramolecular bond type, that comprises a glucose or other C6 sugar unit. The definition explicitly includes glucose-containing disaccharides (such as, but not limited to, sucrose, lactose, maltose, trehalose, cellobiose, kojibiose, nigerose, isomaltose, β,β-trehalose, α,β-trehalose, sophorose, laminaribiose, gentiobiose, turanose, maltulose, palatinose, gentiobiulose, etc.), trisaccharides (such as, but not limited to, isomaltotriose, nigerotriose, maltotriose, maltotriulose, raffinose, etc.), and larger oligosaccharides and polysaccharides, as well as large and more complex glucose-containing polymers and carbohydrates and other polymers and carbohydrates containing C6 sugar units, such as, but not limited to, starch, amylase, amylopectin, glycogen, cellulose, hemicelluloses (e.g., xyloglucan, glucomannan, etc.), lignocellulose, and the like. Linear, branched, and macrocyclic oligomers and polymers containing glucose, including those found in biomass, are explicitly included within the definition. Likewise, "xylose-containing oligomers, xylose-containing polymers, xylose-containing reactant, C5-containing reactant"=Any chemical species, having any type of intramolecular bond type, that comprises a xylose or other C5 sugar unit.

"Homogeneous catalyst"=A catalyst that exists in the same phase (solid, liquid, or gas) as the reactants under reaction conditions.

"Heterogeneous catalyst"=A catalyst that exists in a different phase than the reactants under reaction conditions.

"Lactone" as used herein refers to an unsubstituted or substituted cyclic ester, having a single oxygen heteroatom in the ring, and having from four to six total atoms in the ring— i.e., beta, gamma, and delta lactones, derived from any corresponding C4 to C16 carboxylic acid. Thus, as used herein, the term "lactone" explicitly includes (without limitation) unsubstituted and substituted beta- and gamma-butyrolactone and beta-, gamma-, and delta-valerolactones to beta-, gamma, and delta-hexadecalactones. Some lactones are miscible in water, such as GVL; other lactones have more limited solubility in water. Those lactones that can dissolve at least about 1 wt % water, and more preferably at least about 5 wt % (or more) of water (up to miscible) are suitable for use in the process described herein. Gamma- and delta-lactones are preferred. Gamma-valerolactone is most preferred.

Mineral acid=any mineral-containing acid, including (by way of example and not limitation), hydrochloric acid, nitric acid, phosphoric acid, sulfuric acid, boric acid, hydrofluoric acid, hydrobromic acid, and the like.

Organic acid=any organic acid, without limitation, such as toluenesulfonic acid, formic acid, acetic acid, trifluoroacetic acid, oxalic acid, and the like.

Lewis Acid/Base=A Lewis acid is defined herein as any chemical species that is an electron-pair acceptor, i.e., any chemical species that is capable of receiving an electron pair, without limitation. A Lewis base is defined herein as any chemical species that is an electron-pair donor, that is, any chemical species that is capable of donating an electron pair, without limitation.

The Lewis acid (also referred to as the Lewis acid catalyst) may be any Lewis acid based on transition metals, lanthanoid metals, and metals from Group 4, 5, 13, 14 and 15 of the periodic table of the elements, including boron, aluminum, gallium, indium, titanium, zirconium, tin, vanadium, arsenic, antimony, bismuth, lanthanum, dysprosium, and ytterbium. One skilled in the art will recognize that some elements are better suited in the practice of the method. Illustrative examples include $AlCl_3$, (alkyl)$AlCl_2$, $(C_2H_5)_2AlCl$, $(C_2H_5)_3Al_2Cl_3$, $BF_3$, $SnCl_4$ and $TiCl_4$.

The Group 4, 5 and 14 Lewis acids generally are designated by the formula $MX_4$; wherein M is Group 4, 5, or 14 metal, and X is a halogen independently selected from the group consisting of fluorine, chlorine, bromine, and iodine, preferably chlorine. X may also be a psuedohalogen. Non-limiting examples include titanium tetrachloride, titanium tetrabromide, vanadium tetrachloride, tin tetrachloride and zirconium tetrachloride. The Group 4, 5, or 14 Lewis acids may also contain more than one type of halogen. Non-limiting examples include titanium bromide trichloride, titanium dibromide dichloride, vanadium bromide trichloride, and tin chloride trifluoride.

Group 4, 5 and 14 Lewis acids useful in the method may also have the general formula $MR_nX_{4-n}$; wherein M is Group 4, 5, or 14 metal; wherein R is a monovalent hydrocarbon radical selected from the group consisting of $C_1$ to $C_{12}$ alkyl, aryl, arylalkyl, alkylaryl and cycloalkyl radicals; wherein n is an integer from 0 to 4; and wherein X is a halogen independently selected from the group consisting of fluorine, chlorine, bromine, and iodine, preferably chlorine. X may also be a psuedohalogen. Non-limiting examples include benzyltitanium trichloride, dibenzyltitanium dichloride, benzylzirconium trichloride, dibenzylzirconium dibromide, methyltitanium trichloride, dimethyltitanium difluoride, dimethyltin dichloride and phenylvanadium trichloride.

Group 4, 5 and 14 Lewis acids useful in method may also have the general formula $M(RO)_nR'_mX_{(m+n)}$; wherein M is Group 4, 5, or 14 metal; RO is a monovalent hydrocarboxy radical selected from the group consisting of $C_1$ to $C_{30}$ alkoxy, aryloxy, arylalkoxy, alkylaryloxy radicals; R' is a monovalent hydrocarbon radical selected from the group consisting of $C_1$ to $C_{12}$ alkyl, aryl, arylalkyl, alkylaryl and cycloalkyl radicals; n is an integer from 0 to 4; m is an integer from 0 to 4 such that the sum of n and m is not more than 4; and X is a halogen independently selected from the group consisting of fluorine, chlorine, bromine, and iodine, preferably chlorine. X may also be a psuedohalogen. Non-limiting examples include methoxytitanium trichloride, n-butoxytitanium trichloride, di(isopropoxy)titanium dichloride, phenoxytitanium tribromide, phenylmethoxyzirconium trifluoride, methyl methoxytitanium dichloride, methyl methoxytin dichloride and benzyl isopropoxyvanadium dichloride.

Group 5 Lewis acids may also have the general formula $MOX_3$; wherein M is a Group 5 metal; X is a halogen independently selected from the group consisting of fluorine, chlorine, bromine, and iodine, preferably chlorine. A non-limiting example is vanadium oxytrichloride.

The Group 13 Lewis acids have the general formula $MX_3$; wherein M is a Group 13 metal and X is a halogen independently selected from the group consisting of fluorine, chlorine, bromine, and iodine, preferably chlorine. X may also be a psuedohalogen. Non-limiting examples include aluminum trichloride, boron trifluoride, gallium trichloride, indium trifluoride, and the like.

The Group 13 Lewis acids useful in method may also have the general formula: $MR_nX_{3-n}$, wherein M is a Group 13 metal; R is a monovalent hydrocarbon radical selected from the group consisting of $C_1$ to $C_{12}$ alkyl, aryl, arylalkyl, alkylaryl and cycloalkyl radicals; and n is an number from 0 to 3; and X is a halogen independently selected from the group consisting of fluorine, chlorine, bromine, and iodine, preferably chlorine. X may also be a psuedohalogen. Non-limiting examples include ethylaluminum dichloride, methylaluminum dichloride, benzylaluminum dichloride, isobutylgallium dichloride, diethylaluminum chloride, dimethylaluminum chloride, ethylaluminum sesquichloride, methylaluminum sesquichloride, trimethylaluminum and triethylaluminum.

Group 13 Lewis acids useful in this disclosure may also have the general formula $M(RO)_nR'_mX_{3-(m+n)}$; wherein M is a Group 13 metal; RO is a monovalent hydrocarboxy radical selected from the group consisting of $C_1$ to $C_{30}$ alkoxy, aryloxy, arylalkoxy, alkylaryloxy radicals; R' is a monovalent hydrocarbon radical selected from the group consisting of $C_1$ to $C_{12}$ alkyl, aryl, arylalkyl, alkylaryl and cycloalkyl radicals; n is a number from 0 to 3; m is an number from 0 to 3 such that the sum of n and m is not more than 3; and X is a halogen independently selected from the group consisting of fluorine, chlorine, bromine, and iodine, preferably chlorine. X may also be a psuedohalogen. Non-limiting examples include methoxyaluminum dichloride, ethoxyaluminum dichloride, 2,6-di-tert-butylphenoxyaluminum dichloride, methoxy methylaluminum chloride, 2,6-di-tert-butylphenoxy methylaluminum chloride, isopropoxygallium dichloride and phenoxy methylindium fluoride.

Group 13 Lewis acids useful in this disclosure may also have the general formula $M(RC(O)O)_nR'_mX_{3-(m+n)}$; wherein M is a Group 13 metal; RC(O)O is a monovalent hydrocarbacyl radical selected from the group consisting of $C_2$ to $C_{30}$ alkacyloxy, arylacyloxy, arylalkylacyloxy, alkylarylacyloxy radicals; R' is a monovalent hydrocarbon radical selected from the group consisting of $C_1$ to $C_{12}$ alkyl, aryl, arylalkyl, alkylaryl and cycloalkyl radicals; n is a number from 0 to 3 and m is a number from 0 to 3 such that the sum of n and m is not more than 3; and X is a halogen independently selected from the group consisting of fluorine, chlorine, bromine, and iodine, preferably chlorine. X may also be a psuedohalogen. Non-limiting examples include acetoxyaluminum dichloride, benzoyloxyaluminum dibromide, benzoyloxygallium difluoride, methyl acetoxyaluminum chloride, and isopropoyloxyindium trichloride.

The most preferred Lewis acids for use in the method are metal halides generally and more specifically transition metal halides, lanthanoid metal halides, and Group 5, 13, and 14 metal halides. Preferred among the metal halides are metal chlorides. Preferred transition metal chlorides include, but are not limited to, $TiCl_4$, $VCl_3$. and the like. Preferred Group 13 and 14 metal halides and chlorides include, but are not limited to, $BF_3$, $AlCl_3$, $SnCl_4$, $InCl_3$, and $GaCl_3$. Preferred lanthanoid chlorides include, but are not limited to, $LaCl_3$, $DyCl_3$ and $YbCl_3$.

The terms "solid acid" and "solid acid catalyst" are used synonymously herein and can comprise one or more solid acid materials. The solid acid catalyst can be used independently or alternatively can be utilized in combination with one or more mineral acid or other types of catalysts. Exemplary solid acid catalysts which can be utilized include, but are not limited to, heteropolyacids, acid resin-type catalysts, mesoporous silicas, acid clays, sulfated zirconia, molecular sieve materials, zeolites, and acidic material on a thermo-stable support. Where an acidic material is provided on a thermo-stable support, the thermo-stable support can include for example, one or more of silica, tin oxide, niobia, zirconia, titania, carbon, alpha-alumina, and the like. The oxides themselves (e.g., $ZrO_2$, $SnO_2$, $TiO_2$, etc.) which may optionally be doped with additional acid groups such as $SO_4^{2-}$ or $SO_3H$ may also be used as solid acid catalysts. Further examples of solid acid catalysts include strongly acidic ion exchangers such as cross-linked polystyrene containing sulfonic acid groups. For example, the Amberlyst®-brand resins are functionalized styrene-divinylbenzene copolymers with different surface properties and porosities. (These types of resins are designated herein as "Amb" resins, followed by a numeric identifier of the specific sub-type of resin where appropriate.) The functional group is generally of the sulfonic acid type. The Amberlyst®-brand resins are supplied as gellular or macro-reticular spherical beads. (Amberlyst® is a registered trademark of the Dow Chemical Co.) Similarly, Nafion®-brand resins are sulfonated tetrafluoroethylene-based fluoropolymer-copolymers which are solid acid catalysts. Nafion® is a registered trademark of E.I. du Pont de Nemours & Co.)

Solid catalysts can be in any shape or form now known or developed in the future, such as, but not limited to, granules, powder, beads, pills, pellets, flakes, cylinders, spheres, or other shapes.

Zeolites may also be used as solid acid catalysts. Of these, H-type zeolites are generally preferred, for example zeolites in the mordenite group or fine-pored zeolites such as zeolites X, Y and L, e.g., mordenite, erionite, chabazite, or faujasite. Also suitable are ultrastable zeolites in the faujasite group which have been dealuminated.

The term "solute" is broadly defined herein to include any non-reactive salt (such as NaCl, NaBr, and any other inorganic or organic salts) or other non-reactive organic or inorganic solutes that drive the formation of an organic layer and a substantially immiscible organic layer containing the lactone when the solute is added to the product mixture after reaction. Sodium salts are preferred. Sodium chloride is also preferred.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations shall include the corresponding plural characteristic or limitation, and vice-versa, unless otherwise specified or clearly implied to the contrary by the context in which the reference is made.

The processes described herein can be run in batch mode, semi-continuous mode, and/or continuous mode, all of which are explicitly included herein.

All combinations of method or process steps as used herein can be performed in any order, unless otherwise specified or clearly implied to the contrary by the context in which the referenced combination is made.

The methods described and claimed herein can comprise, consist of, or consist essentially of the essential elements and limitations of the disclosed methods, as well as any additional or optional ingredients, components, or limitations described herein or otherwise useful in synthetic organic chemistry.

The Method:

Disclosed herein is a method of using GVL/water solutions for producing soluble carbohydrates (a versatile biomass platform) from raw biomass such as corn stover, hardwood, softwood, and the like. The preferred method utilizes a batch reactor at a temperature of 350 K to 490 K. It can be combined with a flow-through reactor using a progressive temperature increase from about 430 to about 490 K. FIG. 1A depicts the essential chemical reactions contemplated in the method. The top series of reactions in FIG. 1A are the reactions that take place in a solvent system comprising 80% GVL and 20% water. The bottom series of reactions in FIG. 1A are the reactions that take place when using just water as the solvent. FIG. 1B depicts an exemplary flow-through reactor (including a solvent recycling loop) that can be used to perform the reactions described herein. Note that the reactor depicted in FIG. 1B is exemplary. Other reactor configurations can be used with equal success. The methods described herein may be run continuously, semi-batch-wise, or batch-wise. Also disclosed herein is a method to separate the sugars from GVL into a concentrated aqueous phase that is compatible with subsequent upgrading by chemical or biological processes.

Figure 25:
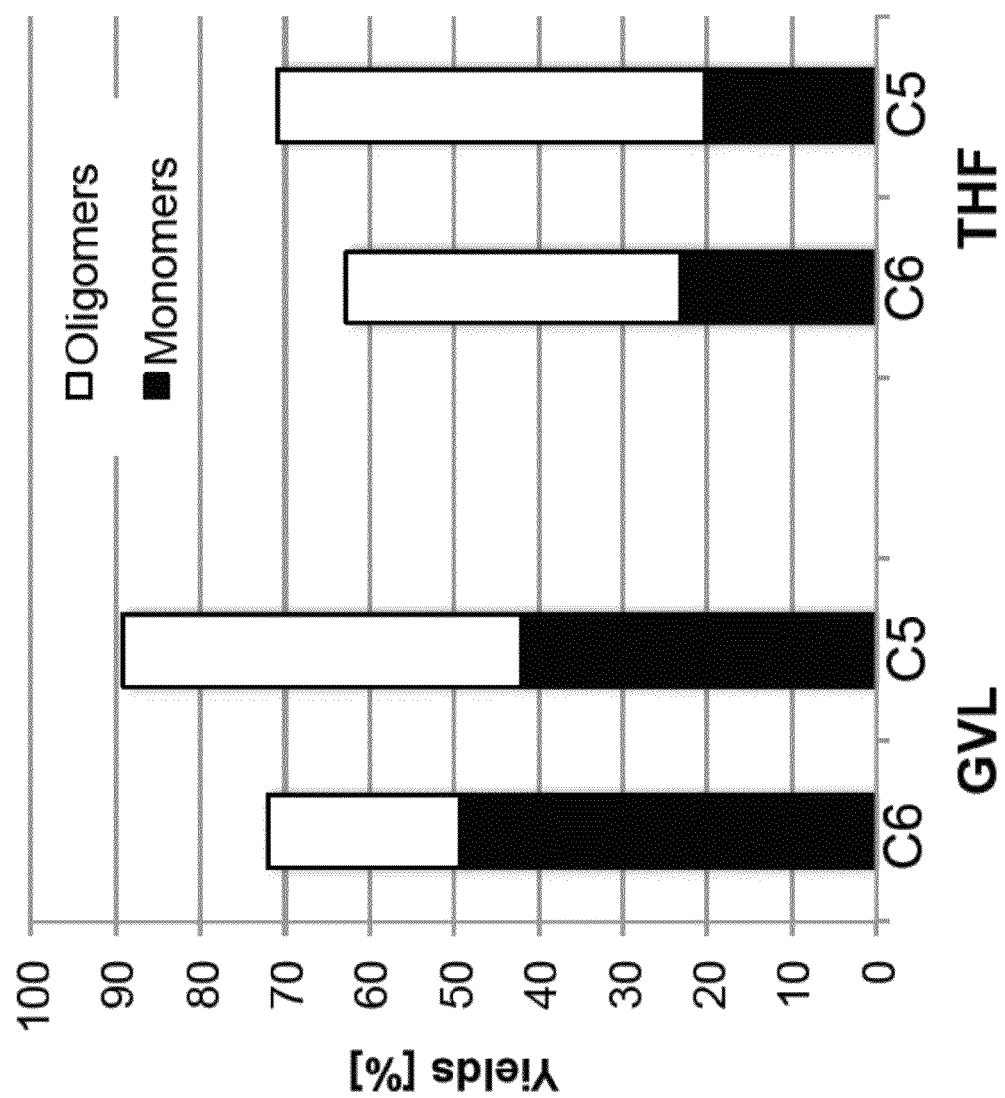
FIG. 25 is a histogram comparing the yields of soluble carbohydrates produced by progressive heating of maple wood in the packed-bed, flow-through reactor shown in FIG. 1B using GVL (left hand side) or GVL (right hand side). Yields were obtained using mixtures containing 5 mM $H_2SO_4$, 20 wt % water and 80 wt % GVL (left hand side) or 80 wt % THF (right hand side).

The results shown in FIGS. 2A and 2B show the concentrations of soluble carbohydrate achieved in the GVL/water solvent as a function of solvent volume flowed through the reactor packed with corn stover. FIG. 2A depicts the results for a mixture containing 80 wt % GVL and 20 wt % water (80/20 GVL/water). FIG. 2B depicts the results for a mixture containing 90 wt % GVL and 10 wt % water (90/10 GVL/water). Both solutions contain a low concentration of mineral acid, i.e., 5 mM $H_2SO_4$ (~0.05 wt %). In comparison, dilute acid pretreatment of biomass is typically carried out with at least 0.5 to 2 wt % $H_2SO_4$ (15). In both cases, the concentrations of $C_5$ (xylose and xylo-oligomer) and $C_6$ sugars (glucose and gluco-oligomer) reach maxima at temperatures between 430 and 470 K. In contrast, when water is used as a solvent (FIG. 2C), the $C_6$ concentration increases continuously with increasing temperature up to 490 K and potentially beyond. When an alternate organic solvent such as ethanol is used in place of GVL, the $C_6$ sugar concentration shows a similar profile to that obtained with GVL, but lower by a factor of three (see FIG. 2D). However, a solvent such as tetrahydrofuran can be used to obtain similar yields to those obtained with GVL (see FIG. 25). Therefore, the presence of GVL or THF promotes cellulose deconstruction, most of which occurs below 480 K.

Figure 18A:
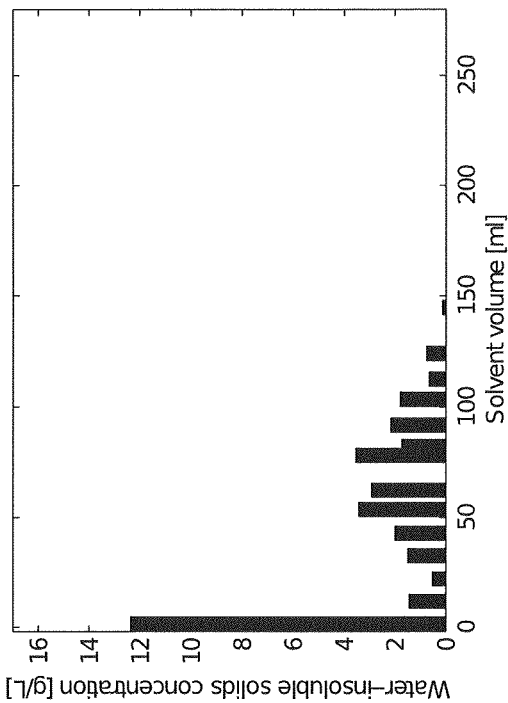
FIGS. 18A and 18B are histograms depicting the production of water-insoluble solids by progressive heating of corn stover in a packed tubular reactor employing different liquid solvents and a 2 hr 430-490 K temperature ramp.
Figure 18B:
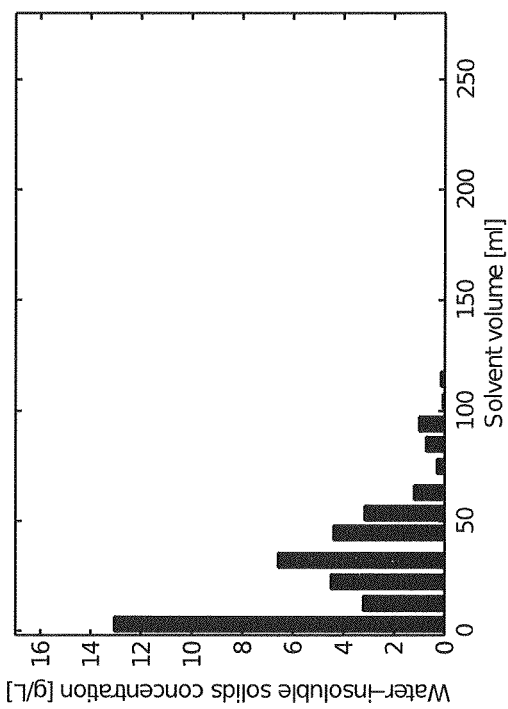
Figure 19B:
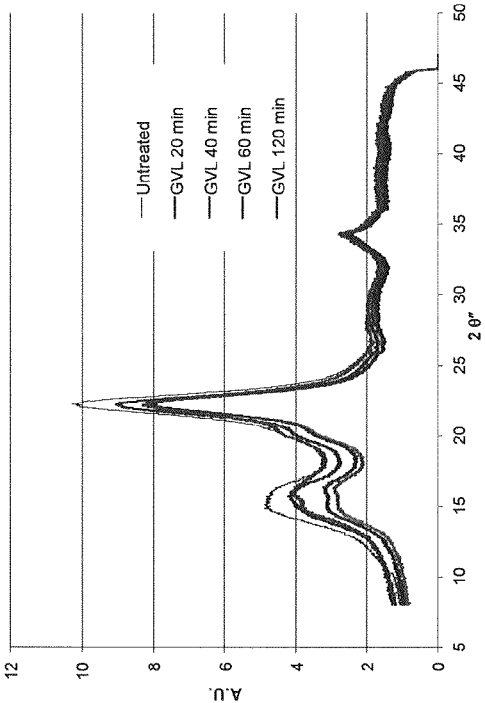
FIGS. 19A, 19B, 19C, and 19D are graphs depicting cellulose x-ray diffraction patterns after treatment at 448 K in the presence of 5 mM $H_2SO_4$ in different solvents.
Figure 19D:
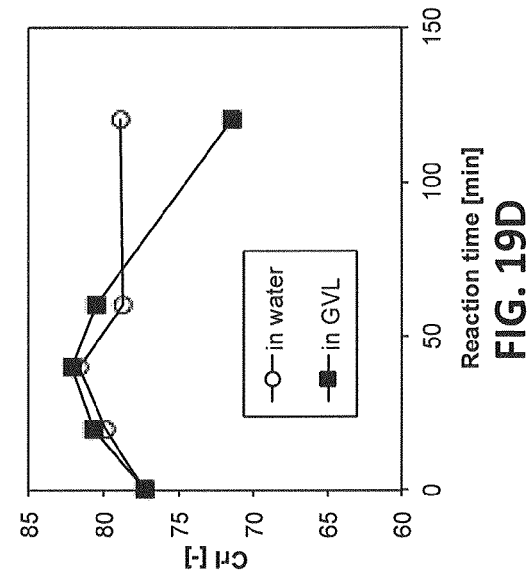
Figure 19A:
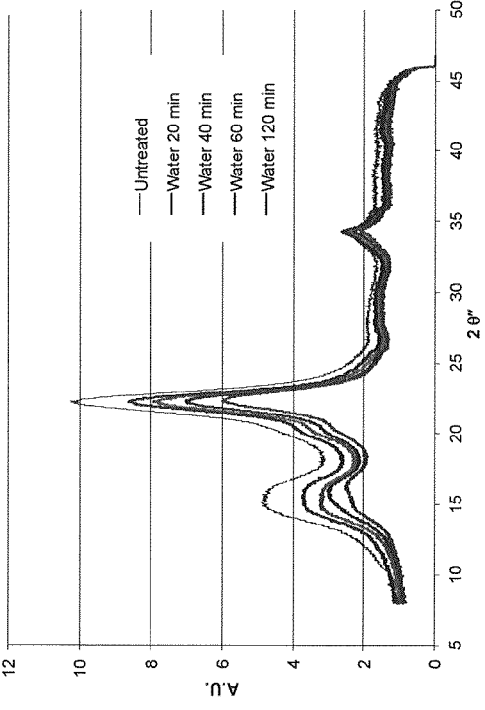
Figure 19C:
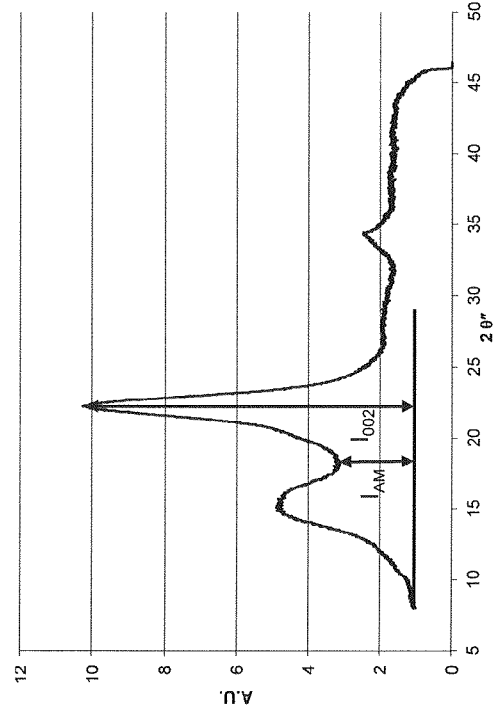

Increased deconstruction of biomass in the presence of GVL can be attributed to the complete solubilization of biomass solids, including the lignin fraction. In addition to providing a soluble lignin stream with potential as a feedstock for future upgrading, GVL prevents re-precipitation of lignin by-products on the surface of cellulose. This re-precipitation is a known phenomenon in water that decreases accessibility to the reactive cellulose surface (16). Water insoluble solids corresponding to 95% and 84% of the original lignin were recovered for experiments conducted with 80/20 and 90/10 GVL/water, respectively. See the Examples and FIGS. 18A and 18B. In addition, it appears that the presence of GVL plays a role in disrupting cellulose crystallinity, as suggested by x-ray diffraction measurements of pure cellulose showing an increased fraction of more reactive amorphous cellulose after dissolution and re-isolation. See the Examples and FIGS. 19A, 19B, 19C, and 19D. FIGS. 19A-19D depict cellulose x-ray diffraction patterns after treatment at 448 K in the presence of 5 mM $H_2SO_4$ in water (FIG. 19A) and 80 wt % GVL and 20 wt % water (FIG. 19B). FIG. 19C shows the peak intensity measurement. FIG. 19D depicts the crystallinity index (CrI) as a function of reaction time at 448 K. In both water and in the presence of GVL the crystallinity index initially increases as a fraction of amorphous cellulose is hydrolyzed. However, beyond 40 min at 448 K, CrI decreases in the presence of GVL, demonstrating the continuous disruption of the crystalline portion of cellulose by GVL and creation of more reactive amorphous cellulose. The proportionally smaller drop in crystallinity of cellulose treated in the presence of water is likely due to the precipitation of water-insoluble humins (carbohydrate degradation products) being included in the remaining solids (14). Because humins are soluble in GVL, they do not contribute to the drop in crystallinity observed in the presence of this solvent.

Figure 20A:
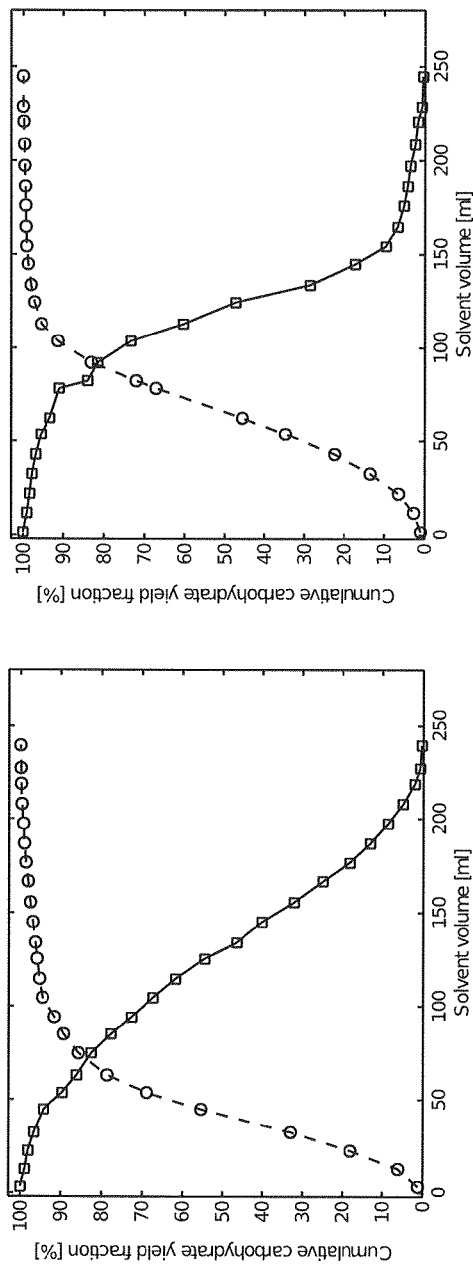
FIGS. 20A, 20B, 20C, and 20D are graphs depicting cumulative yield of carbohydrate as a function of solvent volume for various solvent systems.
Figure 20B:
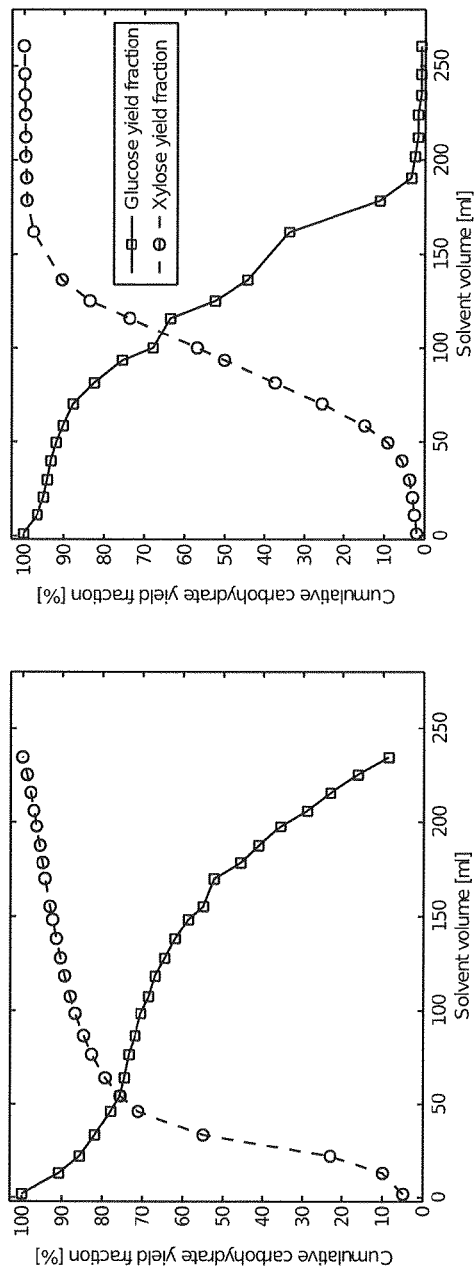
Figure 20C:
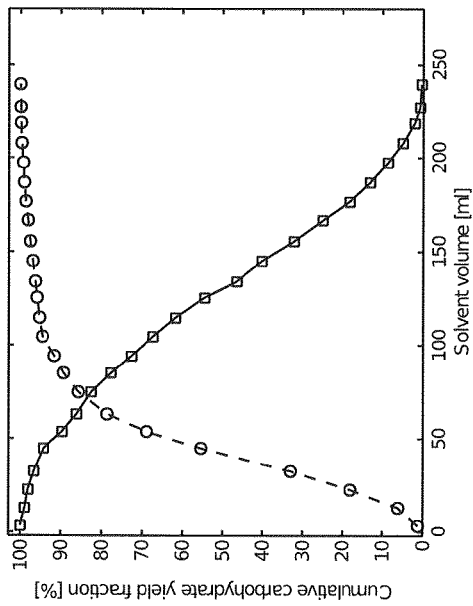
Figure 20D:
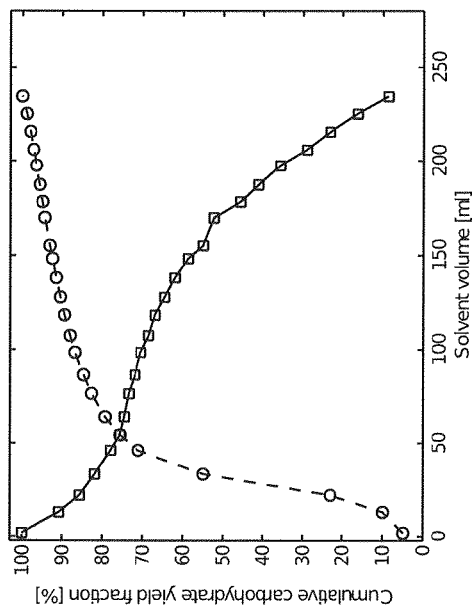

Biomass conversion in the GVL/water solvent system leads to a significant increase in the overall sugar yields, compared to conversion with water or water/ethanol as the solvent. Specifically, $C_5$ recovery increases by 5 to 20 percentage points, and overall recovery of $C_6$ sugars increases by 2- to 4-fold. See FIG. 2E. These $C_5$ and $C_6$ yields of 89 and 80% are similar to those achievable using ionic liquids or enzymes, rather than those obtainable with water (9, 17, 18). With 80/20 GVL/water, about 90 to 95% of polysaccharides are recovered as known soluble products when dehydration products such as furfural, 5-hydroxymethylfurfural (5-HMF) and levulinic acid (all potential GVL precursor molecules (6)) are included. (See FIG. 1A.) In comparison, conversion in water leaves 50% of the $C_6$ and 30% of the $C_5$ fractions as unidentified solid products (FIG. 1A). Unlike reports using enzymatic processes (15), it was found that $C_5$ and $C_6$ sugar yields in GVL/water are not sensitive to biomass type, as they are comparable for corn stover, maple wood, and loblolly pine (FIG. 2E). Furthermore, when using GVL/water as a solvent, it is possible to recover over 80% of the $C_5$ and $C_6$ sugars in separate volume fractions without additional separation processes. See the Examples and FIGS. 20A, 20B, 20C, and 20D. Note that the intersection between the glucose and xylose cumulative yield curves represents the fractionation volume at which equal portions of the total recoverable sugars can be recovered in separate solvent fractions. In FIGS. 20A and 20B, this yield is at or above 80% using solvent volumes less than about 100 mL. Depending on both technological and economic factors, producing separate $C_5$ and $C_6$ sugar streams is highly beneficial because it provides opportunities to implement separate upgrading processes for the soluble $C_5$ sugars versus the $C_6$ sugars derived from cellulose depolymerization.

Decreasing the temperature ramp duration from 2 h to 30 min increases the concentrations of carbohydrates by reducing four-fold the volume of solvent flowed through the biomass while reducing sugar yields by less than 10%. See FIG. 2F. When a 20 wt % biomass solution in 80/20 GVL/water with 0.15 M $H_2SO_4$ was treated for 1 h at 390 K, most of the $C_5$ sugars and lignin are solubilized, and the remaining solids can be placed in the flow-through reactor where the same 0.5 h temperature ramp with 80/20 GVL/water and 5 mM $H_2SO_4$ is used. This approach decreases the solvent-to-solids ratio by over 50% while maintaining similar $C_6$ yields and lowering $C_5$ yields by only 15% (FIG. 2F). Accordingly, the concentration of soluble $C_6$ sugars is doubled compared to conventional treatments. Moreover, when furfural is taken into account, the overall conversion of xylan to known products remains above 90% for this biomass processing strategy. See Table 1.

Figure 3A:
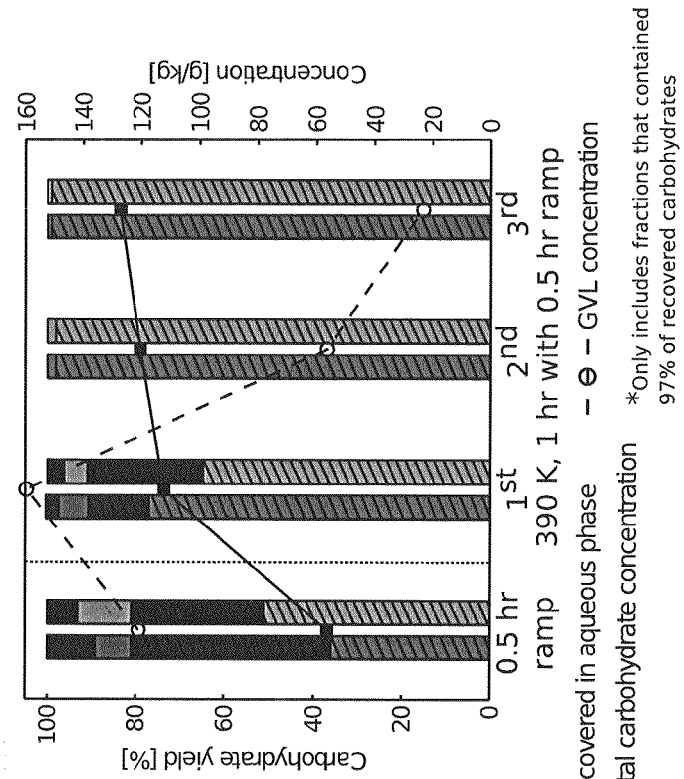
FIGS. 3A and 3B are histograms depicting the separation of 80 wt % GVL and 20 wt % water mixtures.
Figure 3B:
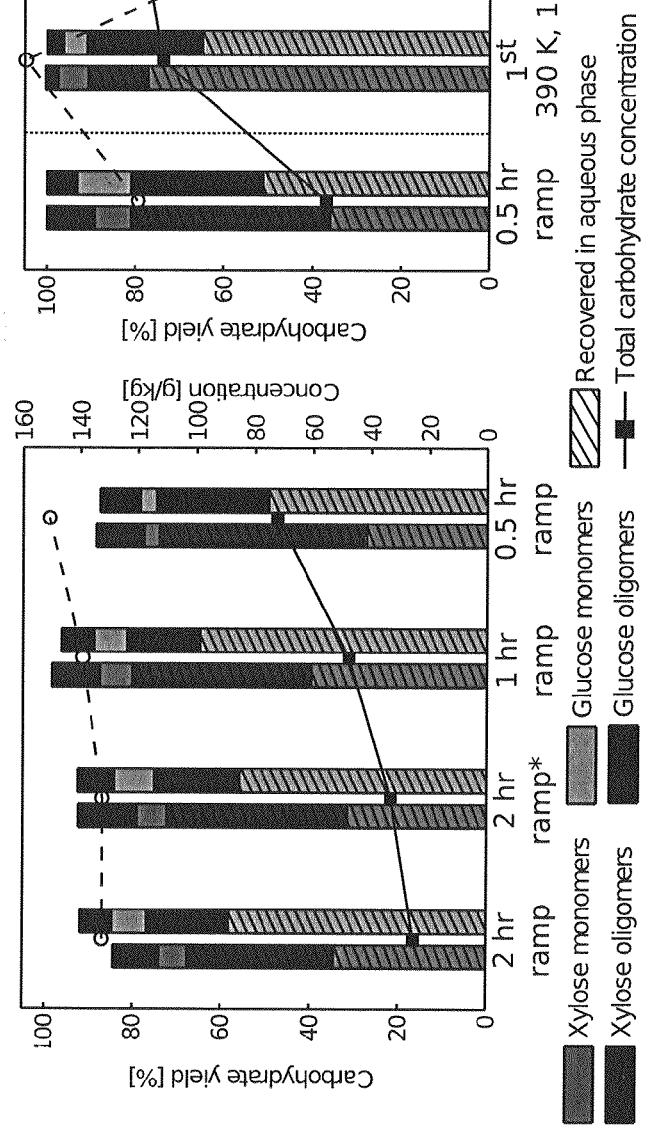
Figure 21:
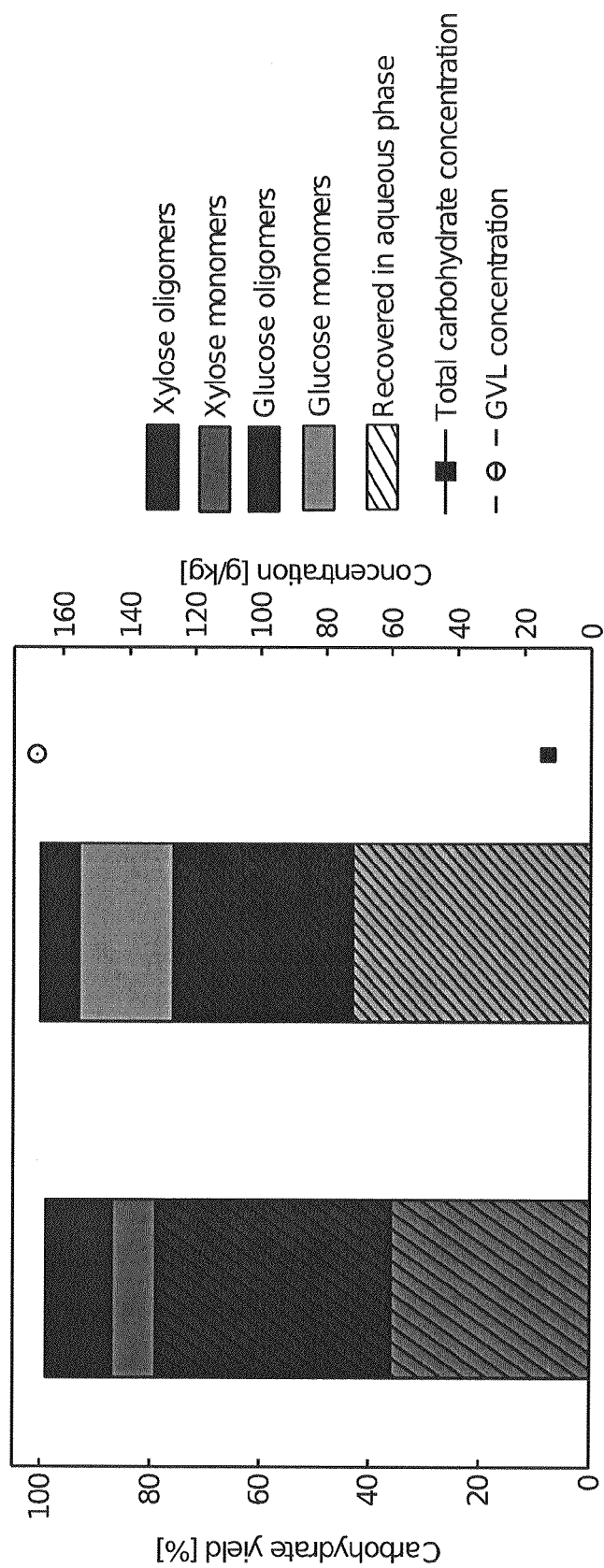
FIG. 21 is a histogram depicting re-extraction of carbohydrates from $CO_2$-extracted GVL. One (1) g water was added to 10 g of $CO_2$-extracted GVL. This mixture was extracted with $CO_2$ as detailed in the methods section. Stacked bars represent fractions of the total carbohydrate yield based on the initial amount of xylose or glucose in the $CO_2$-extracted GVL. Single points represent the total concentration of sugars or GVL in the aqueous phase. The hashed area represents carbohydrates recovered in the aqueous phase.

The aqueous phase can be separated along with 75 to 91% of the carbohydrates from GVL/water solvent systems by addition of NaCl (14) (FIG. 3A) or liquid $CO_2$ (FIG. 3B). In FIGS. 3A and 3B, -■- is total carbohydrate concentration (g/kg; right-hand Y-axis); -○- is GLV concentration (wt %; left-hand Y-axis); each bar represents carbohydrate product yield as noted in the key (wt %; left-hand Y-axis.) This separation yields a total soluble carbohydrate concentration of up to 112 g/L, depending on the ramp time and method used. In the case of GVL extraction by $CO_2$, over 70% of the non-extracted carbohydrates that remain in the organic phase can be recovered in a single re-extraction from the organic phase after water addition (0.1 g water per g of extracted GVL). See the Examples and FIG. 21. FIG. 21 shows the carbohydrate yield when the carbohydrates Furthermore, if $CO_2$-extracted GVL is recycled, then any recycled sugars will contribute to increased concentrations after biomass conversion. The GVL remains stable during recycle. See Examples. Subsequent extractions of the separated aqueous phase with $CO_2$ lower the GVL concentration in water below 2 wt % while removing less than 4% of the carbohydrates and increasing their concentration to a total of 127 g/L. See FIG. 3B. This concentration corresponds to 65 to 85% of the highest concentrations obtained by enzymatic hydrolysis (150-200 g/L (17, 18)) and is over 8-fold higher than concentrations that could have been obtained with pure water as a solvent (<15 g/L). Moreover, the concentrated monomer solutions obtained from salt separation and $CO_2$ extraction are clear, as opposed to the slurries obtained using enzymatic hydrolysis or acidic-aqueous processing.

The $C_5$ and $C_6$ sugars recovered in the aqueous phase can be upgraded by catalytic dehydration to furfural and 5-hydroxymethylfurfural (HMF) (4). Furan selectivity is increased when these hydrophobic compounds are continuously extracted into an organic phase, such as 2-sec-butyl-phenol (SBP) (19). Aqueous phase modifiers such as NaCl (present by default in the salt-separated aqueous carbohydrate stream) and a Lewis acid catalyst such as $AlCl_3$ further promote selectivity to furans by increasing their partitioning towards the organic phase and catalyzing carbohydrate isomerization, respectively (4, 19). FIG. 4A shows the yields of furfural and 5-HMF obtained as a function of reaction time at 443 K by conversion of the soluble carbohydrates (monomers and oligomers) produced from corn stover using the 2 h temperature ramp. The separated aqueous phase was used without further treatment, except for the addition of $AlCl_3$ and the presence of the SBP organic phase. (See the Examples for complete experimental details.) The yields of 60% and 70% (FIG. 4A) for production of 5-HMF and furfural (>94% recovered in the SBP), respectively, are within 5% of yields

TABLE 1

Product yields after pre-treatment at 390 K for 1 hr in 80 wt % GVL, 20 wt % water and 0.15 (corn stover) or 0.05M $H_2SO_4$ (maple wood) in a batch reactor, followed by treatment of the remaining unwashed solids in the flow-through reactor for 30 min with a 430-490 K temperature ramp.

| | | | Yields [%] | | | | | | | | |
|---|---|---|---|---|---|---|---|---|---|---|---|
| Substrate | Glucose | Gluco-oligomers | Total C6 Sugars | LA | HMF | Glucan prods. | Xyl | Xylo-oligos. | Total C5 Sugars | Fur | Xylan prods. |
| Corn stover | 47.5 | 21 | 68.5 | 10.8 | 5.4 | 84.7 | 57.1 | 12.9 | 70.0 | 22.3 | 92.3 |
| Maple wood | 43.7 | 21.2 | 64.9 | 1.6 | 12.2 | 78.7 | 59.2 | 13.8 | 73.0 | 17.5 | 90.5 | reported from pure glucose and xylose, despite the presence of oligomers and other biomass by-products (19, 20).

Figure 22:
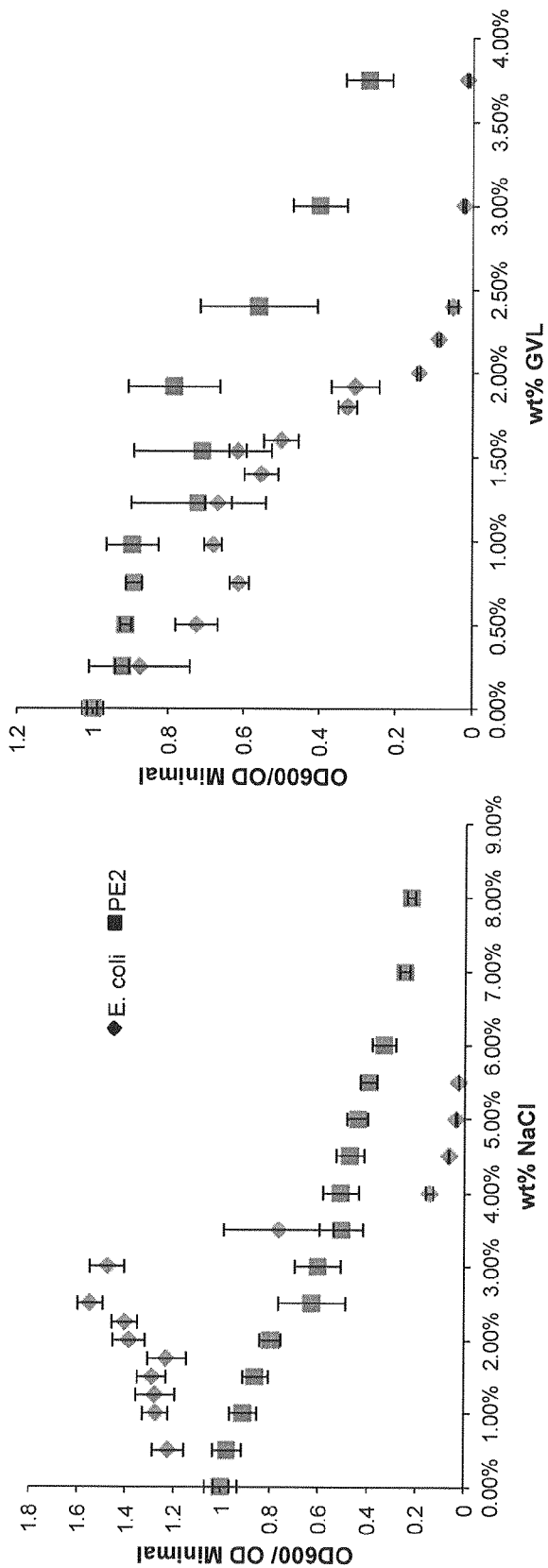
FIGS. 22A and 22B are graphs depicting the effect of GVL and NaCl concentration on microbial growth of *E. coli* MG1655 (*E. coli*) and *S. cerevisiae* PE2 (PE2). Optical densities were measured after 24 hr of growth for *E. coli* and after 40 hr of growth for PE2.
Figure 23:
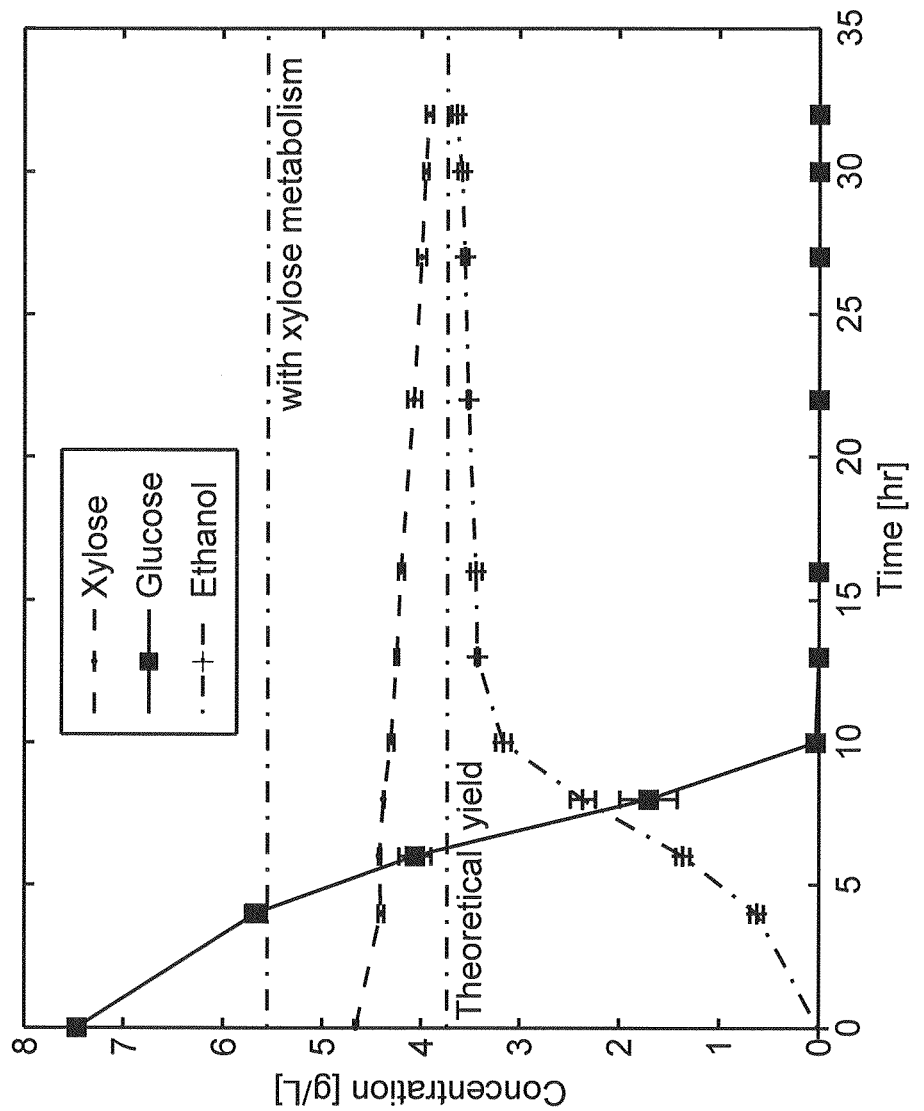
FIG. 23 is a graph depicting the fermentation of salt-separated feed. Theoretical ethanol yield is represented for glucose and a potential ethanol yield is represented assuming that xylose is metabolized as well. Error bars represent the standard deviation of triplicate runs.
Figure 24:
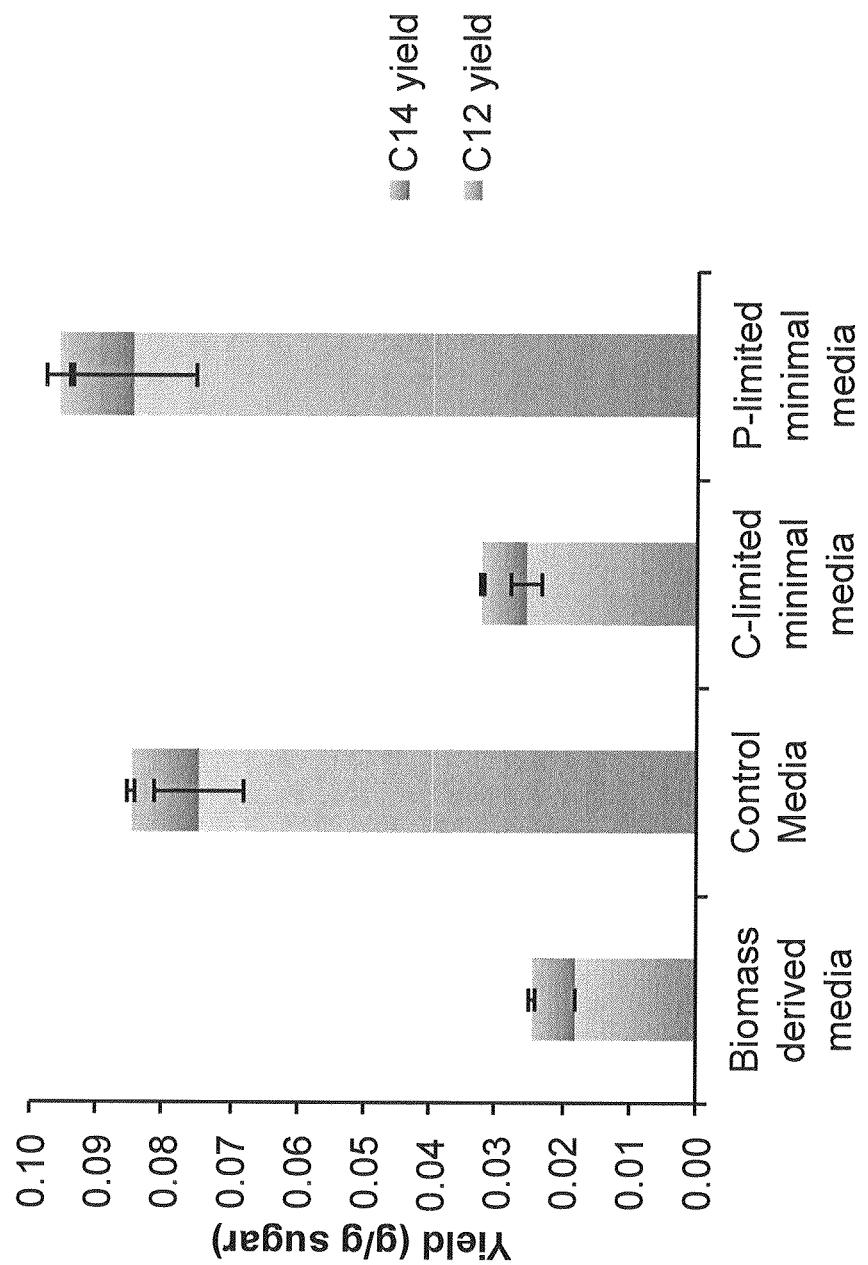
FIG. 24 is a histogram depicting fatty acid yield using various carbon sources. Biomass derived media was obtained using a 30 min temperature ramp and 80/20 GVL in the flow-through reactor. C and P stand for carbon and phosphate, respectively.

Using liquid $CO_2$ to extract GVL eliminates the use of salt and reduces the GVL concentration, both of which can inhibit microbial growth. See the Examples and FIGS. 22A and 22B. These two figures show the effect of GVL and NaCl concentration on microbial growth of *E. coli* MG1655 (*E. coli*) and *S. cerevisiae* PE2 (PE2). Optical densities were measured after 24 hr of growth for *E. coli* and after 40 hr of growth for PE2. FIG. 22A shows the effect of NaCl concentration. FIG. 22B shows the effect of GVL concentration. In addition, the glucose oligomers present in the recovered aqueous phase (see FIGS. 3A and 3B) can be converted into monomers (preferable starting products for biological upgrading) in the acidic aqueous environment present in the aqueous phase. In an aqueous monomer solution produced using $CO_2$ extraction and the 0.5 h temperature ramp and then diluted by 75%, robust growth of *Saccharomyces cerevisiae* PE2 (PE2) was observed. Note that even when using this non-evolved industrial yeast strain, and using minimal media, the yield of ethanol from glucose corresponded to 87% of the theoretical value (FIG. 4B). Ethanol yields that were 95% of theoretical, as well as fatty acid production, were both achieved using more dilute salt-extracted feed. See the Examples and FIGS. 23 and 24. FIG. 23 is graph depicting the results of fermenting the salt-separated feed. The ethanol yield from glucose was equal to 95% of the theoretical value. Theoretical ethanol yield is represented for glucose and a potential ethanol yield is represented assuming that xylose is metabolized as well. Error bars represent the standard deviation of triplicate runs. FIG. 24 is a histogram depicting the fatty acid yield using various carbon sources. Biomass derived media was obtained using a 30 min temperature ramp and 80/20 GVL in the flow-through reactor. Fatty acid yield was comparable in biomass-derived media to yields obtained with C-limited media. Control media was formulated in minimal media with a defined mixture of glucose and xylose equal to concentrations found in the biomass derived media and designed to be phosphate limited as described in previous work (3).

Because the PE2 strain does not metabolize xylose, the ethanol titer obtained using this $CO_2$-extracted feed (19 g/L) was below that of a potential titer of 31 g/L that could be achieved if xylose had been converted at a similar yield (which has been demonstrated using engineered yeast strains (21)) (FIG. 4B). Using a similar dilution of the more concentrated feed containing 127 g/L carbohydrates, ethanol titers of 29 g/L (86% yield) were obtained from glucose after 6 days of fermentation. Assuming xylose conversion at similar yields, a potential titer of 48 g/L would have been reached. Efforts are currently underway to study new strains and/or evolve one to grow robustly in the equivalent corresponding hydrolysate carbohydrates, which could lead to ethanol concentrations of 60 g/L. An industrial scenario recently published by the National Renewable Energy Laboratory (NREL) assumed ethanol titers around 50 g/L (22). Using current carbohydrate recovery yields and assuming that an undiluted carbohydrate stream can be used for fermentation, a techno-economic model shows that such a process could produce ethanol at a minimum selling price of $4.87/gallon of gasoline equivalent (GGE), versus $5.13/GGE for the NREL scenario (22) (data not shown). Most of the savings are due to the absence of enzymes.

Figure 1C:
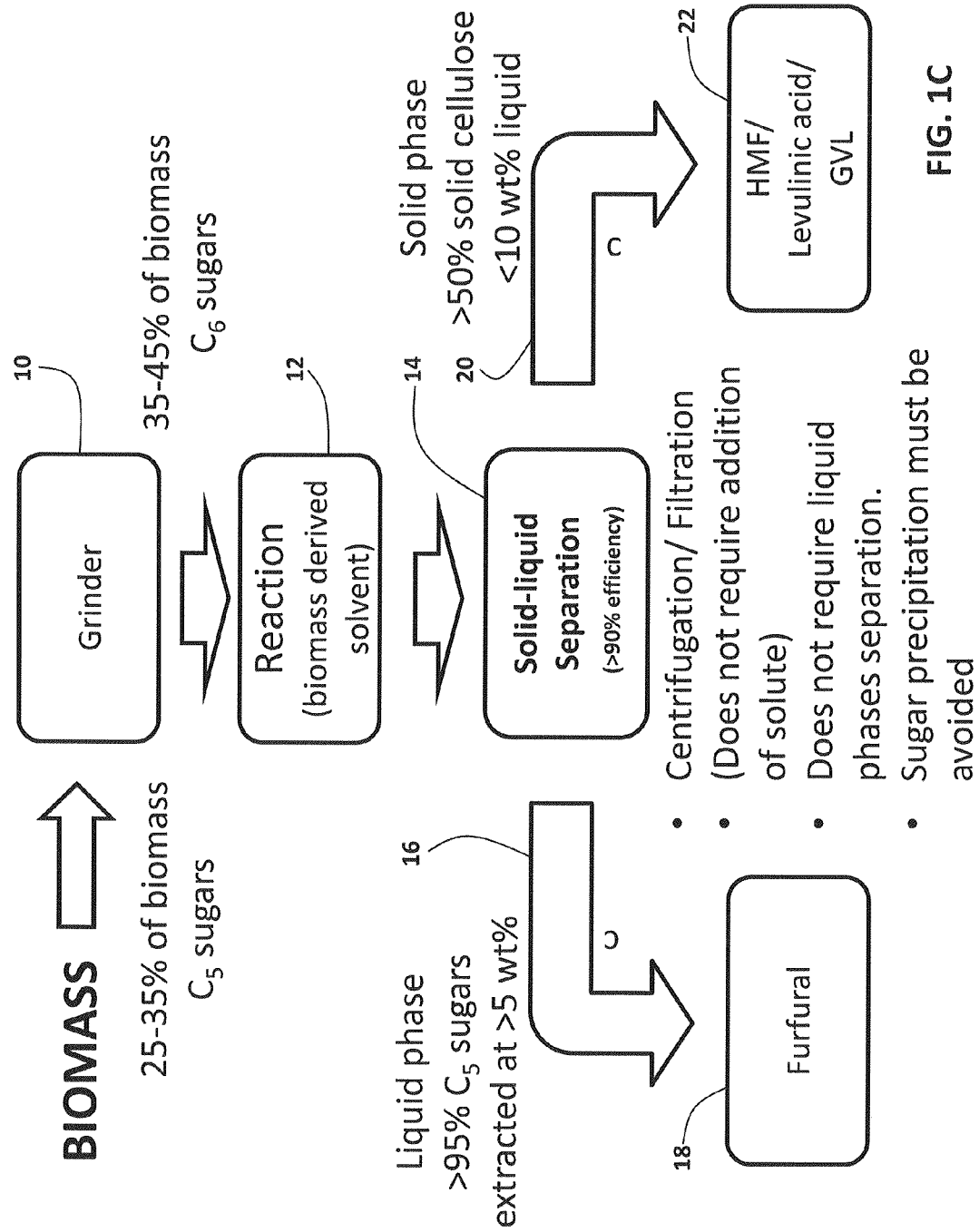
FIG. 1C is a flow chart depicting the method of treating biomass with a biomass-derived solvent to yield a liquid fraction containing a large proportion of the C5-sugars present in the biomass and a solid fraction containing a majority of the solid cellulose present in the biomass.
Figure 1D:
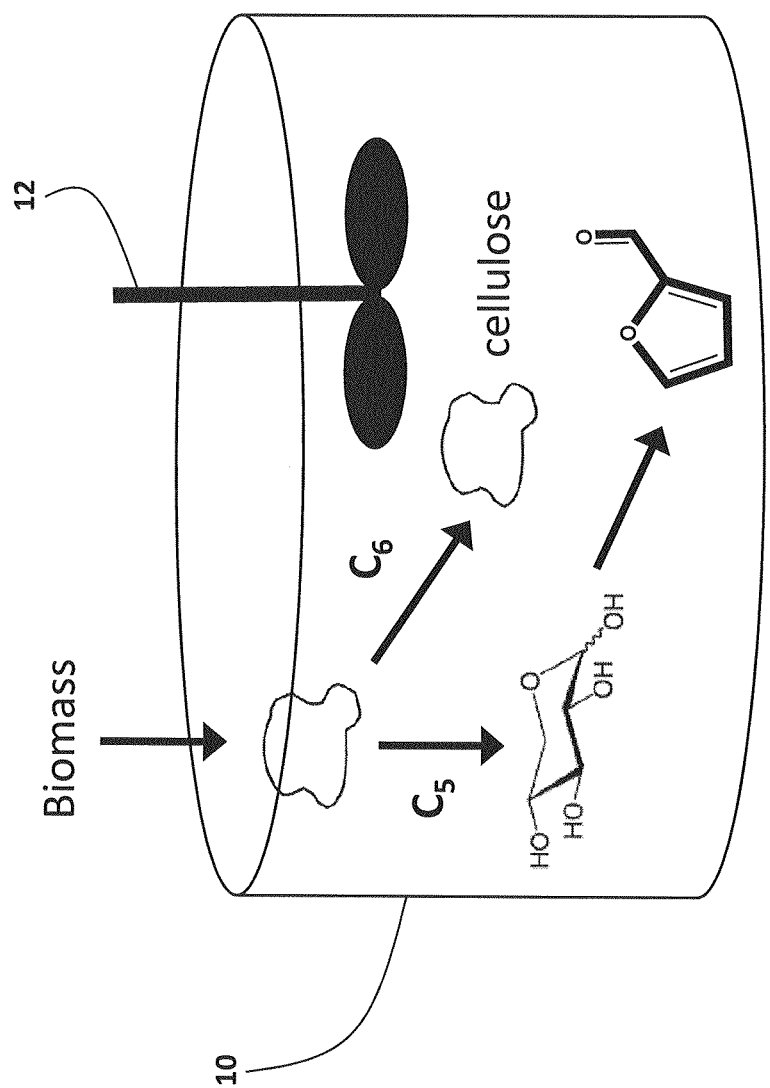
FIG. 1D is a schematic diagram depicting the separation of raw biomass into a liquid C5-containing fraction and a solid cellulose-containing fraction, followed by upgrading of the C5 sugars in the liquid fraction to furfural.

Referring now to FIG. 1C, which is a flow chart illustrating the initial treatment of the raw biomass, roughly 25-35% of raw biomass is C5 sugars. Roughly 35-45% of raw biomass is C6 sugars. (These ranges are estimates and any give single biomass source may comprise different proportions of C5 and C6 sugars than those given.) Unless the raw biomass has already been finely comminuted (e.g., saw dust), the raw biomass can be ground into smaller particulates as shown at 10 in FIG. 1C. The grinding is done by any conventional method using conventional equipment. The ground biomass is then extracted with a biomass-derived solvent, such as a lactone, and most preferably GVL. Agitating the biomass/solvent combination is preferred, as is shown schematically in FIG. 1D. FIG. 1D depicts a conventional reactor vessel 10 with an agitator 12. Disposed in the reactor is the raw biomass, which is solublized by the solvent and converted into a liquid C5 fraction (which may optionally be upgraded into furfural) and an insoluble cellulose fraction, which is subsequently separated from the liquid fraction. The mixing/extraction step is done for a time and at a temperature that maximizes the extraction of C5 sugars into the liquid phase, while minimizing solubilization of the solid cellulose-containing fraction. The preferred temperature range is from about 90° C. to about 150° C., and more preferably from about 100° C. to about 140° C. The time of extraction preferably is from about 10 min to about 3 hours and more preferably from about 10 min to 2 hours and more preferably still from about 10 min to about 90 min. The extraction solvent system should also be acidic. Mineral acids are preferred; sulfuric acid is most preferred. The acid should be present in a concentration of from about 0.05 M to about 0.5 M, and more preferably from about 0.05 M. to about 0.3 M.

The biomass can be added batch-wise, semi-continuously, or continuously, generally at a concentration of about 20 wt % or greater (with single or multiple additions of biomass). As biomass is dissolved by the GVL, more biomass can be added to the reactor, thereby increasing the final concentration of soluble sugars, while also ensuring through mixing of the biomass with the extraction solvent. If the C5 sugars are destined to be converted into furfural, the extraction times may advantageously be extended because at longer reaction times at least a portion of the xylose extracted from the biomass is converted into furfural during the extraction step.

The liquid and solids are then separated by conventional methods using conventional equipment. Care must be taken during the separation step to avoid precipitation of the solubilized sugars; this can be done, for example, by performing the separation step at elevated temperatures. Preferably the separation is performed at a temperature from about 100° C. to about 150° C. Keeping the sugars in solution becomes more important as the sugar concentration of the extracting solvent becomes greater (and thus approaches the solubility limit of the sugars). Tables 2 and 3 compare the sugar yields using two different extracting solvent systems (80/20 GVL/water+0.075M $H_2SO_4$ and 70/30 GVL/water+0.075M $H_2SO_4$), at 130° C. versus 25° C.

TABLE 2

Extraction Yields, 80/20 GVL/water + 0.075M $H_2SO_4$
80/20 GVL/Water 0.075M SA.
20 wt % corn cob
45 min at 130° C.

|  | 130° C. | 25° C. |
| --- | --- | --- |
| Glucose | 61.08 | 35.44 |
| XMG | 70.27 | 43.78 |
| Arabinose | 81.61 | 58.40 |
| Formic acid | 74.16 | 79.65 |
| Acetic acid | 86.29 | 84.08 |
| Levulinic acid | 82.14 | 83.54 |
| GVL | 89.29 | 86.16 |
| HMF | 87.77 | 82.94 |

TABLE 2-continued

Extraction Yields, 80/20 GVL/water + 0.075M $H_2SO_4$
80/20 GVL/Water 0.075M SA.
20 wt % corn cob
45 min at 130° C.

|          | 130° C. | 25° C. |
|----------|---------|--------|
| Furfural | 76.32   | 75.28  |

Results given in wt %

TABLE 3

Extraction Yields, 70/30 GVL/water + 0.075M $H_2SO_4$)
70/30 GVL/Water 0.075M SA.
20 wt % + 20 wt % corn cob
45 + 60 min at 130° C.

|               | 130° C. | 25° C. |
|---------------|---------|--------|
| Glucose       | 51.70   | 33.09  |
| XMG           | 58.20   | 38.86  |
| Arabinose     | 65.37   | 42.69  |
| Formic acid   | 60.42   | 71.44  |
| Acetic acid   | 79.12   | 76.58  |
| Levulinic acid| 76.87   | 75.81  |
| GVL           | 84.07   | 82.17  |
| HMF           | 78.36   | 70.16  |
| Furfural      | 71.73   | 75.42  |

Results given in wt %

Figure 5:
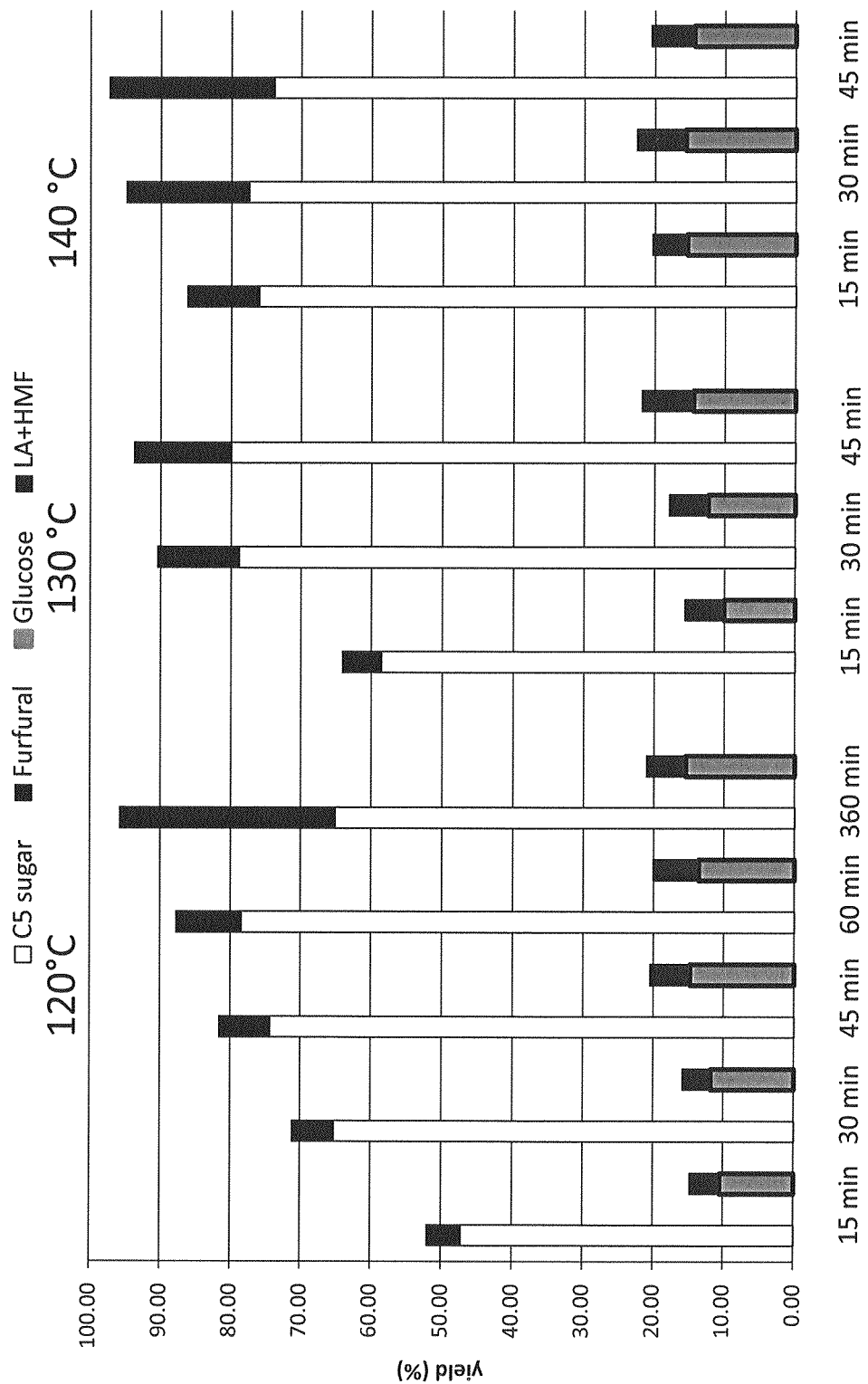
FIG. 5 is a histogram showing the extraction yield for 20 wt % corn cob particles using an extraction solvent comprising 0.075 M sulfuric acid in 80/20 GVL/water. The reactions were run at 120° C., 130° C., and 140° C.

As shown in FIG. 5, under the extraction conditions noted above, C5 sugars can be extracted at high yields with minimal extraction of C6 sugars. FIG. 5 depicts the results of running the same extraction at various times and temperatures. The reaction conditions were: 20 wt % corn cob particles using an extraction solvent comprising 0.075 M sulfuric acid in 80/20 GVL/water. The reactions were run at 120° C., 130° C., and 140° C., and for various times (as shown in FIG. 5). The results for each unique time and temperature combination is depicted as paired bars. The left-hand bar of each pair shows the yield of C5 sugar and furfural (stacked); the right-hand bar of each pair shows the yield of glucose and levulinic acid (LA) and hydroxymethylfurfural (HMF) (stacked). As can be clearly seen in FIG. 5, under these conditions, the amount of extracted C6 sugars never approaches 30% and is often well under 20%. On contrast, the yield of solublized C5 sugars is always above 50% and well above 90% in many instances. Of particular note in FIG. 5 is that while soluble C5 sugar yields increase with the increasing time and temperature of the extraction step, the corresponding yields of C6 sugars plateaus. Thus, at longer extraction times and high extraction temperatures, the ratio of C5 sugars to C6 sugars in the liquid fraction increases. This is significant because a more complete separation of the C5 sugars and the C6 sugars maximizes the efficiency of upgrading the two result product streams separately in subsequent steps (if desired).

Figure 6:
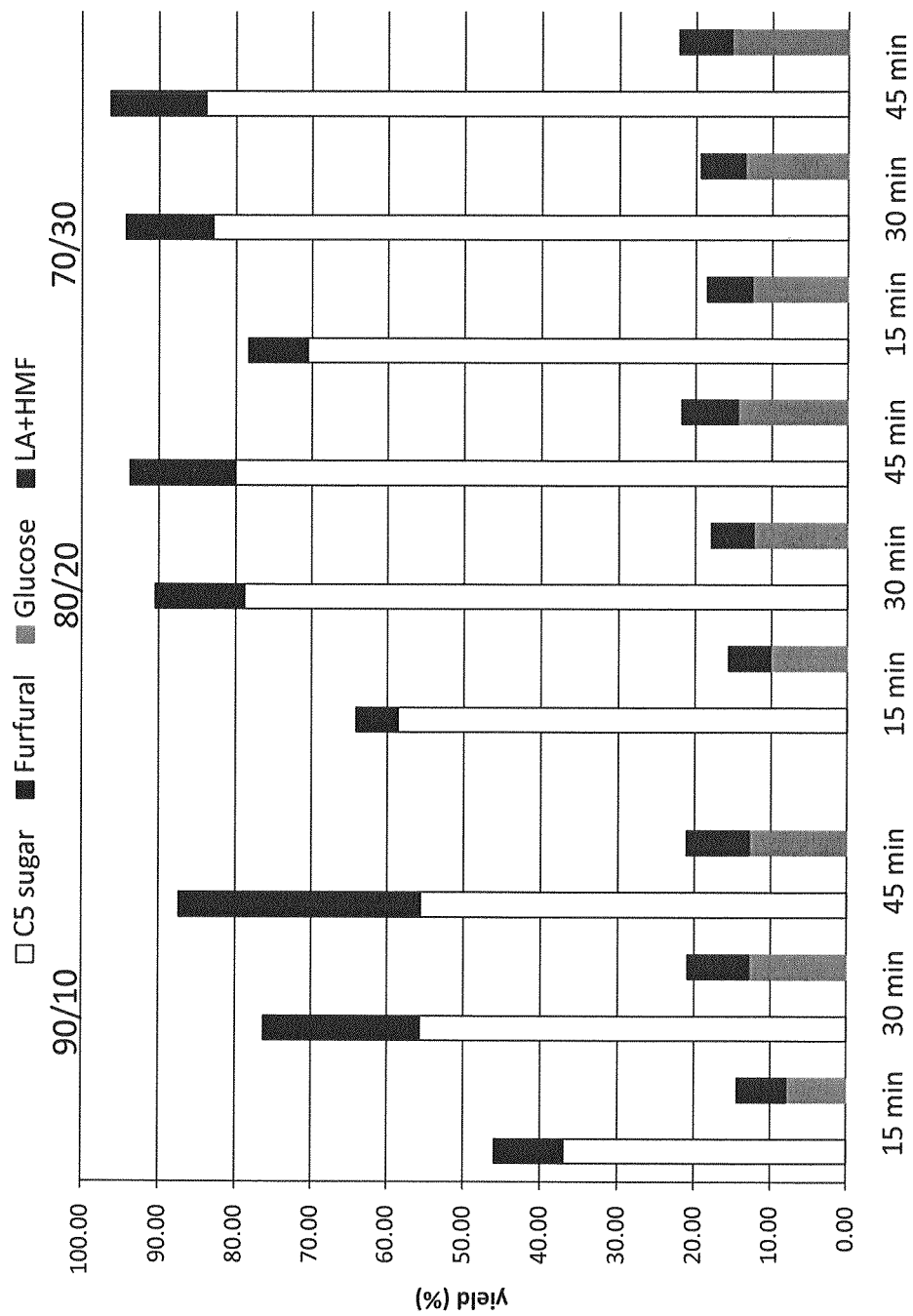
FIG. 6 is a histogram showing the results of a similar set of experiments as described for FIG. 5, except in this instance, the amount of water in the extraction solvent was varied (10%, 20%, and 30%). The reactant was 20 wt % corn cob particles; the extraction solvent contained 0.075 M $H_2SO_4$; reaction temperature was 130° C.

FIG. 6 presents the results of a similar set of experiments as described for FIG. 5, except in this instance, the amount of water in the extraction solvent was varied (10%, 20%, and 30%), along with the time of the extraction. The reactant was 20 wt % corn cob particles; the extraction solvent contained 0.075 M $H_2SO_4$; reaction temperature was 130° C. The histogram shown in FIG. 6 is organized in the same fashion as in FIG. 5. As shown in FIG. 6, similar yields were obtained at different water concentrations. At lower water concentrations, however, more furfural is produced. Approximately 20% of the C6 sugars are present as glucose, LA and HMF. The rest of the C6 sugars remain solid.

Figure 7:
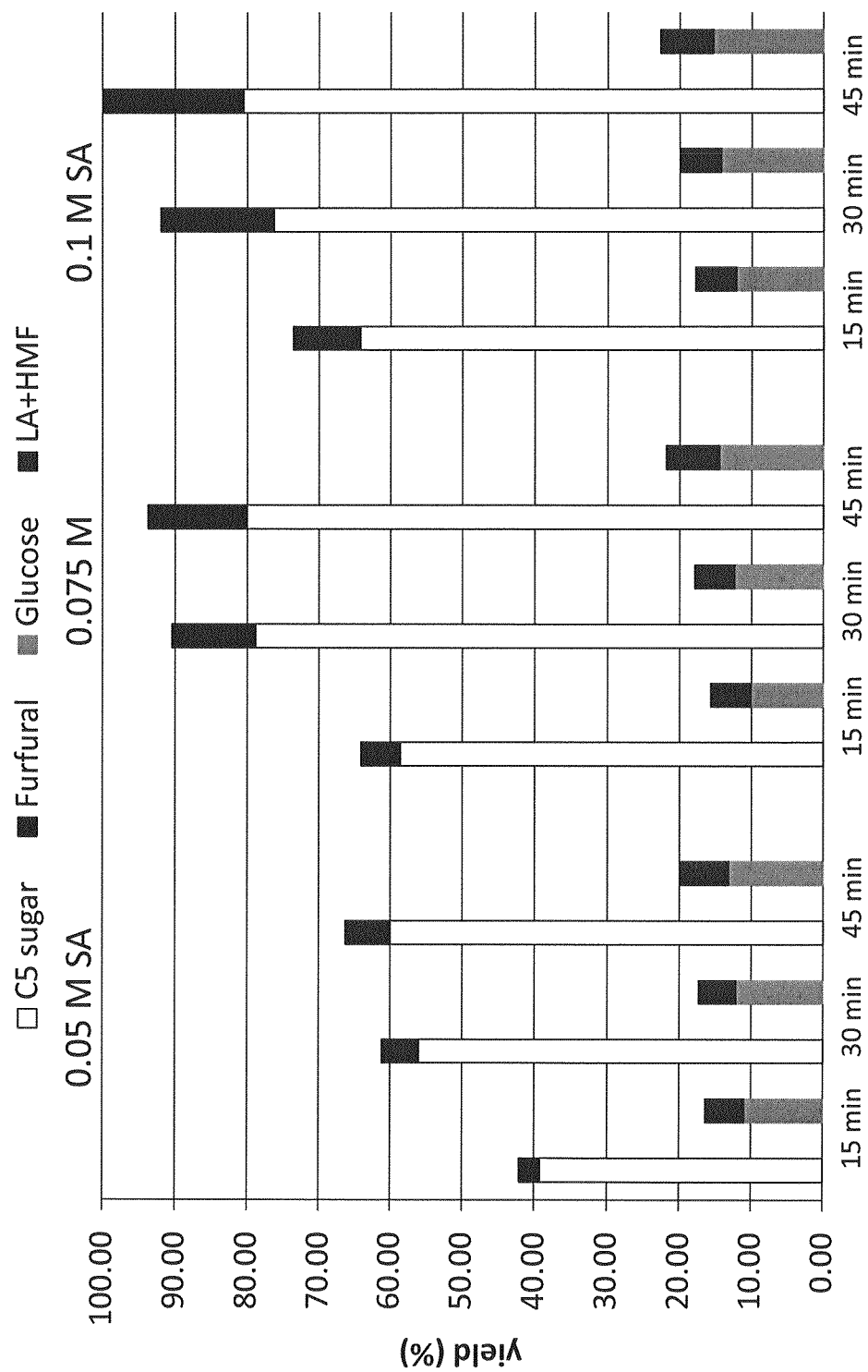
FIG. 7 is histogram showing the C5 sugar extraction efficiency as a function of the acid concentration and time of reaction. The biomass was 20 wt % corn cob particles; reaction temperature was 130° C.; the solvent was 80/20 GVL/water with varying amounts of sulfuric acid (SA)

FIG. 7 is another histogram showing the C5 sugar extraction efficiency as a function of the acid concentration and time of reaction. The biomass was 20 wt % corn cob particles; reaction temperature was 130° C.; the solvent was 80/20 GVL/water with varying amounts of sulfuric acid (SA) as noted in FIG. 7. The histogram shown in FIG. 7 is organized in the same fashion as in FIG. 5. As the results in FIG. 7 show, C5 sugars can be extracted at high yields at several different acidic conditions with minimal extraction of C6 sugars.

Figure 8:
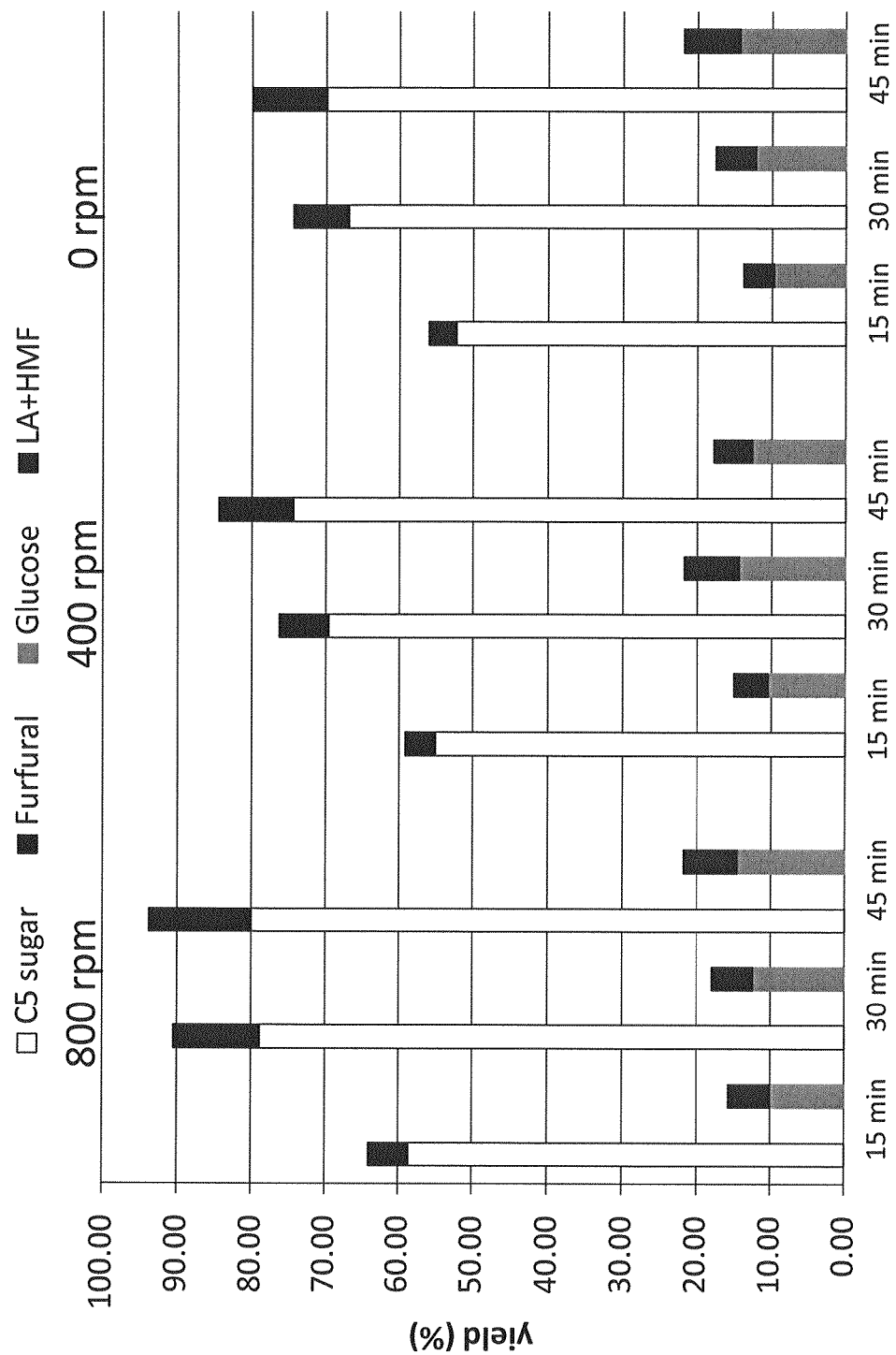
FIG. 8 is histogram showing the C5 sugar extraction efficiency as a function of the force used to mix the biomass and the extraction solvent (expressed as the rpms of the mixer 12 shown in FIG. 1D) and the time of the reaction. The biomass was 20 wt % corn cob particles in 0.075M sulfuric acid in 80/20 GVL/water. The reaction temperature was 130° C.

FIG. 8 is histogram showing the C5 sugar extraction efficiency as a function of the force used to mix the biomass and the extraction solvent (expressed as the rpms of the mixer 12 shown in FIG. 1D) and the time of the reaction. The biomass was 20 wt % corn cob particles in 0.075M sulfuric acid in 80/20 GVL/water. The reaction temperature was 130° C. The histogram shown in FIG. 8 is organized in the same fashion as in FIG. 5. FIG. 8 clearly shows that while vigorous mixing of the corn cobs with the liquid improves the results (see the data under "800 rpm" and "400 rpm"), mixing is not necessary to obtain satisfactory yield (see the data under "0 rpm").

Figure 9:
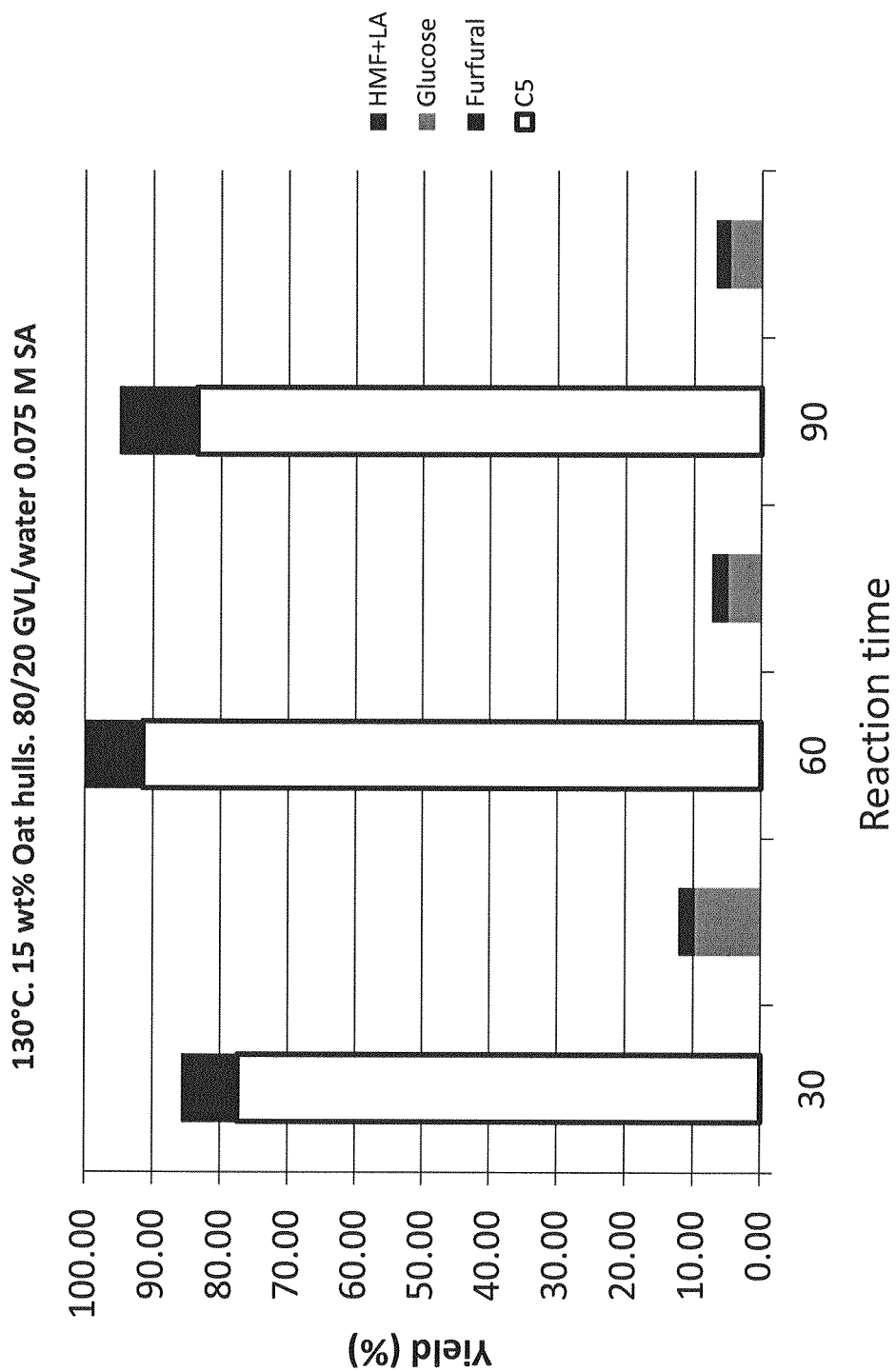
FIG. 9 is a histogram showing that similar extraction yields are obtained from other types of biomass, such as oat hulls. Reaction conditions: 15 wt % oat hulls with 0.075 M sulfuric acid in 80/20 GVL/water at 130° C. for the stated times.
Figure 10:
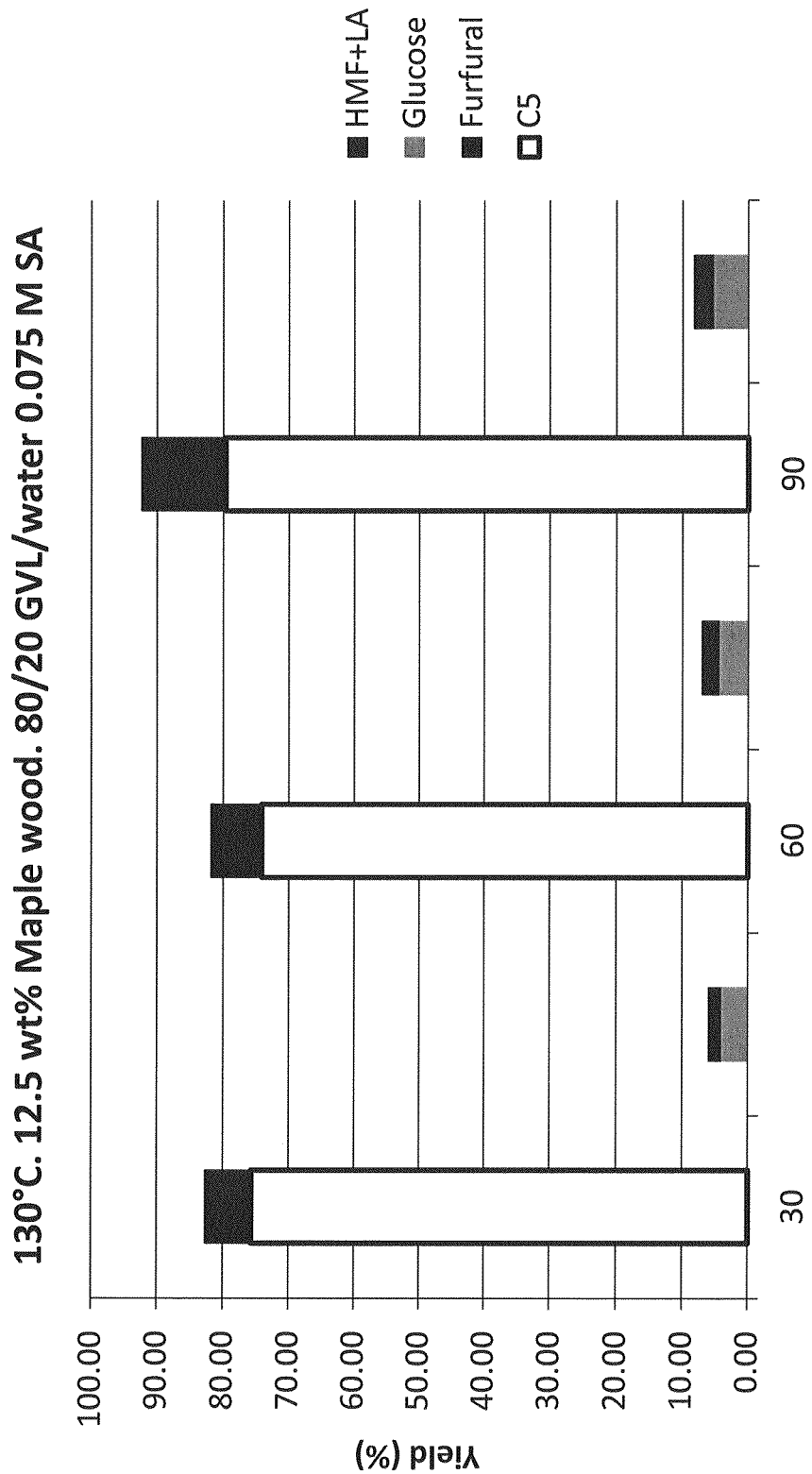
FIG. 10 is a histogram showing the results when using maple wood chips as the biomass. Reaction conditions: 12.5 wt % maple wood chips with 0.075 M sulfuric acid in 80/20 GVL/water at 130° C. for the stated times.

FIG. 9 is a histogram showing that similar extraction yields are obtained from other types of biomass, such as oat hulls. The results shown in FIG. 9 were generated by extracting 15 wt % oat hulls with 0.075 M sulfuric acid in 80/20 GVL/water at 130° C. for the stated times. FIG. 10 is a corresponding histogram showing the results when using maple wood chips as the biomass. The results shown in FIG. 10 were generated by extracting 12.5 wt % maple chips with 0.075 M sulfuric acid in 80/20 GVL/water at 130° C. for the stated times. With maple, good extraction yields were achieved but a lower solid/liquid ratio was used to ensure thorough mixing of the extraction solvent with the biomass.

Figure 11A:
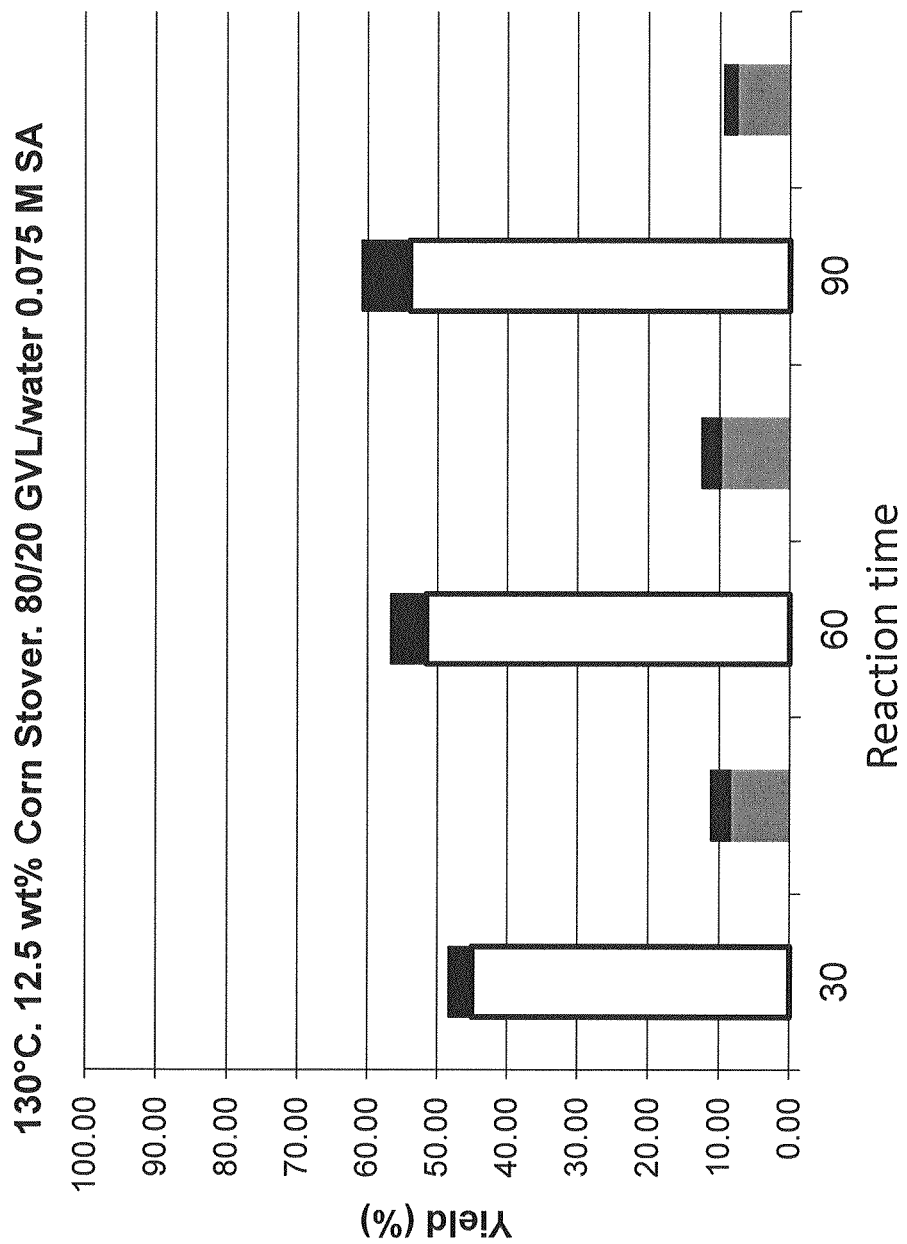
FIGS. 11A and 11B are similar to FIGS. 9 and 10, except corn stover was used as the biomass.
Figure 11B:
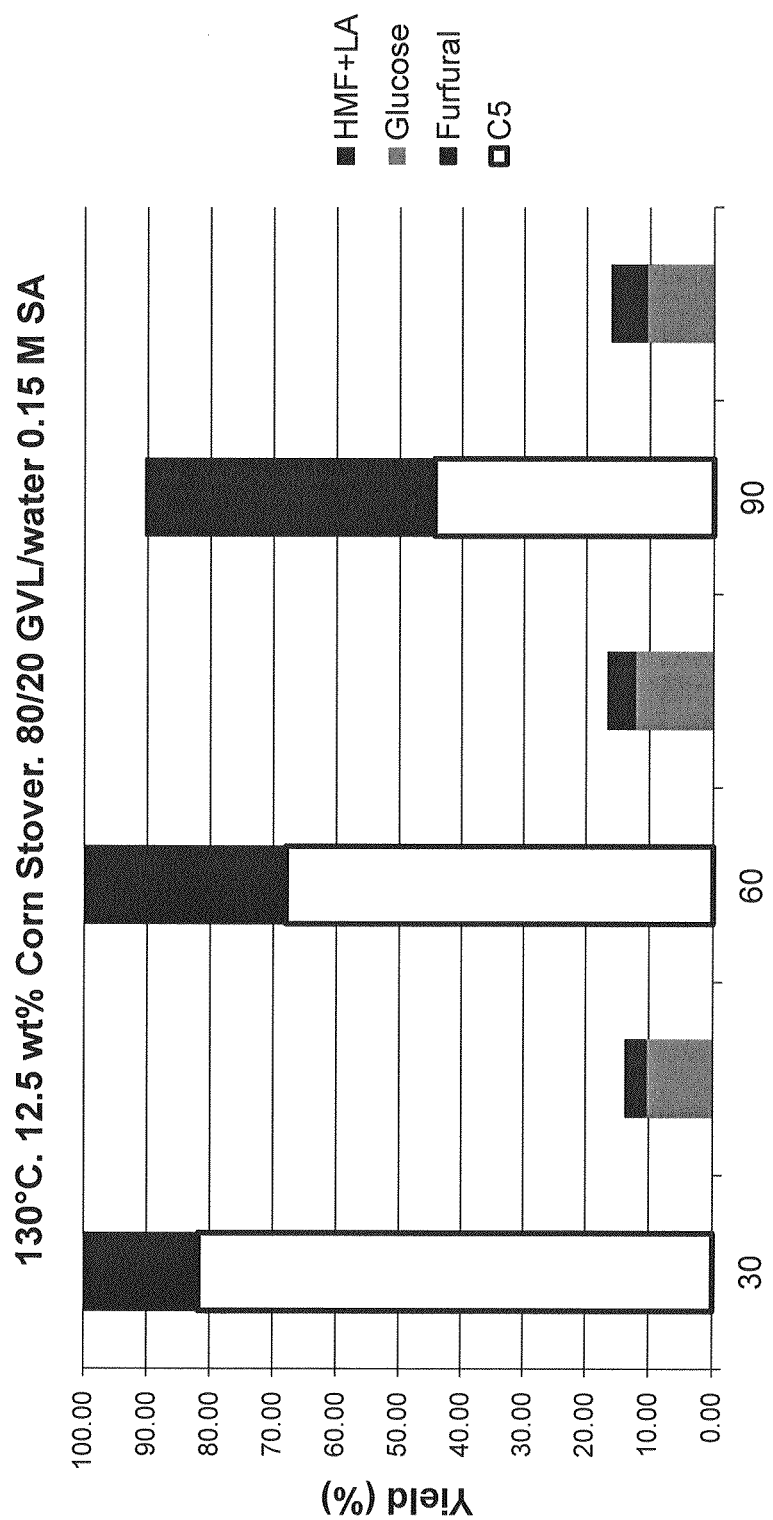
Figure 12:
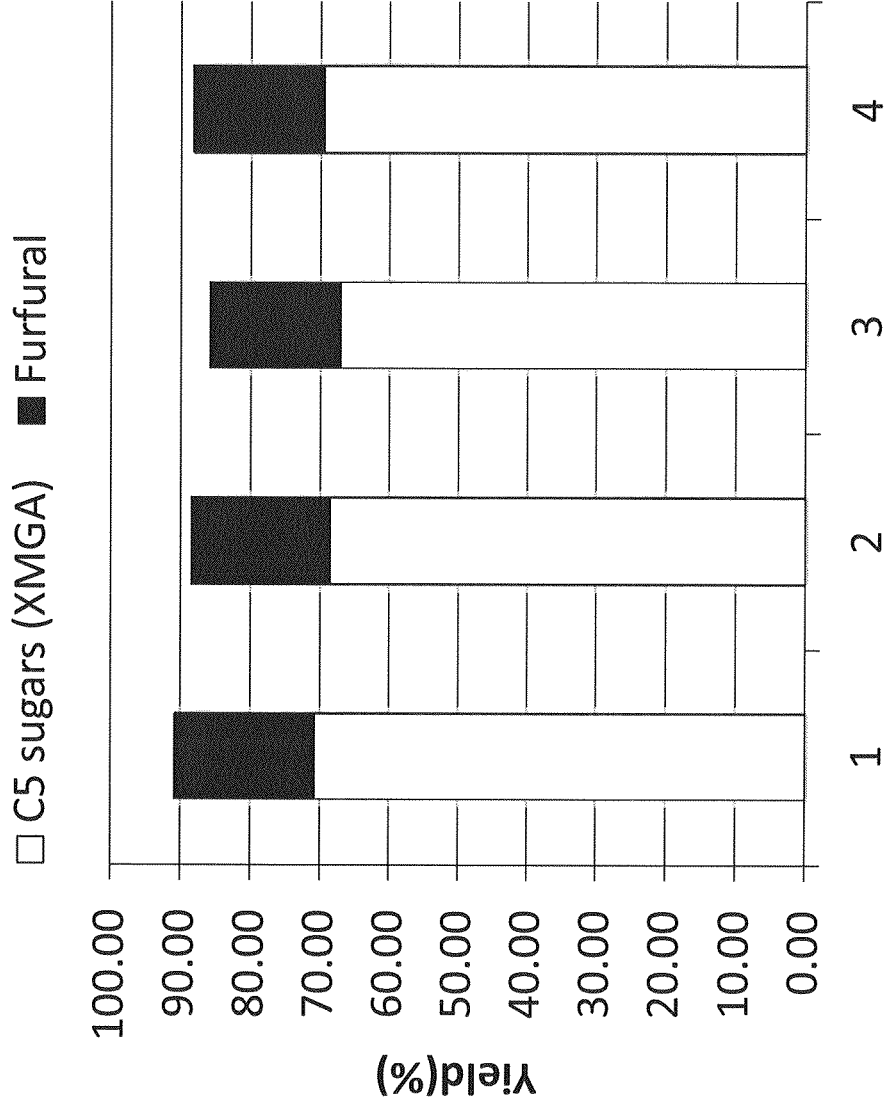
FIG. 12 is a histogram providing the yield of C5 sugars from quadruplicate runs of the same extraction as in FIG. 11B (12.5 wt % corn stover reacted with 0.15 M sulfuric acid in 80/20 GVL/water). XMGA=xylose, mannose, galactose, arabinose.

FIGS. 11A and 11B are similar to FIGS. 9 and 10, except corn stover was used as the biomass. In FIG. 11A, 12.5 wt % corn stover was reacted with 0.075 M sulfuric acid in 80/20 GVL/water. In FIG. 11B, 12.5 wt % corn stover was reacted with 0.15 M sulfuric acid in 80/20 GVL/water. As can be seen by comparing FIGS. 11A and 11B, both sets of conditions gave acceptable yields, but increasing the acid concentration gave markedly improved yields (nearly quantitative for the 30 min and 60 min C5 entries in FIG. 11B).

FIG. 12 is a histogram providing the yield of C5 sugars from quadruplicate runs of the same extraction as in FIG. 11B (12.5 wt % corn stover reacted with 0.15 M sulfuric acid in 80/20 GVL/water). The average yield of the four runs for total C5 sugar is about 87%. (XMGA=xylose, mannose, galactose, arabinose.) The xylose concentration of the liquid fraction was 11. 88 wt %, with >5 wt % furfural). Thirty-four (34) wt % of the raw biomass was retained as solids. The solid fraction accounted for about 80 wt % of the total glucose present in the raw biomass. Quite clearly, the histogram depicted in FIG. 12 demonstrates that the present method is very effective at quickly separating the C5 and C6 sugars very early in the processing of the raw biomass.

Figure 26:
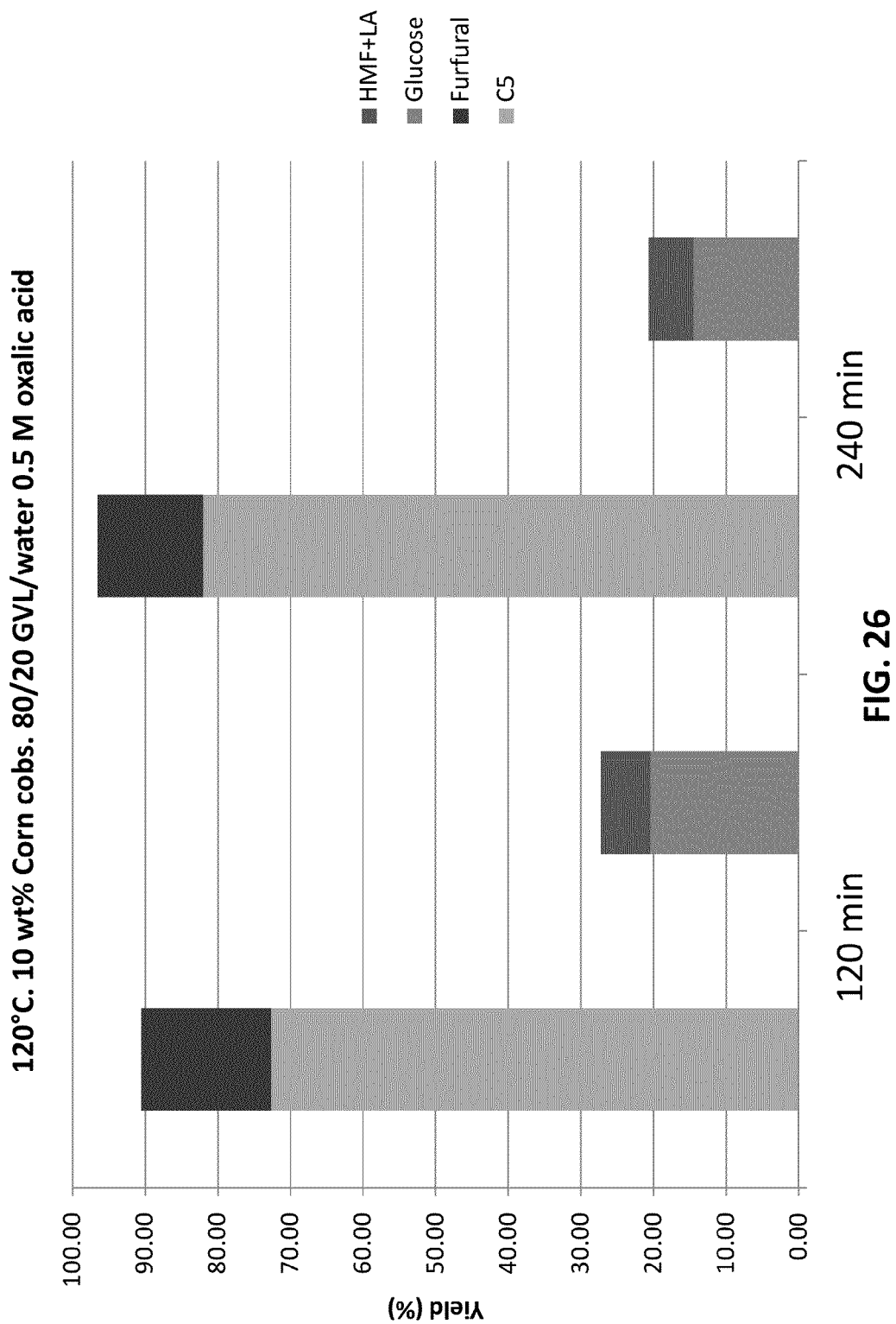
FIG. 26 is a histogram showing that similar extraction yields were obtained when using THF in the solvent system rather than GVL.

FIG. 26 is a histogram showing that similar extraction yields were obtained when using THF in the solvent system rather than GVL. As shown in the figure, the results obtained from several biomass types and conditions when using THF are similar to those obtained when using GVL. The results shown in FIG. 26 were generated by extracting 30 wt % corn cobs or 15 wt % corn stover with 0.15 M sulfuric acid in 70/30 THF/water at 130° C. for the 75 min. In both cases yields over 90% of C5 products (combined sugar, sugar oligomers and furfural) were obtained with minimal extraction of the C6 sugars.

Figure 27:
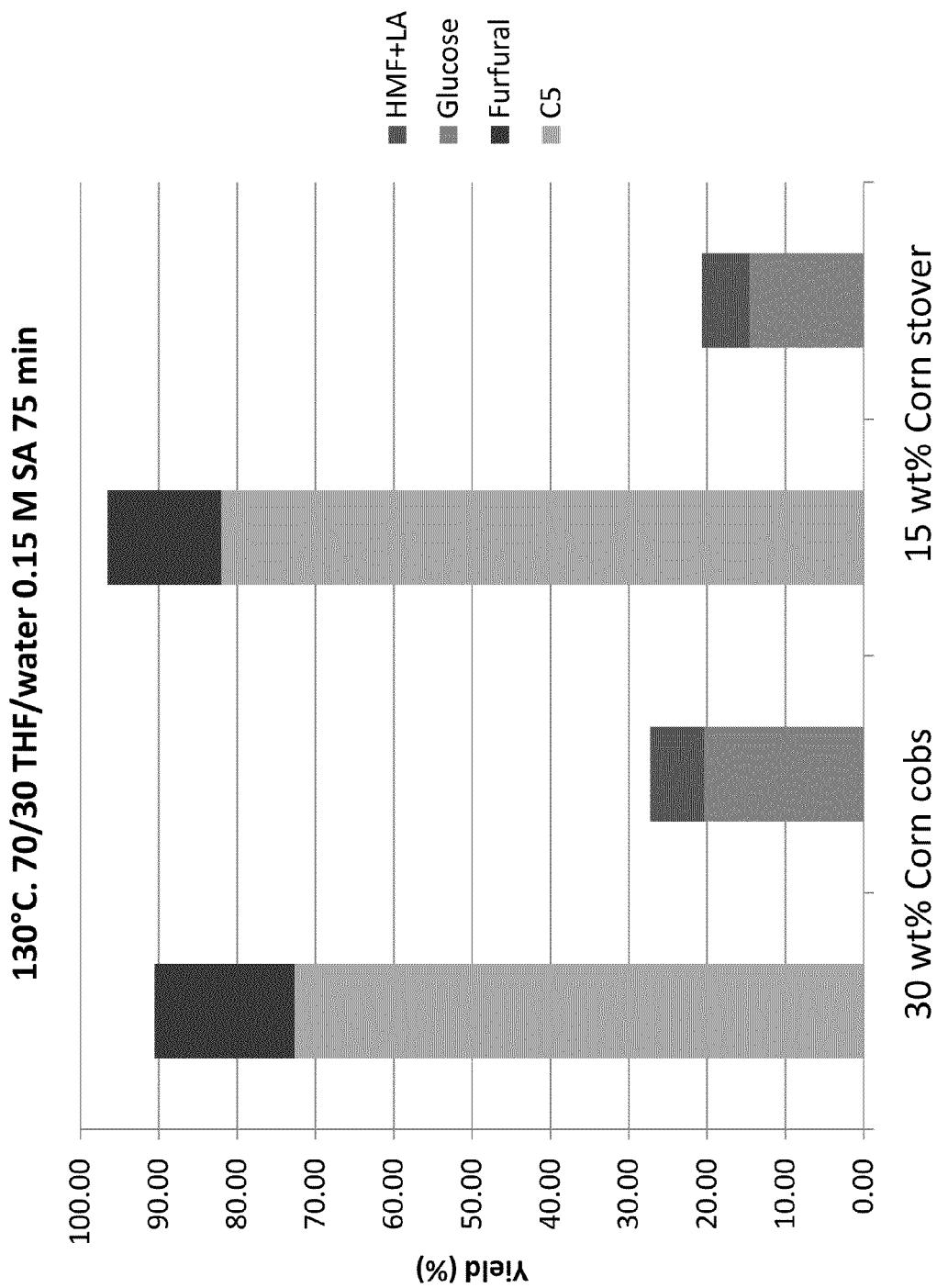
FIG. 27 is a histogram showing that similar extraction yields were achieved using an organic acid (oxalic acid in this instance) rather than a mineral acid.

FIG. 27 is a histogram showing that similar extraction yields were achieved using an organic acid (oxalic acid in this instance) rather than a mineral acid. In this case, the concentration of the acid has to be increased to account of for the lower strength of the organic acid as compared to the mineral acid. The results shown in FIG. 27 were generated by extracting 10 wt % corn cobs with 0.5 M oxalic acid in 80/20 GVL/water at 120° C. for the stated time. Yields over 80% of C5 products (combined sugar, sugar oligomers and furfural) were obtained with minimal extraction of the C6 sugars.

Table 4 provides a summary of the yields that were obtained in the various testing completed to date.

TABLE 4

Summary of Yields and Sugar Recovery:

| Reaction conditions (GVL/water, SA = sulfuric acid) | Additions of biomass/ amount (wt %) | Total C6 yield (%) | Total C5 yield (%) | Furfural (g furfural/ g GVL) | Solids recovered (% of initial biomass) |
|---|---|---|---|---|---|
| Corn stover 80/20 0.15M SA 130° C., 30 + 90 min | 2/(12.5) | 30.64 | 93.2 | 4.5 | 30.60% |
| Corn stover 70/30 0.15M SA 130° C., 60 min | 1/(20)5 | 14.73 | 98.25 | 5.3 | xxx |
| Maple wood 80/20 0.075M SA 130° C., 60 + 60 min | 2/(12.5) | 13.4 | 87.74 | 3.7 | 59.12% |
| Oat hulls 80/20 0.075M SA, 130° C., 60 + 90 min | 2/(15) | 16.2 | 99.82 | 8.0 | 39.15% |
| Corn cobs 80/20 0.075M SA 45 + 60 min | 2/(20) | 23.67 | 86.55 | 11.4 | 33.75% |
| Corn cobs 70/30 0.075M SA 45 + 60 min | 2/(20) | 22.86 | 97.64 | 12.8 | 28.95% |

Figure 13:
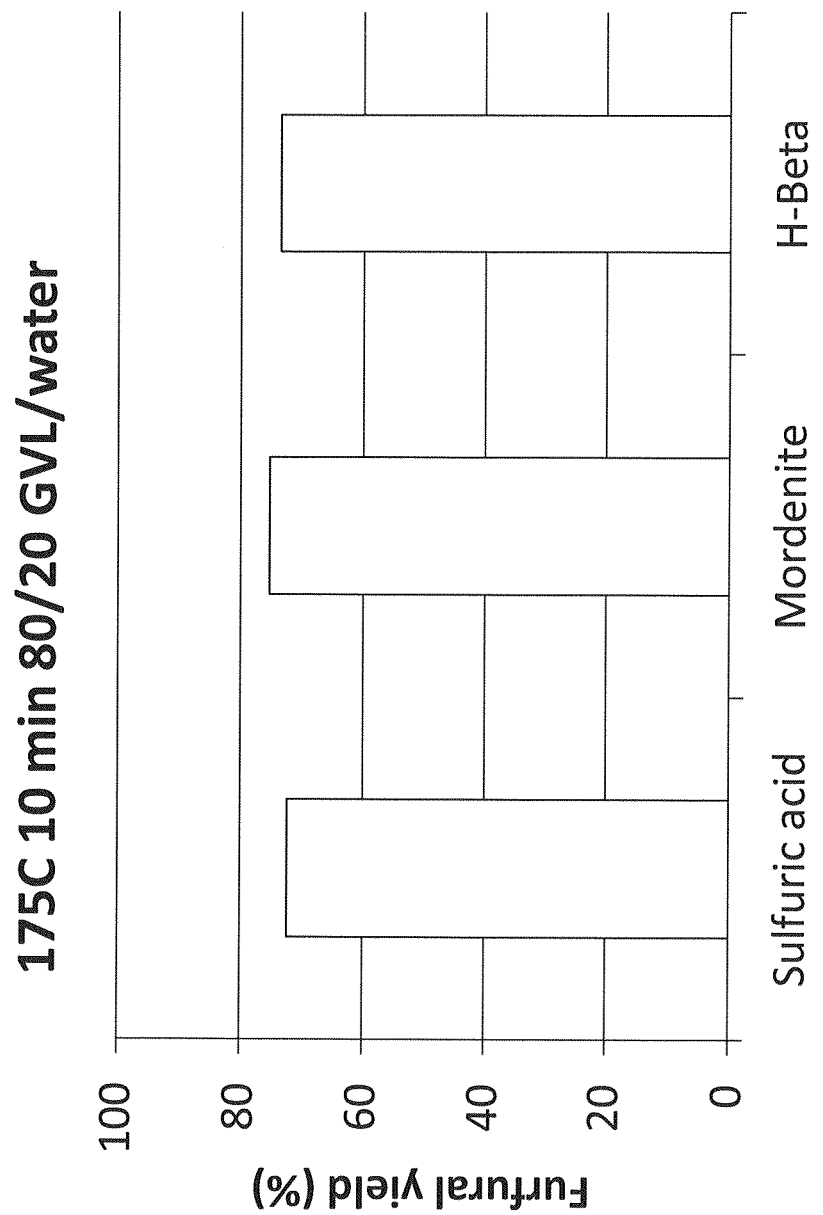
FIG. 13 is a histogram depicting furfural yield for liquid fractions heated to 175° C. for 10 minutes in 80/20 GVL/water over the stated catalysts.

A primary advantage of the pre-treatment/extraction method is that the resulting xylose solution can be converted into furfural and high concentrations (>5.5 wt %) at high yields, using either homogeneous or heterogeneous catalysts. In short, there is no need to separate the C5 sugars from the GVL-containing extraction solvent prior to producing the furfural. After the initial extraction and separation of the liquid and solid fractions, the conversion of the xylose (present in the liquid fraction) to furfural can proceed in the absence of any intervening processing of the liquid fraction. See, for example, FIG. 13, which is a histogram depicting furfural yield for liquid fractions heated to 175° C. for 10 minutes in 80/20 GVL/water over the stated catalysts. Sulfuric acid is a homogeneous catalyst. Mordenite is a heterogeneous catalyst (a zeolite mineral). H-Beta is a also a heterogeneous catalyst (a zeolite). In all three reactions, furfural yield exceeded 70%.

Figure 14:
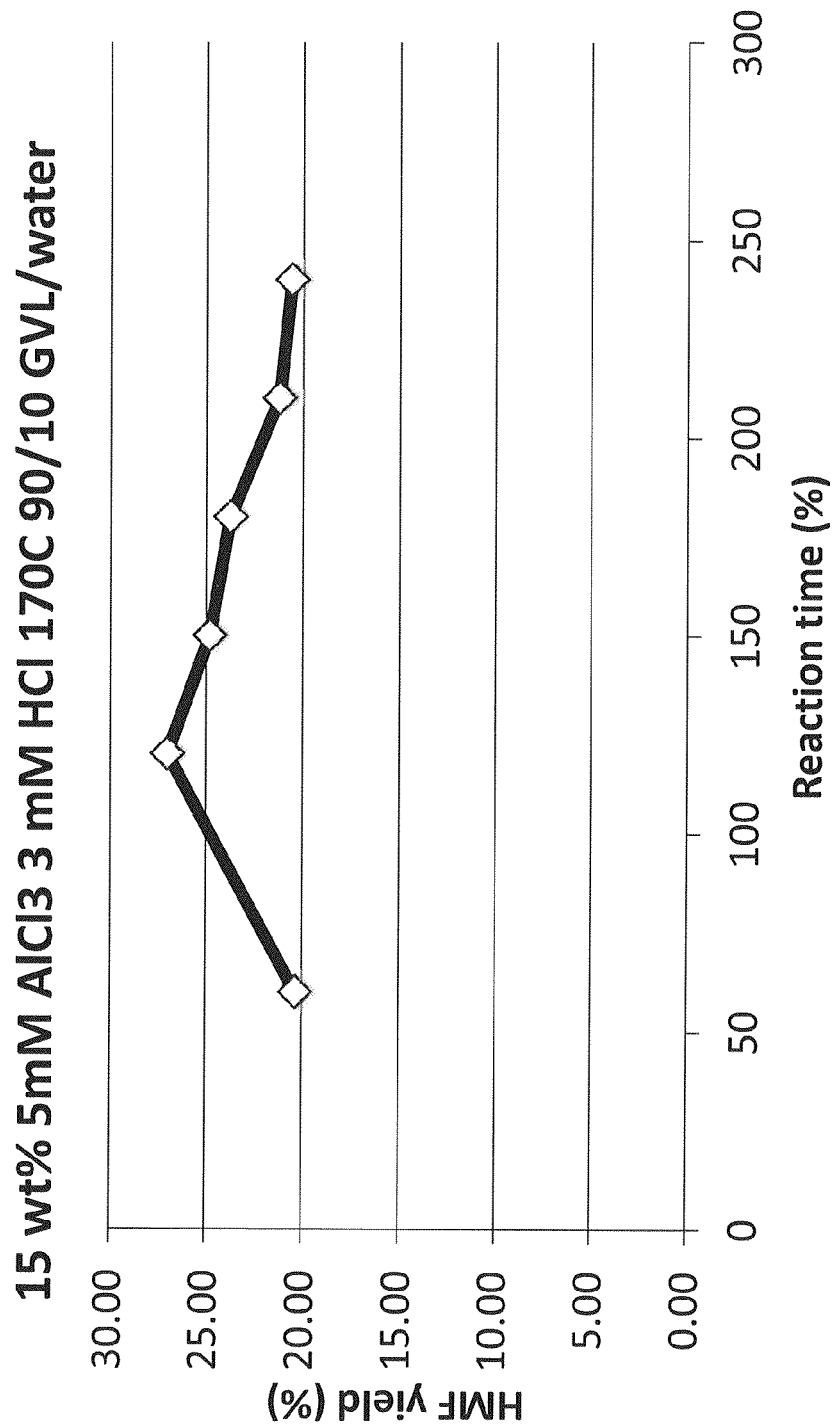
FIG. 14 is a graph showing that without any intervening processing steps, the C6 solids can be converted (upgraded) into HMF solutions having concentrations >3.2 wt %. HMF yield at all points tested fell between about 20% and about 26%.

Similarly, there is no need to separate the C6 sugars when upgrading them to HMF, LA, or GVL itself as shown in FIG. 14. Without any intervening processing steps, the C6 solids can be converted into HMF at concentrations >3.2 wt %. To generate the data presented in FIG. 14, the solid fraction after extraction with GVL/water/SA as described previously was reacted at 15 wt % with 5 mM $AlCl_3$ and 3 mM HCl in 90/10 GVL/water at 170° C. for the stated times. HMF yield at all points tested fell between about 20% and about 26%.

Figure 15:
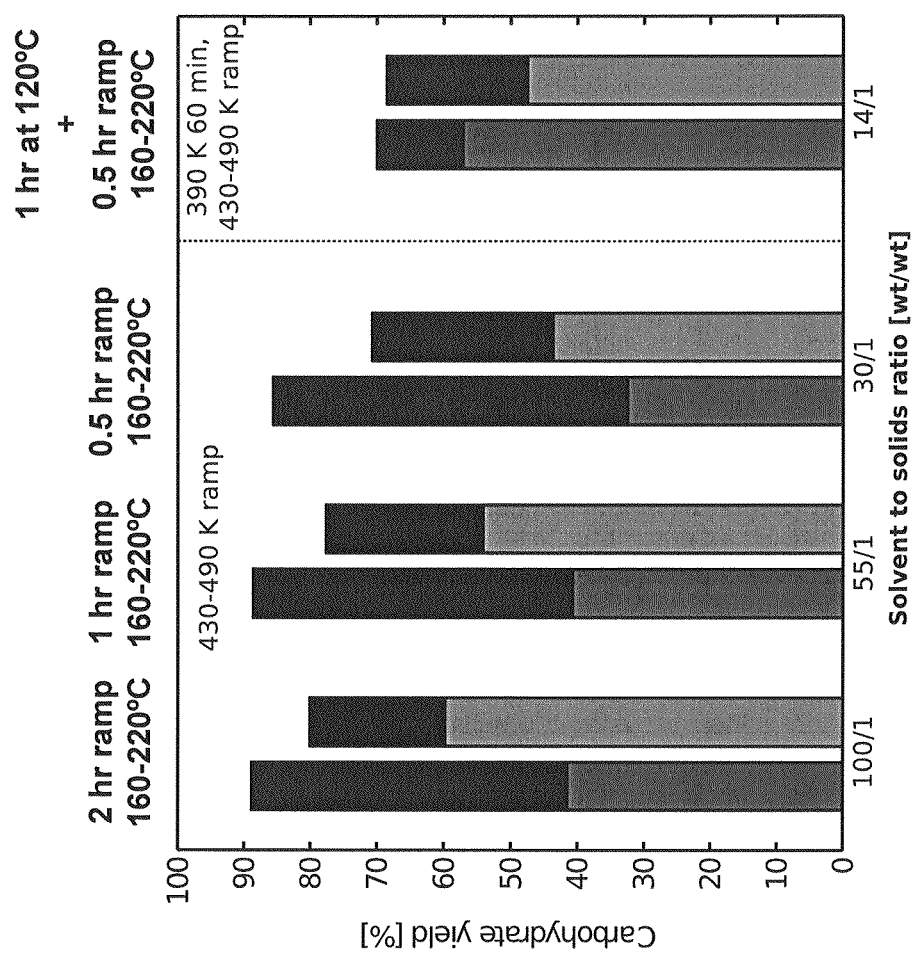
FIG. 15 is a histogram depicting the effect of ramping the extraction temperature at various solvent-to-solids ratios. Reaction conditions: 80/20 GVL/water extracting solvent and corn stover as the biomass reactant. The X-axis shows the solvent-to-solids ratio (wt/wt) and the Y-axis shows the total carbohydrate yield. Liquid fraction yield is the left bar in of each pair of bars; solid fraction yield is the right bar in each pair.

Notably, both the liquid fraction and the solid fraction can be converted into sugars, thereby increasing by at least 7-fold the concentration of these useful sugars. For example, FIG. 15 is a histogram depicting the effect of ramping the extraction temperature at various solvent-to-solids ratios. The data in FIG. 15 were generated using an 80/20 GVL/water extracting solvent and corn stover as the biomass reactant. The X-axis shows the solvent-to-solids ratio (wt/wt) and the Y-axis shows the total carbohydrate yield. (Liquid fraction yield is the left bar in of each pair of bars; solid fraction yield is the right bar in each pair.) As shown in the figure, very acceptable yields are obtained a host of different solvent-to-solids ratios and temperature ramp profiles (160° C. to 220° C. over a course of 0.5 hr, 1.0 hr, and 2.0 hr). The far-right pair of bars depicts the results for a non-linear temperature ramp of 1 hr at 120° C., followed by a 0.5 hour continuous ramp from 160° C. to 220° C. This particular experiment also had a very low 14:1 solvent-to-solids ratio. Again, the yields are quite favorable, even when a relatively small volume of solvent is used.

Figure 16:
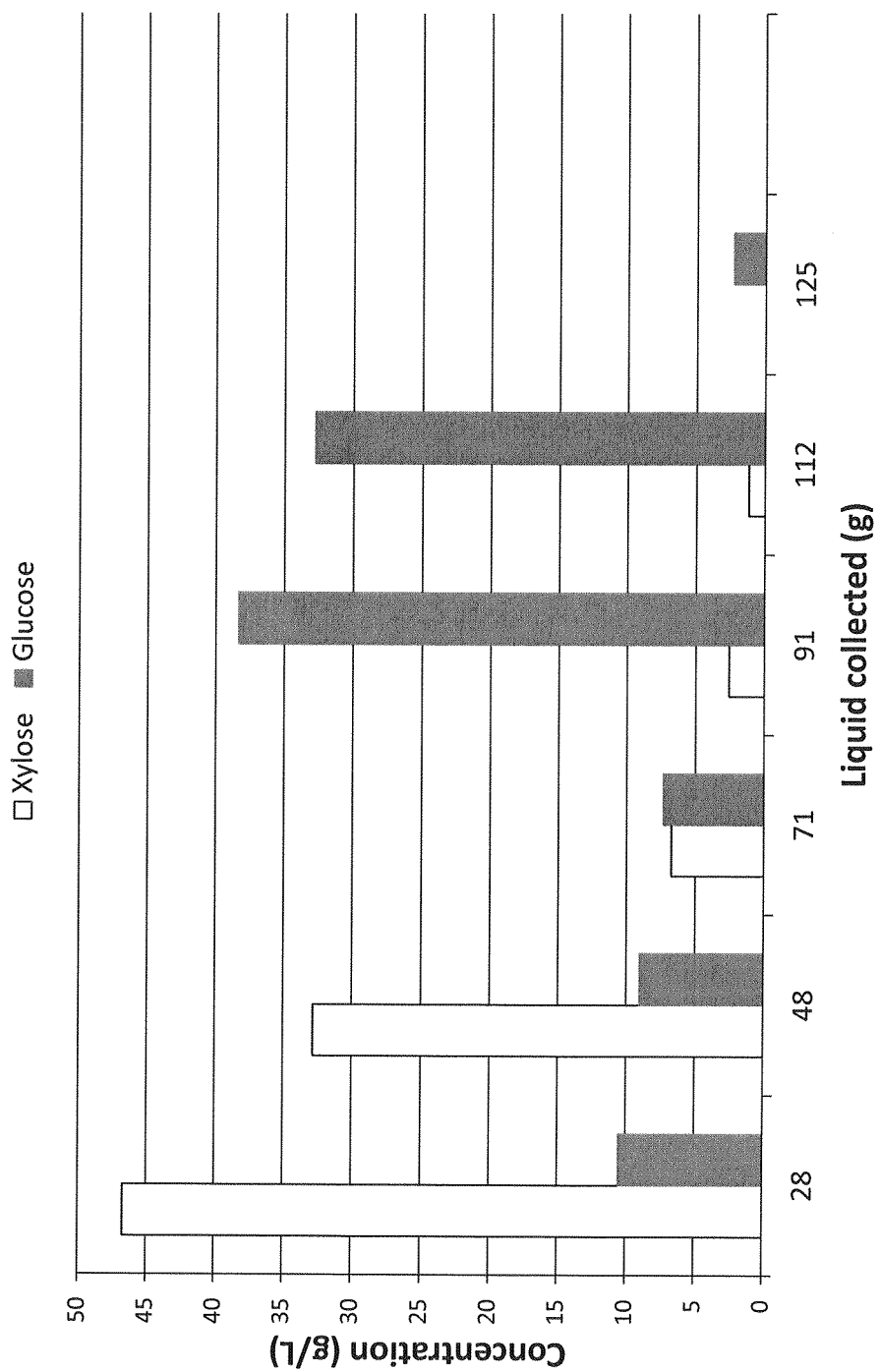
FIG. 16 is a histogram depicting the xylose and glucose concentrations of the extraction solvent used for the far-right experiment in depicted in FIG. 15 as a function of the volume of eluant collected.

The extraction solvent used for the far-right experiment in FIG. 15 was collected in eluant fractions (the reaction was run continuously) and each fraction was tested for its xylose concentration (a C5 sugar) and its glucose concentration (a C6 sugar). The results are shown in FIG. 16. As can be seen from the histogram in FIG. 16, the first two fractions (at 28 g and 48 g) contain overwhelming concentrations of xylose as compared to glucose. Then, in the later fractions, glucose comes to dominate (because the xylose has been preferentially removed from the biomass in the early going). Again, the in FIG. 16 was generated using corn cobs, at a solvent-to-solids ratio of 14:1, with a non-linear temperature ramp of 1 hr at 120° C., followed by a 0.5 hour continuous ramp from 160° C. to 220° C.

Figure 17:
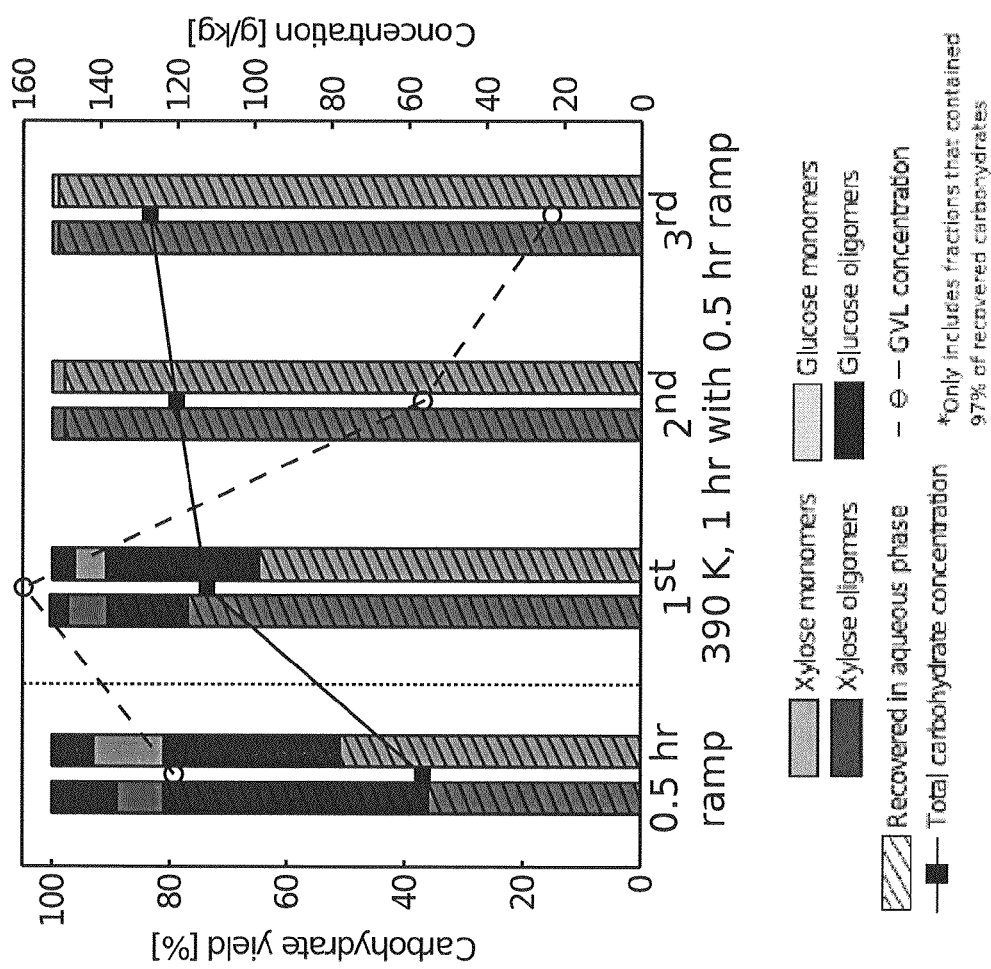
FIG. 17 is a composite histogram and graph depicting carbohydrate yield (%) on the left-hand Y-axis, carbohydrate concentration (g/kg) on the right-hand Y-axis, with the temperature ramp data recorded on the X-axis.

FIG. 17 is a composite histogram and graph depicting carbohydrate yield (%) on the left-hand Y-axis, carbohydrate concentration (g/kg) on the right-hand Y-axis, with the temperature ramp data recorded on the X-axis. Ninety percent (90%) of the carbohydrates present in the raw biomass can be recovered at concentrations of 127 g/L when precipitated from the extraction solvent using, for example, $CO_2$.

EXAMPLES

The following examples are presented solely to provide a more complete description of the method disclosed and claimed herein. The examples do not limit the scope of the method in any fashion.

Flow-Through Reactions:

A schematic representation of the flow-through reaction system is given in FIG. 1B. Corn stover was obtained from the Great Lakes Bioenergy Center (GLBRC, Madison, Wis.), maple wood was obtained from Mascoma (Hanover, N.H.), and loblolly pine was obtained from the Forest Products Laboratory (Madison, Wis.). The compositions of these biomass feedstocks are given in Table 5. Approximately 2.5 g of biomass was mixed with 5 g of silicon dioxide fused granules (Sigma-Aldrich, St. Louis, Mo.) and placed in the heated zone of the flow-through reactor between two beds of silica granules separated by quartz wool plugs (Grace-Davison, Columbia, Md.). The flow-through reactor was comprised of a 35 cm ½ in diameter stainless steel tube (TW Metals, Los Angeles, Calif.) with corresponding stainless steel valves and fittings (Swagelok, Solon, Ohio). The heated zone of the reactor was fitted between two aluminum blocks placed within an insulated furnace (Applied Test Systems, Butler, Pa.). A type-K thermocouple (Omega Engineering, Stamford, Conn.) was placed at the reactor wall and was used to monitor and control the reactor temperature using a 16A series controller (Love Controls, a subsidiary of Dwyer Instruments, Michigan City, Ind.). Solvent was flowed through the system using an HPLC pump (Series 1, Lab Alliance-brand, Waters, Milford, Mass.). Pressure was maintained constant at 300 psi by flowing helium (Airgas, Radnor, Pa.) in the headspace of the liquid collector through a back-pressure regulator (1500 PSI, Tescom, a subsidiary of Emerson Process Management, Elk River, Minn.). At the start of the reaction, dry biomass was heated to 423 K in flowing helium using a 20 min ramp. The temperature was allowed to equilibrate between 423 and 433 K for 3 min, after which solvent was flowed through the biomass at a rate of 2 ml/min, while a 0.5 to 2-hour linear temperature ramp was applied between 430 and 490 K. The resulting flow-through liquid was sampled approximately every 5 min by draining the liquid collector.

TABLE 5

Compositions of corn stover, maple wood and loblolly pine used in this study.

| | Glucan [wt %] | Xylan [wt %] | Klason lignin [wt %] |
|---|---|---|---|
| Corn stover | 35.1 | 22.2 | 16.2 |
| Maple wood | 41.9 | 19.3 | 24.9 |
| Loblolly pine | 38.8 (11.8)$^a$ | 5.5 | N.D. |

$^a$Mannan for loblolly pine was quantified and is given in parentheses.

To achieve higher solid loading experiments, 7.5 g of corn stover along with 30 g of 80 wt % GVL or 80 wt % THF, 20 wt % water containing 150 mM $H_2SO_4$ were loaded into two 60 ml pressure tubes (Ace Glass, Vineland, N.J.) and placed into an oil bath heated to 390 K with an Isotemp digital stirring hotplate (Fisher Scientific, Waltham, Mass.). The mixture was stirred by a magnetic stir bar in the reactor at 500 rpm. In the case where maple wood was used in place of corn stover, the solution only contained 50 mM $H_2SO_4$ due to the lower acid neutralization potential of the wood. The resulting mixture was filtered with the filtrate taken as the first liquid fraction, and the unwashed solids placed in the flow-through reactor, where the same protocol as that described above was followed using a 0.5 hr temperature ramp. Yields were calculated based on the liquid removed during filtration and the liquid collected from the flow-through reactor.

X-ray Diffraction (XRD) of Acid-Treated Cellulose:

One half of a gram (0.5 g) of microcrystalline cellulose powder (Sigma-Aldrich) was added to a 10 ml thick-walled glass reactor (Grace Davison) along with 5 g of solvent (either 80 wt % GVL and 20 wt % water or pure water, both with 5 mM $H_2SO_4$). The reactor was then placed in an oil bath heated with an Isotemp digital stifling hotplate (Fisher Scientific), with the mixture being stirred by a magnetic stir bar in the reactor at 850 rpm. Reactors were cooled at specific reaction times by placing the them in an ice slurry.

XRD of the washed cellulose solids that remained after reaction was performed in a D8 Discover Discover X-ray diffractometer (Bruker, Billerica, Mass.) using CuKα radiation generated at a voltage of 50 kV and a current of 1 mA. Scans were obtained from 2θ=8° to 45° with 12-degree steps and 90 sec per step. The crystallinity index (CrI) was calculated using the formula given below (23, 24) after normalizing across signals.

$$CrI = \frac{I_{002} - I_{AM}}{I_{002}}$$

where $(I_{002}-I_{AM})$ is the signal for the crystalline portion of cellulose and $I_{002}$ is the signal for the total intensity at the location of the crystalline peak portion of cellulose, which in this case was taken at 2θ=22.2° (FIG. 19C). $I_{AM}$ is the base of the crystalline peak, which is considered to be the contribution by the amorphous cellulose fraction and in this case is taken at 2θ=18.2°.

Aqueous Phase Separation Using NaCl Addition:

A given amount of sodium chloride (Sigma-Aldrich) was added to the liquid solutions resulting from flow-through experiments using GVL/water mixtures to create a separate aqueous phase. The resulting solutions were repeatedly shaken and sonicated in a sonication bath (model FS28, Fisher-Scientific) until no solids were visible. The mixtures were then centrifuged at 4500 rpm for 4 min in a Sorvall ST16 centrifuge (ThermoFisher Scientific, Waltham, Mass.). The heavier aqueous phase was removed using a syringe and needle to measure its mass, after which the compositions of both phases were analyzed.

Aqueous Phase Separation Using $CO_2$ Extraction:

10 g of the solution resulting from flow-through experiments using corn stover 80/20 GVL/water mixtures and a 30 min ramp was loaded into the into a 42 ml vessel. The vessel was made with a ½ in stainless steel tube, with corresponding stainless steel fittings, ball valves and needle valves (Swagelok). The inner volume between the lower ball valve and needle valve was 0.6 ml. Once closed, the vessel was pressurized to 1100 psi using a high-pressure syringe pump connected to a $CO_2$ siphon tank (Airgas). The reactor was allowed to equilibrate for 10 min, re-pressurized to 1100 psi and again equilibrated for 20 min. Each time a sample was taken from the bottom of the vessel, the lower ball valve was opened with the needle valve closed; the ball valve was then closed and liquid was collected by opening the needle valve. Following this step, the vessel was re-pressurized to 1100 psi and allowed to equilibrate for 10 min before another sample was taken. Each sample was analyzed, and subsequent samples were defined as being in the aqueous phase only if said samples contained a lower GVL concentration than that of the feed. All mass balances closed between 90 and 99%. Yields in each phase were normalized to the total amount of product recovered.

Monomer Production:

After processing the biomass, the oligomers present in the liquid were converted into monomers to facilitate the analysis. In the figures, all the oligmers present are reported as monomers. This was done by diluting the liquid 10x with 4 wt % sulfuric acid in water and processing for 1 hour at 120° C.

Oligomer depolymerization reactions were carried out in 5 ml thick-walled glass reactors (Supelco, a division of Sigma-Aldrich) with a magnetic stirrer. Approximately 2.5-3 g of aqueous solution resulting from separation of the aqueous phase by addition of salt to GVL/water or by $CO_2$ extraction was placed in the reactor. For more concentrated solutions resulting from a 30 min temperature ramp, 25 mmol/$g_{solution}$ of sulfuric acid was added by supplementing 25 mg of a 2.5 mol/g $H_2SO_4$ solution. The glass reactor was heated and stirred using a magnetic stir bar and an oil bath at 413 K placed on an Isotemp digital stirring hotplate set at 800 rpm (Fisher Scientific). Reactions were stopped at specific times by placing the reactors in an ice slurry.

Furan Production:

One hundred millimolar (100 mM) of $AlCl_3$ (Sigma-Aldrich) was added to 1.5 g of aqueous solution separated from the 80/20 GVL/water solution derived from corn stover using a 2 hr temperature ramp by addition of salt, and this aqueous solution was mixed with 3 g of SBP (Alfa-Aesar, a subsidiary of Johnson Matthey, Ward Hill, Mass.) in a 10 ml thick-walled glass reactor (Grace Davison). To begin the reaction, the resulting mixture was placed in an oil bath heated with an Isotemp digital stirring hotplate (Fisher Scientific). This hotplate was used to stir a magnetic stir bar in the reactor at 1200 rpm. Reactors were cooled at specific reaction times by placing the them in an ice slurry.

Feed Preparation for Biological Upgrading:

Multiple flow-through reactions using 80/20 GVL water and either a 0.5 hr temperature ramp or a step at 390 K for 1 hr followed by the 0.5 hr temperature ramp were run as described above, and the feed was collected excluding the first volume fraction of 10 g which typically contributed to only 0-2% of carbohydrate yield. The resulting feed from four runs was combined and rendered biphasic by addition of 12 wt%$_{aq}$ NaCl. To produce monomers, in the case where just the 0.5 hr ramp was used, 25 mmol $H_2SO_4$ per g of solution was added to the resulting the aqueous phase, which was then heated to 413 K for 100 min. This solution is referred to as the NaCl-separated feed.

The resulting feed from four runs was combined and its GVL was extracted using $CO_2$ by subsequent additions of 57 g solution in a 240 ml extraction vessel at 1100 psi of $CO_2$ (which corresponds to the same mass-to-volume ratio and same pressure as those used for the 42 ml extraction vessel described above). Besides the extraction vessel volume, all other equipment and operations were identical to those described for the 42 ml vessel. Once again for monomer production, in the case where just the 0.5 hr ramp was used, 25 mmol/g$_{solution}$ $H_2SO_4$ was added to the aqueous phase (no acid supplementation was necessary when an initial treatment at 390 K for 1 hr in the presence of 50-150 mM $H_2SO_4$ was performed). The solution was then heated to 413 K for 100 min and was extracted twice more using $CO_2$, by addition of 34 ml, and subsequently 22 ml of aqueous solution to the 240 ml extraction vessel (the resulting concentrations for the solution obtained using the 0.5 hr temperature ramp are shown in FIG. 17). Once again, during these two extractions, besides the proportional increase in vessel size and loading, all other equipment and operations were identical to those described for the 42 ml vessel. This solution is referred to as the $CO_2$-extracted feed.

Biological Upgrading to Fatty Acids:

The salt-separated feed was adjusted to pH 5.0 through the addition of 10 M KOH (Sigma). The final pH was checked using a pH meter (Mettler-Toledo, Columbus, Ohio). The medium was then centrifuged at 4000 rpm for 20 minutes in an Allegra X-15R Centrifuge (Beckman-Coulter, Brea, Calif.), and the supernatant filter was sterilized using a 0.22 μm syringe filter (VWR International, Radnor, Pa.). FFA production was performed in 250 ml shake flasks using *E. coli* TY05 (3) in 50 ml of a 1:10 dilution of salt extracted feed in a phosphate limited media described previously (3). Shake flask production and analysis of FFAs were performed as described previously (3).

Biological Upgrading to Ethanol:

The salt-separated feed was pH adjusted and filter sterilized as outlined above. Fermentation media were prepared in 5 ml volumes with 3.54 ml water, 0.83 ml salt separated feed, 0.5 ml 10x Yeast Nitrogen Base without Amino Acids, 0.05 ml 100x Casamino Acids and 0.08 ml of 25 wt % Tween 80 (Sigma) for a final feed dilution of ⅙. A single colony of wild type *S. cerevisiae* PE2 (provided by Tom Jeffries, UW-Madison) on YPD agar (Fisher Scientific) was used to inoculate an overnight of 5 ml YPD broth in glass culture tubes (20×150 mm, Fisher Scientific) at 30° C. and 250 rpm agitation in an I 26 shaker (New Brunswick Scientific, a subsidiary of Eppendorf, Enfield, Conn.). The fermentation media were inoculated to an $OD_{600}$ of 0.01 in anaerobic hungate tubes (16×125 mm, Fisher Scientific) from the YPD overnight using a Spectronic 20 spectrophotometer (Milton Roy Company, Warminster, Pa.) for optical density (OD) measurements. The tubes were sparged with $N_2$ (Airgas) for 3 minutes, and then incubated for 32 hours. Samples were taken periodically for HPLC analysis.

In the case of $CO_2$-extracted feed, the solution was similarly pH adjusted and filter sterilized. Fermentation media were prepared in 2.5 ml volumes with 1.875 ml of feed, 0.25 ml of 10x Yeast Nitrogen Base without Amino Acids, and 0.375 ml of water, which corresponded to a 75% dilution. A model solution was also prepared based on a 50% dilution of the mixture of analyzed compounds in the feed (100 ml/L 10x Yeast Nitrogen Base without Amino Acids, 110.93 mM xylose, 111.97 mM glucose, 106.14 mM GVL, 0.13 mM furfural, 19.925 mM acetic acid, 6.515 mM levulinic acid, 4.635 mM 5-HMF). Single colonies of *S. cerevisiae* PE2 on YPD agar were used to inoculate 5 ml overnights of the model solution in anaerobic hungate tubes (16×125 mm, Fisher Scientific). The tubes were capped and grown at 30° C. and 250 rpm agitation. These cultures were then used to seed the fermentation media to an $OD_{600}$ of 0.05 using the Nanodrop 2000c Spectophotometer (ThermoFisher) to measure OD. The tubes were sparged for 4 minutes with $N_2$ (Airgas) and 3 ml of air were reintroduced into the tubes with 3 ml syringes (BD & Co., Franklin Lakes, N.J.) to initiate cell growth by creating microaerobic conditions. The samples were incubated for 96 hours, during which HPLC samples were taken periodically.

In the case of the more concentrated $CO_2$-extracted feed produced by holding corn stover at 390 K for 1 hr followed by the 0.5 hr ramp from 430 to 490 K, the aqueous solution was similarly pH-adjusted and filter-sterilized. Fermentation media were prepared in 0.4 ml volumes with 0.3 ml of feed, 0.05 ml of 10x Yeast Nitrogen Base without Amino Acids, and 0.1 ml of water. A model sugar solution was also prepared based on a 25% dilution of the sugars analyzed in the feed (100 ml/L 10× Yeast Nitrogen Base without Amino Acids, 110.93 mM xylose, 111.97 mM glucose). Single colonies of *S. cerevisiae* PE2 on YPD agar were used to inoculate 5 ml overnights of the model solution in anaerobic hungate tubes (16×125 mm, Fisher Scientific). The tubes were capped and grown at 30° C. and 250 rpm agitation. The fermentation media, prepared in 1.8 ml autosampler glass vials (VWR), were seeded with 2 μl of the PE2 overnights. The tubes were sparged for 24 seconds with $N_2$ (Airgas) and 0.3 ml of air was reintroduced into the tubes with 1 ml syringes (BD) to initiate cell growth by creating microaerobic conditions. The samples were incubated at the same conditions previously described for 6 days, with initial and final HPLC samples taken.

*E. coli* Salt and GVL Toxicity Testing:

The strain used in these experiments was wild type *E. coli* MG1655 and in all cases was grown at 37° C. The toxicity medium used was based on MOPS minimal media with 0.5% glucose and supplemented with the appropriate wt % of GVL or sodium chloride (Sigma). A single colony of *E. coli* was picked from LB agar and grown overnight in 5 ml of LB media (glass culture tubes, 20×150 mm, Fisher Scientific) agitated at 250 rpm in an incubator shaker (New Brunswick Scientific). The resulting solution was used to inoculate 2 ml of the toxicity medium to an $OD_{600}$ of 0.01 in 13×100 mm tubes (Fisher Scientific). The tubes were incubated for 24 hours under the same conditions as described in the main methods and a final $OD_{600}$ measured using a Biomate 3 spectrophotometer (ThermoFisher).

*S. cerevisiae* Salt and GVL Toxicity Testing:

The strain used in these experiments was *S. cerevisiae* PE2 and in all cases was grown at 30° C. The toxicity medium used was formulated using 10x Yeast Nitrogen Base without Amino Acids, 0.5% glucose and the appropriate wt % of GVL or sodium chloride (Sigma). A single colony of *S. cerevisiae* was picked from YPD agar and grown overnight in 5 ml of YPD media (glass culture tubes, 20×150 mm, Fisher Scientific) agitated at 250 rpm in the incubator shaker. The resulting solution was used to inoculate 2 ml of the toxicity medium to an $OD_{600}$ of 0.01 in 13×100 mm tubes (Fisher Scientific). The tubes were incubated for 40 hours under same conditions and sampled as described above.

Analytical Methods:

The compositions of aqueous phases, GVL/water and ethanol/water were analyzed for glucose, xylose, ethanol, levulinic acid, GVL, 5-HMF and furfural and after a 10x dilution by weight in water using a Waters 2695 HPLC system with an Aminex HPX-87H column (Bio-Rad Labs, Hercules, Calif.) and an 5 mM $H_2SO_4$ aqueous mobile phase flowing at 0.6 ml/min. In the case where loblolly pine-derived glucose, mannose and xylose were analyzed, the same HPLC system was used with a Aminex HPX-87P column (Bio-Rad) and water as a mobile phase. Due to interference with an impurity in GVL, levulinic acid was measured by an undiluted injection in a GC (GC-2010, Shimadzu Corp, Kyoto, Japan) when analyzed in a GVL-water mixture. The SBP phase was analyzed using a Waters 2695 HPLC system with a Zorbax SB-C18 5 μm column (Agilent Technologies, Santa Clara, Calif.) using 5 mM $H_2SO_4$ as the aqueous phase with acetonitrile as the organic modifier. Both HPLC systems were equipped with an RI 2414 and a PDA 960 detector (Waters). Concentrations of sugars were measured using the RI detector, while concentrations of 5-HMF and furfural were measured using the PDA detector at 230 nm respectively. Oligomers were measured according to the procedure published by the National Renewable Energy Laboratory (25) using unstirred 10 ml thick-walled glass reactors (Grace-Davison) placed in an oil bath set to 393 K.

Water insoluble lignin in GVL/water fractions were measured by diluting the solutions 10 times using water and filtering the resulting mixture using a 0.2 μm nylon filter (Millipore, Billerica, Mass.) (14). The filter was dried overnight in a vacuum oven (Fisher-Scientific) set at 333 K and weighed to determine recovered solids.

Monomer Production:

The oligomers present in the recovered aqueous phase can be converted into monomers (preferable starting products for biological upgrading) in the acidic aqueous environment present in the aqueous phase (25). Using the aqueous phase separated by addition of salt from the product stream obtained using 80/20 GVL with a 2 hr temperature ramp, we demonstrate that more than 95% of the $C_5$ and $C_6$ carbohydrates can be recovered in the form of monomers after 100 min at 413 K. For streams produced using a 30 min temperature ramp, the 4-fold increase in the biomass to acid ratio led to significant neutralization of the original acid. Therefore, 25 mmol $H_2SO_4$ per liter of aqueous solution was supplemented to achieve yields around 90% for both salt and $CO_2$ extracted solutions. However, due to the higher concentration of acid used when holding biomass at 390 K for 1 hr with 0.15 M $H_2SO_4$, followed by the 0.5 hr temperature ramp using 5 mM H2SO4, the resulting aqueous solution did not necessitate acid supplementation and only required a 40 min residence time at 413 K for over 90% of the carbohydrates to be recovered as monomers.

GVL Recycle and Stability:

To investigate the effect of GVL recycle, the GVL-rich stream extracted during the first $CO_2$ extraction of the feed prepared using the 0.5 hr temperature ramp was used to prepare a 5 mM $H_2SO_4$ 80/20 GVL/water solution. In this recycle experiment, the GVL-rich stream was analyzed by HPLC to determine GVL content while it was assumed to contain no sulfuric acid. The prepared solution was then used for hydrolysis of the structural sugars from fresh corn stover using the flow-through reactor and the 0.5 hr 430-490 K temperature ramp. This sequence of $CO_2$-mediated GVL extraction followed by hydrolysis of fresh biomass was repeated for a second recycle. The resulting soluble carbohydrate yields were systematically 5-20% higher than the original yields obtained with "fresh" GVL, with a small drop (4-6%) in yields between the first and second recycle. This increase in yields is due to the small amounts of soluble carbohydrates that are present in the GVL-rich stream and thus contribute to the final yield.

REFERENCES CITED

The following documents are incorporated herein by reference.

1. E. L. Kunkes et al., Catalytic conversion of biomass to monofunctional hydrocarbons and targeted liquid-fuel classes, *Science* 322, 417 (2008).
2. P. Anbarasan et al., Integration of chemical catalysis with extractive fermentation to produce fuels, *Nature* 491, 235-239 (2012).
3. J. T. Youngquist, J. P. Rose, B. F. Pfleger, Free fatty acid production in *Escherichia coli* under phosphate-limited conditions, *Appl. Microbiol. Biotechnol.* 97, 5149-5159 (2013).
4. Y. Roman-Leshkov, J. N. Chheda, J. A. Dumesic, Phase modifiers promote efficient production of hydroxymethylfurfural from fructose, *Science* 312, 1933 (2006).
5. D. R. Dodds, R. A. Gross, Chemistry: Chemicals from Biomass, *Science* 318, 1250-1251 (2007).
6. D. M. Alonso, S. G. Wettstein, M. A. Mellmer, E. I. Gurbuz, J. A. Dumesic, Integrated conversion of hemicellulose and cellulose from lignocellulosic biomass, *Energy Environ. Sci.* 6, 76-80 (2012).
7. A. A. Peterson et al., Thermochemical biofuel production in hydrothermal media: A review of sub- and supercritical water technologies, *Energy Environ. Sci.* 1, 32-65 (2008).
8. M. von Sivers, G. Zacchi, A techno-economical comparison of three processes for the production of ethanol from pine, *Bioresour. Technol.* 51, 43-52 (1995).
9. J. B. Binder, R. T. Raines, Fermentable sugars by chemical hydrolysis of biomass, *Proc. Natl. Acad. Sci.* 107, 4516-4521 (2010).
10. K. Shill et al., Ionic liquid pretreatment of cellulosic biomass: Enzymatic hydrolysis and ionic liquid recycle, *Biotechnol. Bioeng.* 108, 511-520 (2011).
11. D. Klein-Marcuschamer, P. Oleskowicz-Popiel, B. A. Simmons, H. W. Blanch, The challenge of enzyme cost in the production of lignocellulosic biofuels, *Biotechnol. Bioeng.* 109, 1083-1087 (2012).
12. D. Humbird, A. Aden, *Biochemical production of ethanol from corn stover: 2008 state of technology model* (National Renewable Energy Laboratory, 2009).
13. Y. Y. Lee, P. Iyer, R. W. Torget, in *Recent Progress in Bioconversion of Lignocellulosics*, Advances in Biochemical Engineering/Biotechnology. P. D. G. T. Tsao et al., Eds. (Springer Berlin Heidelberg, 1999), pp. 93-115.
14. S. G. Wettstein, D. M. Alonso, Y. Chong, J. A. Dumesic, Production of levulinic acid and gamma-valerolactone (GVL) from cellulose using GVL as a solvent in biphasic systems, *Energy Environ. Sci.* 5, 8199-8203 (2012).

15. N. Mosier et al., Features of promising technologies for pretreatment of lignocellulosic biomass, *Bioresour. Technol.* 96, 673-686 (2005).
16. M. J. Selig et al., Deposition of Lignin Droplets Produced During Dilute Acid Pretreatment of Maize Stems Retards Enzymatic Hydrolysis of Cellulose, *Biotechnol. Prog.* 23, 1333-1339 (2007).
17. J. S. Luterbacher, Q. Chew, Y. Li, J. W. Tester, L. P. Walker, Producing concentrated solutions of monosaccharides using biphasic CO2-H2O mixtures, *Energy Environ. Sci.* 5, 6990-7000 (2012).
18. D. B. Hodge, M. N. Karim, D. J. Schell, J. D. McMillan, Soluble and insoluble solids contributions to high-solids enzymatic hydrolysis of lignocellulose, *Bioresour. Technol.* 99, 8940-8948 (2008).
19. Y. J. Pagán-Torres, T. Wang, J. M. R. Gallo, B. H. Shanks, J. A. Dumesic, Production of 5-Hydroxymethylfurfural from Glucose Using a Combination of Lewis and Brønsted Acid Catalysts in Water in a Biphasic Reactor with an Alkylphenol Solvent, *ACS Catal.* 2, 930-934 (2012).
20. E. I. Gürbüz et al., Conversion of Hemicellulose into Furfural Using Solid Acid Catalysts in γ-Valerolactone, *Angew. Chem. Int. Ed.* 125, 1308-1312 (2013).
21. M. W. Lau, B. E. Dale, Cellulosic ethanol production from AFEX-treated corn stover using *Saccharomyces cerevisiae* 424A(LNH-ST), *Proc. Natl. Acad. Sci.* 106, 1368-1373 (2009).
22. F. K. Kazi et al., Techno-economic comparison of process technologies for biochemical ethanol production from corn stover, *Fuel* 89, S20-S28 (2010).
23. L. Segal, J. J. Creely, A. E. Martin, C. M. Conrad, An Empirical Method for Estimating the Degree of Crystallinity of Native Cellulose Using the X-Ray Diffractometer, *Text. Res. J.* 29, 786-794 (1959).
24. S. Park, J. O. Baker, M. E. Himmel, P. A. Parilla, D. K. Johnson, Cellulose crystallinity index: measurement techniques and their impact on interpreting cellulase performance, *Biotechnol. Biofuels* 3, 10 (2010).
25. A. Sluiter et al., *Determination of sugars, byproducts, and degradation products in liquid fraction process samples* (National Renewable Energy Laboratory, Golden, Colo., 2004).
26. R. Turton, R. C. Bailie, W. B. Whiting, J. A. Shaeiwitz, *Analysis, synthesis and design of chemical processes* (Pearson Education, 2008).
27. J. Klemes, I. Bulatov, T. Cockerill, Techno-economic modelling and cost functions of $CO_2$ capture processes, *Comput. Chem. Eng.* 31, 445-455 (2007).
28. S. M. Sen et al., A sulfuric acid management strategy for the production of liquid hydrocarbon fuels via catalytic conversion of biomass-derived levulinic acid, *Energy Environ. Sci.* 5, 9690-9697 (2012).

What is claimed is:

1. A method of processing biomass, the method comprising reacting biomass with a solvent system comprising water, at least one acid selected from the group consisting of mineral acids and heterogeneous acids, and at least one organic compound selected from a lactone, for a time and at a temperature to yield a liquid fraction enriched in solubilized C5-sugar-containing oligomers and C-5 sugar monomers and a solid fraction enriched in substantially insoluble cellulose and C6-sugar-containing oligomers.

2. The method of claim 1, further comprising separating the liquid fraction from the solid fraction.

3. The method of claim 1, wherein the solvent system comprises (i) a lactone selected from the group consisting of beta-, gamma-, and delta-lactones, and combinations thereof, and (ii) at least about 5 wt % water.

4. The method of claim 1, wherein the lactone is gamma-valerolactone (GVL).

5. The method of claim 1, wherein the at least one organic compound is present in a mass ratio with water of about 70:30 to about 95:5.

6. The method of claim 1, wherein the at least one acid is heterogeneous.

7. The method of claim 1, wherein the at least one acid is a mineral acid.

8. The method of claim 1, wherein the at least one acid is present in the solvent system in concentration sufficient to yield a [$H^+$] concentration selected from the group consisting of about 0.05M to about 0.5M.

9. The method of claim 1, wherein the biomass is present in a concentration range selected from the group consisting of from about 5 wt % to about 70 wt %, based on the total weight of the biomass and solvent system.

10. The method of claim 1, wherein the biomass and the solvent system are reacted at a temperature of from about 90° C. to about 250° C. and for a time of from about 1 minute to about 24 hours.

11. The method of claim 10, wherein the biomass and the solvent system are reacted at a single temperature, a dynamic temperature range or a combination thereof.

12. The method of claim 11, wherein the dynamic temperature range ramps from a first temperature to a second temperature that is higher than the first temperature.

13. The method of claim 11, wherein the dynamic temperature range changes from a first temperature to a second temperature in a non-linear fashion or a linear fashion.

14. A method of processing biomass, the method comprising reacting biomass with a solvent system comprising water, a mineral acid, and gamma-valerolactone (GVL), for a time of from about 1 min to about 12 hrs, and at a temperature of from about 100° C. to about 200° C., wherein the reaction yields a liquid fraction enriched in solubilized C5-sugar-containing oligomers and C-5 sugar monomers and a solid fraction enriched in substantially insoluble cellulose and C6-sugar-containing oligomers.

15. The method of claim 14, further comprising separating the liquid fraction from the solid fraction.

16. The method of claim 14, wherein the solvent system comprises water, a mineral acid, and GVL, wherein the GVL is present in a mass ratio with water of about 70:30 to about 95:5.

17. The method of claim 14, wherein the at least one acid is present in the solvent system in a concentration sufficient to yield a [$H^+$] concentration of about 0.05M to about 0.5M.

18. The method of claim 14, wherein the biomass is present in a concentration ranging from about 5 wt % to about 70 wt % based on the total weight of the biomass and solvent system.

19. The method of claim 14, comprising reacting the biomass with the solvent system for about 1 min to about 1 hr, and at a temperature of from about 100° C. to about 140° C.

20. The method of claim 14, wherein the biomass is present in a concentration range from about 5 wt % to about 50 wt %, based on the total weight of the biomass and solvent system.

* * * * *